US010286042B2

(12) United States Patent
Spiegelman et al.

(10) Patent No.: US 10,286,042 B2
(45) Date of Patent: May 14, 2019

(54) METHODS FOR THE TREATMENT OF NEUROLOGICAL DISORDERS AND DISEASES USING FNDC5

(71) Applicant: Dana-Farber Cancer Institute, Inc., Boston, MA (US)

(72) Inventors: Bruce M. Spiegelman, Waban, MA (US); Christiane D. Wrann, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/026,381

(22) PCT Filed: Oct. 1, 2014

(86) PCT No.: PCT/US2014/058649

§ 371 (c)(1),
(2) Date: Mar. 31, 2016

(87) PCT Pub. No.: WO2015/051007

PCT Pub. Date: Apr. 9, 2015

(65) Prior Publication Data

US 2016/0213753 A1 Jul. 28, 2016

Related U.S. Application Data

(60) Provisional application No. 61/885,177, filed on Oct. 1, 2013.

(51) Int. Cl.

| | |
|---|---|
| ***A61K 38/17*** | (2006.01) |
| ***A61K 38/39*** | (2006.01) |
| ***A61K 48/00*** | (2006.01) |
| ***G01N 33/50*** | (2006.01) |
| ***G01N 33/68*** | (2006.01) |
| ***C12Q 1/6883*** | (2018.01) |

(52) U.S. Cl.

CPC .......... *A61K 38/39* (2013.01); *A61K 38/1709* (2013.01); *A61K 48/00* (2013.01); *C12Q 1/6883* (2013.01); *G01N 33/5023* (2013.01); *G01N 33/5058* (2013.01); *G01N 33/6896* (2013.01); *C12Q 2600/158* (2013.01); *G01N 2333/78* (2013.01); *G01N 2800/28* (2013.01); *G01N 2800/52* (2013.01)

(58) Field of Classification Search

CPC .... A61K 38/1709; A61K 38/39; A61K 48/00; C12Q 1/6883; C12Q 2600/158; G01N 2800/52; G01N 33/5058; G01N 33/5023; G01N 2333/78; G01N 2800/28; G01N 33/6896

See application file for complete search history.

(56) References Cited

U.S. PATENT DOCUMENTS

2009/0214637 A1 8/2009 Musatov
2013/0074199 A1 3/2013 Spiegelman et al.

OTHER PUBLICATIONS

Vickers. A vaccine against Alzheimer's disease: developments to date. Drugs Aging 2002; 19(7):487-94.*

Perrin et al. Multimodal techniques for diagnosis and prognosis of Alzheimer's disease. Nature Oct. 15, 2009;461(7266):916-22, Published online Oct. 14, 2009.*

Hampel et al. The future of Alzheimer's disease: the next 10 years. Prog Neurobiol. Dec. 2011;95(4):718-28. Epub Nov. 22, 2011.*

Kim et al. Brain-derived neurotropic factor and GABAergic transmission in neurodegeneration and neuroregeneration. Neural Regen Res. Oct. 2017; 12(10): 1733-1741. doi: 10.4103/1673-5374.217353.*

Kim et al. The Role of Irisin in Alzheimer's Disease. J Clin Med. Nov. 1, 2018;7(11). pii: E407. doi: 10.3390/jcm7110407.*

Dun et al., "Irisin-immunoreactivity in neural and non-neural cells of the rodent," Neurosci. 240:155-162 (2013).

Fitzsimons et al., "Epigenetic regulation of adult neural stem cells: implications for Alzheimer's disease," Mol. Neurodegeneration 9:25 (2014).

Hashemi et al., "FNDC5 Knockdown Significantly Decreased Neural Differentiation Rate of Mouse Embryonic Stem Cells," Neurosci. 231:296-304 (2013).

Moon et al., "Pharmacological concentrations of irisin increase cell proliferation without influencing markers of neurite outgrowth and synaptogenesis in mouse H19-7 hippocampal cell lines," Metabolism 62:1131-1136 (2013).

Nagahara et al., "Potential therapeutic uses of BDNF in neurological and psychiatric disorders," Nat. Rev. Drug Disc. 10:209-219 (2011).

Ostadsharif et al., "The expression of peroxisomal protein transcripts increased by retinoic acid during neural differentiation," Differentiation 81:127-132 (2011).

Phani et al., "VTA neurons show a potentially protective transcriptional response to MPTP," Brain Res. 1343:1-13 (2010).

Rasmussen et al., "Evidence for a release of brain-derived neurotrophic factor from the brain during exercise," Exp. Physiol. 94:1062-1069 (2009).

International Search Report dated Jan. 14, 2015 from PCT/US2014/058649.

Extended European Search Report for Application No. PCT/US2014/058649 dated Apr. 20, 2017.

* cited by examiner

*Primary Examiner* — Gregory S Emch
(74) *Attorney, Agent, or Firm* — Foley Hoag LLP

(57) ABSTRACT

The invention provides methods for identifying, assessing, preventing, and treating neurological disorders and diseases using Fndc5 and modulators of Fndc5 expression or activity.

12 Claims, 17 Drawing Sheets

Specification includes a Sequence Listing.

A
Cells
Media - deglyc.
GFP
FNDC5
B
C
D
E
F
G
H
GFP
FNDC5
Fndc5
Bdnf
DMSO
vehicle

SEQUENCE LISTING

<160> NUMBER OF SEQ ID NOS: 51

<210> SEQ ID NO 1
<211> LENGTH: 630
<212> TYPE: DNA
<213> ORGANISM: Mus musculus

<400> SEQUENCE: 1

```
atgcccccag ggccgtgcgc ctggccgccc cgcgccgcgc tccgcctgtg gctaggctgc      60

gtctgcttcg cgctggtgca ggcggacagc ccctcagccc ctgtgaacgt gaccgtccgg     120

cacctcaagg ccaactctgc cgtggtcagc tgggatgtcc tggaggatga agtggtcatt     180

ggctttgcca tctctcagca gaagaaggat gtgcggatgc tccggttcat tcaggaggtg     240

aacaccacca cccggtcctg cgctctctgg gacctggagg aggacacaga atatatcgtc     300

catgtgcagg ccatctccat ccagggacag agcccagcca gtgagcctgt gctcttcaag     360

accccacgcg aggctgaaaa gatggcctca aagaacaaag atgaggtgac catgaaggag     420

atggggagga accagcagct gcgaacgggg gaggtgctga tcattgttgt ggtcctcttc     480

atgtgggcag gtgttatagc tctcttctgc cgccagtatg atatcatcaa ggacaacgag     540

cccaataaca acaaggagaa aaccaagagc gcatcagaaa ccagcacacc ggagcatcag     600

ggtgggggtc tcctccgcag caagatatga                                      630
```

<210> SEQ ID NO 2
<211> LENGTH: 209
<212> TYPE: PRT
<213> ORGANISM: Mus musculus

<400> SEQUENCE: 2

```
Met Pro Pro Gly Pro Cys Ala Trp Pro Pro Arg Ala Ala Leu Arg Leu
1               5                   10                  15

Trp Leu Gly Cys Val Cys Phe Ala Leu Val Gln Ala Asp Ser Pro Ser
            20                  25                  30

Ala Pro Val Asn Val Thr Val Arg His Leu Lys Ala Asn Ser Ala Val
        35                  40                  45

Val Ser Trp Asp Val Leu Glu Asp Glu Val Val Ile Gly Phe Ala Ile
    50                  55                  60

Ser Gln Gln Lys Lys Asp Val Arg Met Leu Arg Phe Ile Gln Glu Val
65                  70                  75                  80

Asn Thr Thr Thr Arg Ser Cys Ala Leu Trp Asp Leu Glu Glu Asp Thr
                85                  90                  95

Glu Tyr Ile Val His Val Gln Ala Ile Ser Ile Gln Gly Gln Ser Pro
            100                 105                 110

Ala Ser Glu Pro Val Leu Phe Lys Thr Pro Arg Glu Ala Glu Lys Met
        115                 120                 125

Ala Ser Lys Asn Lys Asp Glu Val Thr Met Lys Glu Met Gly Arg Asn
    130                 135                 140

Gln Gln Leu Arg Thr Gly Glu Val Leu Ile Ile Val Val Val Leu Phe
145                 150                 155                 160

Met Trp Ala Gly Val Ile Ala Leu Phe Cys Arg Gln Tyr Asp Ile Ile
                165                 170                 175

Lys Asp Asn Glu Pro Asn Asn Asn Lys Glu Lys Thr Lys Ser Ala Ser
            180                 185                 190

Glu Thr Ser Thr Pro Glu His Gln Gly Gly Gly Leu Leu Arg Ser Lys
        195                 200                 205
```

Ile

<210> SEQ ID NO 3
<211> LENGTH: 462
<212> TYPE: DNA
<213> ORGANISM: Homo sapiens

<400> SEQUENCE: 3
atgctgcgct tcatccagga ggtgaacacc accacccgct catgtgccct ctgggacctg 60
gaggaggata cggagtacat agtccacgtg caggccatct ccattcaggg ccagagccca 120
gccagcgagc ctgtgctctt caagaccccg cgtgaggctg agaagatggc ctccaagaac 180
aaagatgagg taaccatgaa agagatgggg aggaaccaac agctgcggac aggcgaggtg 240
ctgatcatcg tcgtggtcct gttcatgtgg gcaggtgtca ttgccctctt ctgccgccag 300
tatgacatca tcaaggacaa tgaacccaat aacaacaagg aaaaaaccaa gagtgcatca 360
gaaaccagca caccagagca ccagggcggg gggcttctcc gcagcaaggt gagggcaaga 420
cctgggcctg ggtgggccac cctgtgcctc atgctctggt aa 462

<210> SEQ ID NO 4
<211> LENGTH: 153
<212> TYPE: PRT
<213> ORGANISM: Homo sapiens

<400> SEQUENCE: 4

Met Leu Arg Phe Ile Gln Glu Val Asn Thr Thr Thr Arg Ser Cys Ala
1 5 10 15

Leu Trp Asp Leu Glu Glu Asp Thr Glu Tyr Ile Val His Val Gln Ala
20 25 30

Ile Ser Ile Gln Gly Gln Ser Pro Ala Ser Glu Pro Val Leu Phe Lys
35 40 45

Thr Pro Arg Glu Ala Glu Lys Met Ala Ser Lys Asn Lys Asp Glu Val
50 55 60

Thr Met Lys Glu Met Gly Arg Asn Gln Gln Leu Arg Thr Gly Glu Val
65 70 75 80

Leu Ile Ile Val Val Val Leu Phe Met Trp Ala Gly Val Ile Ala Leu
85 90 95

Phe Cys Arg Gln Tyr Asp Ile Ile Lys Asp Asn Glu Pro Asn Asn Asn
100 105 110

Lys Glu Lys Thr Lys Ser Ala Ser Glu Thr Ser Thr Pro Glu His Gln
115 120 125

Gly Gly Gly Leu Leu Arg Ser Lys Val Arg Ala Arg Pro Gly Pro Gly
130 135 140

Trp Ala Thr Leu Cys Leu Met Leu Trp
145 150

<210> SEQ ID NO 5
<211> LENGTH: 414
<212> TYPE: DNA
<213> ORGANISM: Homo sapiens

<400> SEQUENCE: 5
atgctgcgct tcatccagga ggtgaacacc accacccgct catgtgccct ctgggacctg 60
gaggaggata cggagtacat agtccacgtg caggccatct ccattcaggg ccagagccca 120
gccagcgagc ctgtgctctt caagaccccg cgtgaggctg agaagatggc ctccaagaac 180
aaagatgagg taaccatgaa agagatgggg aggaaccaac agctgcggac aggcgaggtg 240

```
ctgatcatcg tcgtggtcct gttcatgtgg gcaggtgtca ttgccctctt ctgccgccag    300

tatgacatca tcaaggacaa tgaacccaat aacaacaagg aaaaaaccaa gagtgcatca    360

gaaaccagca caccagagca ccagggcggg gggcttctcc gcagcaagat atga          414
```

<210> SEQ ID NO 6
<211> LENGTH: 137
<212> TYPE: PRT
<213> ORGANISM: Homo sapiens

<400> SEQUENCE: 6

```
Met Leu Arg Phe Ile Gln Glu Val Asn Thr Thr Thr Arg Ser Cys Ala
1               5                   10                  15

Leu Trp Asp Leu Glu Glu Asp Thr Glu Tyr Ile Val His Val Gln Ala
            20                  25                  30

Ile Ser Ile Gln Gly Gln Ser Pro Ala Ser Glu Pro Val Leu Phe Lys
        35                  40                  45

Thr Pro Arg Glu Ala Glu Lys Met Ala Ser Lys Asn Lys Asp Glu Val
    50                  55                  60

Thr Met Lys Glu Met Gly Arg Asn Gln Gln Leu Arg Thr Gly Glu Val
65                  70                  75                  80

Leu Ile Ile Val Val Val Leu Phe Met Trp Ala Gly Val Ile Ala Leu
                85                  90                  95

Phe Cys Arg Gln Tyr Asp Ile Ile Lys Asp Asn Glu Pro Asn Asn Asn
            100                 105                 110

Lys Glu Lys Thr Lys Ser Ala Ser Glu Thr Ser Thr Pro Glu His Gln
        115                 120                 125

Gly Gly Gly Leu Leu Arg Ser Lys Ile
    130                 135
```

<210> SEQ ID NO 7
<211> LENGTH: 321
<212> TYPE: DNA
<213> ORGANISM: Homo sapiens

<400> SEQUENCE: 7

```
atgctgcgct tcatccagga ggtgaacacc accacccgct catgtgccct ctgggacctg    60

gaggaggata cggagtacat agtccacgtg caggccatct ccattcaggg ccagagccca   120

gccagcgagc ctgtgctctt caagaccccg cgtgaggctg agaagatggc ctccaagaac   180

aaagatgagg taaccatgaa agagatgggg aggaaccaac agctgcggac aggcgaggtg   240

ctgatcatcg tcgtggtcct gttcatgtgg gcaggtgtca ttgccctctt ctgccgccag   300

tatgacatca ttgaagcgtg a                                             321
```

<210> SEQ ID NO 8
<211> LENGTH: 106
<212> TYPE: PRT
<213> ORGANISM: Homo sapiens

<400> SEQUENCE: 8

```
Met Leu Arg Phe Ile Gln Glu Val Asn Thr Thr Thr Arg Ser Cys Ala
1               5                   10                  15

Leu Trp Asp Leu Glu Glu Asp Thr Glu Tyr Ile Val His Val Gln Ala
            20                  25                  30

Ile Ser Ile Gln Gly Gln Ser Pro Ala Ser Glu Pro Val Leu Phe Lys
        35                  40                  45
```

-continued

```
Thr Pro Arg Glu Ala Glu Lys Met Ala Ser Lys Asn Lys Asp Glu Val
    50                  55                  60

Thr Met Lys Glu Met Gly Arg Asn Gln Gln Leu Arg Thr Gly Glu Val
65                  70                  75                  80

Leu Ile Ile Val Val Val Leu Phe Met Trp Ala Gly Val Ile Ala Leu
                85                  90                  95

Phe Cys Arg Gln Tyr Asp Ile Ile Glu Ala
            100                 105


<210> SEQ ID NO 9
<211> LENGTH: 1203
<212> TYPE: DNA
<213> ORGANISM: Gallus gallus

<400> SEQUENCE: 9

atggagaaga acagggacgg ccgcggcccc cctggtgtcc atctggggat ggagaaggaa      60

gatgatttag agcccggtga cacgccgggg ctgcgcgaag ccctggtggc gagatgtcac     120

cgctgccgcg cacccgccgg gggtctcacc gggacgggcc ccgtttgctc cttccggcga     180

tggggagcgg tccgggccga gggctcccgg tcccgcctgg gggaaactga ggcagacggc     240

ggggccgggc ggggcggggg ccgagccgcc cccgggccgg gggagggacc ggagcggggc     300

tgcccagcgc tgcagcgggc ggagccgggg ctcggcgggg ccgcctcccg gccgagccga     360

gccgaaccga gccgcgctgc cgagggccgc cgagcccgca gccgcccccg gccgaaccgg     420

gcggccccgc cggttccggg ccccggagct ctccgcggtg ctgaacggcg ccgccgcgcc     480

cgcgggacgc cggccccgga gcggctcggc cccggcgcgg cgcggcgggc cgcgggggga     540

tggagccctt cctgggctgc accggcgccg cgctcctgct ctgctttcag ctacgccggt     600

ctgcggccgg tggaggcaga cagcccttcg gctccggtca atgtcacagt caaacacctg     660

aaggccaact cagctgtagt gacttgggac gttctggagg atgaagttgt cattggattt     720

gccatttccc agcagaagaa ggacgtgcgg atgctgcgct tcatccagga ggtgaacacc     780

accacccgct cctgtgccct ctgggaccta gaggaggaca ctgagtacat tgtgcatgtc     840

caggccatca gcatccaagg ccagagccct gccagtgagc cagtcctctt caagaccccc     900

agggaagctg agaaactggc ttctaaaaat aaagatgagg tgacaatgaa ggagatggcg     960

aagaaaaacc aacagctgcg cgcaggggaa atactcatca ttgtggtggt gttgtttatg    1020

tgggcagggg tgatcgccct gttctgcagg cagtacgaca tcatcaaaga caacgagccg    1080

aacaacagca aggagaaagc caagagcgcc tcagagaaca gcacccccga gcaccagggt    1140

ggggggctgc tccgcagcaa gttcccaaaa aacaaaccct cagtgaacat cattgaggca    1200

taa                                                                  1203


<210> SEQ ID NO 10
<211> LENGTH: 400
<212> TYPE: PRT
<213> ORGANISM: Gallus gallus

<400> SEQUENCE: 10

Met Glu Lys Asn Arg Asp Gly Arg Gly Pro Pro Gly Val His Leu Gly
1               5                   10                  15

Met Glu Lys Glu Asp Asp Leu Glu Pro Gly Asp Thr Pro Gly Leu Arg
            20                  25                  30

Glu Ala Leu Val Ala Arg Cys His Arg Cys Arg Ala Pro Ala Gly Gly
        35                  40                  45
```

-continued

```
Leu Thr Gly Thr Gly Pro Val Cys Ser Phe Arg Arg Trp Gly Ala Val
    50                  55                  60

Arg Ala Glu Gly Ser Arg Ser Arg Leu Gly Glu Thr Glu Ala Asp Gly
65                  70                  75                  80

Gly Ala Gly Arg Gly Gly Gly Arg Ala Ala Pro Gly Pro Gly Glu Gly
                85                  90                  95

Pro Glu Arg Gly Cys Pro Ala Leu Gln Arg Ala Glu Pro Gly Leu Gly
            100                 105                 110

Gly Ala Ala Ser Arg Pro Ser Arg Ala Glu Pro Ser Arg Ala Ala Glu
        115                 120                 125

Gly Arg Arg Ala Arg Ser Arg Pro Arg Pro Asn Arg Ala Ala Pro Pro
    130                 135                 140

Val Pro Gly Pro Gly Ala Leu Arg Gly Ala Glu Arg Arg Arg Arg Ala
145                 150                 155                 160

Arg Gly Thr Pro Ala Pro Glu Arg Leu Gly Pro Gly Ala Ala Arg Arg
                165                 170                 175

Ala Ala Gly Gly Trp Ser Pro Ser Trp Ala Ala Pro Ala Pro Arg Ser
            180                 185                 190

Cys Ser Ala Phe Ser Tyr Ala Gly Leu Arg Pro Val Glu Ala Asp Ser
        195                 200                 205

Pro Ser Ala Pro Val Asn Val Thr Val Lys His Leu Lys Ala Asn Ser
    210                 215                 220

Ala Val Val Thr Trp Asp Val Leu Glu Asp Glu Val Val Ile Gly Phe
225                 230                 235                 240

Ala Ile Ser Gln Gln Lys Lys Asp Val Arg Met Leu Arg Phe Ile Gln
                245                 250                 255

Glu Val Asn Thr Thr Thr Arg Ser Cys Ala Leu Trp Asp Leu Glu Glu
            260                 265                 270

Asp Thr Glu Tyr Ile Val His Val Gln Ala Ile Ser Ile Gln Gly Gln
        275                 280                 285

Ser Pro Ala Ser Glu Pro Val Leu Phe Lys Thr Pro Arg Glu Ala Glu
    290                 295                 300

Lys Leu Ala Ser Lys Asn Lys Asp Glu Val Thr Met Lys Glu Met Ala
305                 310                 315                 320

Lys Lys Asn Gln Gln Leu Arg Ala Gly Glu Ile Leu Ile Ile Val Val
                325                 330                 335

Val Leu Phe Met Trp Ala Gly Val Ile Ala Leu Phe Cys Arg Gln Tyr
            340                 345                 350

Asp Ile Ile Lys Asp Asn Glu Pro Asn Asn Ser Lys Glu Lys Ala Lys
        355                 360                 365

Ser Ala Ser Glu Asn Ser Thr Pro Glu His Gln Gly Gly Gly Leu Leu
    370                 375                 380

Arg Ser Lys Phe Pro Lys Asn Lys Pro Ser Val Asn Ile Ile Glu Ala
385                 390                 395                 400
```

<210> SEQ ID NO 11
<211> LENGTH: 555
<212> TYPE: DNA
<213> ORGANISM: Danio rerio

<400> SEQUENCE: 11

```
atgagttctt acagtttggc agctccagtg aatgtgtcca tcagggatct gaagagcagc      60

tcagccgtgg tgacatggga cacgccagac ggagagccag tcatcggctt cgccatcaca     120

caacagaaga aagatgtccg catgctgcgc tttattcaag aagtgaacac caccacgcgg     180
```

agctgtgcat tgtgggatct ggaagctgat acggattaca ttgtgcacgt tcagtctatc 240
agcatcagcg gggcgagtcc tgttagtgaa gctgtgcact tcaagacccc gacagaagtt 300
gaaacacagg cctccaagaa caaagacgag gtgacgatgg aggaggtcgg gccgaacgct 360
cagctcaggg ccggagagtt catcattatt gtggtggtcc tcatcatgtg ggcaggtgtg 420
atcgcactat tctgccgtca gtatgacatc attaaagaca acgaaccaaa caataacaag 480
gataaagcca agaactcgtc tgaatgcagc actccagagc acacgtcagg tggcctgctg 540
cgcagtaagg tataa 555

<210> SEQ ID NO 12
<211> LENGTH: 184
<212> TYPE: PRT
<213> ORGANISM: Danio rerio

<400> SEQUENCE: 12

Met Ser Ser Tyr Ser Leu Ala Ala Pro Val Asn Val Ser Ile Arg Asp
1 5 10 15

Leu Lys Ser Ser Ser Ala Val Val Thr Trp Asp Thr Pro Asp Gly Glu
20 25 30

Pro Val Ile Gly Phe Ala Ile Thr Gln Gln Lys Lys Asp Val Arg Met
35 40 45

Leu Arg Phe Ile Gln Glu Val Asn Thr Thr Thr Arg Ser Cys Ala Leu
50 55 60

Trp Asp Leu Glu Ala Asp Thr Asp Tyr Ile Val His Val Gln Ser Ile
65 70 75 80

Ser Ile Ser Gly Ala Ser Pro Val Ser Glu Ala Val His Phe Lys Thr
85 90 95

Pro Thr Glu Val Glu Thr Gln Ala Ser Lys Asn Lys Asp Glu Val Thr
100 105 110

Met Glu Glu Val Gly Pro Asn Ala Gln Leu Arg Ala Gly Glu Phe Ile
115 120 125

Ile Ile Val Val Val Leu Ile Met Trp Ala Gly Val Ile Ala Leu Phe
130 135 140

Cys Arg Gln Tyr Asp Ile Ile Lys Asp Asn Glu Pro Asn Asn Asn Lys
145 150 155 160

Asp Lys Ala Lys Asn Ser Ser Glu Cys Ser Thr Pro Glu His Thr Ser
165 170 175

Gly Gly Leu Leu Arg Ser Lys Val
180

<210> SEQ ID NO 13
<211> LENGTH: 336
<212> TYPE: DNA
<213> ORGANISM: Mus musculus

<400> SEQUENCE: 13
gacagcccct cagcccctgt gaacgtgacc gtccggcacc tcaaggccaa ctctgccgtg 60
gtcagctggg atgtcctgga ggatgaagtg gtcattggct ttgccatctc tcagcagaag 120
aaggatgtgc ggatgctccg gttcattcag gaggtgaaca ccaccacccg gtcctgcgct 180
ctctgggacc tggaggagga cacagaatat atcgtccatg tgcaggccat ctccatccag 240
ggacagagcc cagccagtga gcctgtgctc ttcaagaccc cacgcgaggc tgaaaagatg 300
gcctcaaaga acaaagatga ggtgaccatg aaggag 336

<210> SEQ ID NO 14
<211> LENGTH: 112
<212> TYPE: PRT
<213> ORGANISM: Mus musculus

<400> SEQUENCE: 14

```
Asp Ser Pro Ser Ala Pro Val Asn Val Thr Val Arg His Leu Lys Ala
1               5                   10                  15

Asn Ser Ala Val Val Ser Trp Asp Val Leu Glu Asp Glu Val Val Ile
            20                  25                  30

Gly Phe Ala Ile Ser Gln Gln Lys Lys Asp Val Arg Met Leu Arg Phe
        35                  40                  45

Ile Gln Glu Val Asn Thr Thr Thr Arg Ser Cys Ala Leu Trp Asp Leu
    50                  55                  60

Glu Glu Asp Thr Glu Tyr Ile Val His Val Gln Ala Ile Ser Ile Gln
65                  70                  75                  80

Gly Gln Ser Pro Ala Ser Glu Pro Val Leu Phe Lys Thr Pro Arg Glu
                85                  90                  95

Ala Glu Lys Met Ala Ser Lys Asn Lys Asp Glu Val Thr Met Lys Glu
            100                 105                 110
```

<210> SEQ ID NO 15
<211> LENGTH: 336
<212> TYPE: DNA
<213> ORGANISM: Homo sapiens

<400> SEQUENCE: 15

```
gacagtccct cagccccagt gaacgtcacc gtcaggcacc tcaaggccaa ctctgcagtg     60

gtgagctggg atgttctgga ggatgaggtt gtcatcggat ttgccatctc ccagcagaag    120

aaggatgtgc ggatgctgcg cttcatccag gaggtgaaca ccaccacccg ctcatgtgcc    180

ctctgggacc tggaggagga tacggagtac atagtccacg tgcaggccat ctccattcag    240

ggccagagcc cagccagcga gcctgtgctc ttcaagaccc cgcgtgaggc tgagaagatg    300

gcctccaaga acaaagatga ggtaaccatg aaagag                              336
```

<210> SEQ ID NO 16
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 16

```
catgcagaac ccacgacagt a                                               21
```

<210> SEQ ID NO 17
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 17

```
cctcacgcag cttgttgtct a                                               21
```

<210> SEQ ID NO 18
<211> LENGTH: 20
<212> TYPE: DNA

<213> ORGANISM: Artificial Sequence
<220> FEATURE:
<223> OTHER INFORMATION: /note="Description of Artificial Sequence:
Synthetic primer"

<400> SEQUENCE: 18
atgaaggaga tggggaggaa 20

<210> SEQ ID NO 19
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 19
gcggcagaag agagctataa ca 22

<210> SEQ ID NO 20
<211> LENGTH: 26
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 20
tgatgtgaat gacttggata cagaca 26

<210> SEQ ID NO 21
<211> LENGTH: 26
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 21
gctcattgtt gtactggttg gatatg 26

<210> SEQ ID NO 22
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 22
cactacggtg tggcatcctg 20

<210> SEQ ID NO 23
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 23
acagctgtac tcgatgctcc 20

<210> SEQ ID NO 24
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 24
aaccgaatgt cgtccgaaga c 21

<210> SEQ ID NO 25
<211> LENGTH: 19
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 25
gtggctgagg gcatcaatg 19

<210> SEQ ID NO 26
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 26
atggattcgg tagaactttg cc 22

<210> SEQ ID NO 27
<211> LENGTH: 22
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 27
cttcttcgta gtgcagggaa aa 22

<210> SEQ ID NO 28
<211> LENGTH: 20
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 28
tggccctgcg gaggctaagt 20

<210> SEQ ID NO 29
<211> LENGTH: 21
<212> TYPE: DNA
<213> ORGANISM: Artificial Sequence
<220> FEATURE:
<223> OTHER INFORMATION: /note="Description of Artificial Sequence:
Synthetic primer"

<400> SEQUENCE: 29
agggtgcttc cgagccttcc t 21

<210> SEQ ID NO 30
<211> LENGTH: 20
<212> TYPE: DNA
<213> ORGANISM: Artificial Sequence
<220> FEATURE:

<223> OTHER INFORMATION: /note="Description of Artificial Sequence:
      Synthetic primer"

<400> SEQUENCE: 30
tggatgctct tcagttcgtg 20

<210> SEQ ID NO 31
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 31
gtcttgggca tgtcagtgtg 20

<210> SEQ ID NO 32
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 32
ctgcatctac actcgcaagg 20

<210> SEQ ID NO 33
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 33
gccacaatgt cttcaagctc t 21

<210> SEQ ID NO 34
<211> LENGTH: 22
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 34
atgggctctc ctgtcaacac ac 22

<210> SEQ ID NO 35
<211> LENGTH: 24
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 35
atggctgtca ccgtggggat aaag 24

<210> SEQ ID NO 36
<211> LENGTH: 22
<212> TYPE: DNA
<213> ORGANISM: Artificial Sequence
<220> FEATURE:
<223> OTHER INFORMATION: /note="Description of Artificial Sequence:

Synthetic primer"

<400> SEQUENCE: 36
taccgttagc ccctatgcca tc 22

<210> SEQ ID NO 37
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 37
tgatattgct gagcctcaac tg 22

<210> SEQ ID NO 38
<211> LENGTH: 24
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 38
tatgagcacc tgaccacaga gtcc 24

<210> SEQ ID NO 39
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 39
cgagtcgttt ggctgggata ac 22

<210> SEQ ID NO 40
<211> LENGTH: 344
<212> TYPE: PRT
<213> ORGANISM: Artificial Sequence
<220> FEATURE:
<223> OTHER INFORMATION: /note="Description of Artificial Sequence: IrisinFc polypeptide"

<400> SEQUENCE: 40

```
Asp Ser Pro Ser Ala Pro Val Asn Val Thr Val Arg His Leu Lys Ala
1               5                   10                  15

Asn Ser Ala Val Val Ser Trp Asp Val Leu Glu Asp Glu Val Val Ile
            20                  25                  30

Gly Phe Ala Ile Ser Gln Gln Lys Lys Asp Val Arg Met Leu Arg Phe
        35                  40                  45

Ile Gln Glu Val Asn Thr Thr Thr Arg Ser Cys Ala Leu Trp Asp Leu
    50                  55                  60

Glu Glu Asp Thr Glu Tyr Ile Val His Val Gln Ala Ile Ser Ile Gln
65                  70                  75                  80

Gly Gln Ser Pro Ala Ser Glu Pro Val Leu Phe Lys Thr Pro Arg Glu
                85                  90                  95

Ala Glu Lys Met Ala Ser Lys Asn Lys Asp Glu Val Thr Met Lys Glu
            100                 105                 110

Gly Gly Gly Gly Ala Gly Gly Gly Gly Val Glu Cys Pro Pro Cys Pro
        115                 120                 125
```

```
Ala Pro Pro Val Ala Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Gln Phe Asn Trp Tyr Val
                165                 170                 175

Asp Gly Val Glu Val His Asn Ala Lys Thr Lys Pro Arg Glu Glu Gln
            180                 185                 190

Phe Asn Ser Thr Phe Arg Val Val Ser Val Leu Thr Val Val His Gln
        195                 200                 205

Asp Trp Leu Asn Gly Lys Glu Tyr Lys Cys Lys Val Ser Asn Lys Gly
    210                 215                 220

Leu Pro Ala Pro Ile Glu Lys Thr Ile Ser Lys Thr Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Met Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340


<210> SEQ ID NO 41
<211> LENGTH: 223
<212> TYPE: PRT
<213> ORGANISM: Artificial Sequence
<220> FEATURE:
<223> OTHER INFORMATION: /note="Description of Artificial Sequence:
      Control Fc polypeptide"

<400> SEQUENCE: 41

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
```

```
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 42
<211> LENGTH: 752
<212> TYPE: DNA
<213> ORGANISM: Artificial Sequence
<220> FEATURE:
<223> OTHER INFORMATION: /note="Description of Artificial Sequence: GFP nucleic acid"

<400> SEQUENCE: 42

```
aagcttggga tggtgagcaa gggcgaggag ctgttcaccg gggtggtgcc catcctggtc     60

gagctggacg gcgacgtaaa cggccacaag ttcagcgtgt ccggcgaggg cgagggcgat    120

gccacctacg gcaagctgac cctgaagttc atctgcacca ccggcaagct gcccgtgccc    180

tggcccaccc tcgtgaccac cctgacctac ggcgtgcagt gcttcagccg ctaccccgac    240

cacatgaagc agcacgactt cttcaagtcc gccatgcccg aaggctacgt ccaggagcgc    300

accatcttct tcaaggacga cggcaactac aagacccgcg ccgaggtgaa gttcgagggc    360

gacaccctgg tgaaccgcat cgagctgaag ggcatcgact tcaaggagga cggcaacatc    420

ctggggcaca agctggagta caactacaac agccacaacg tctatatcat ggccgacaag    480

cagaagaacg gcatcaaggt gaacttcaag atccgccaca acatcgagga cggcagcgtg    540

cagctcgccg accactacca gcagaacacc cccatcggcg acggccccgt gctgctgccc    600

gacaaccact acctgagcac ccagtccgcc ctgagcaaag accccaacga gaagcgcgat    660

cacatggtcc tgctggagtt cgtgaccgcc gccgggatca ctctcggcat ggacgagctg    720

tacaagtaac gcggatccac tagttctaga gc                                  752
```

<210> SEQ ID NO 43
<211> LENGTH: 21
<212> TYPE: DNA
<213> ORGANISM: Artificial Sequence
<220> FEATURE:
<223> OTHER INFORMATION: /note="Description of Artificial Sequence: shFndc5-1 target sequence"

<400> SEQUENCE: 43

```
ccctctgtga acatcatcaa a                                               21
```

<210> SEQ ID NO 44
<211> LENGTH: 58
<212> TYPE: DNA
<213> ORGANISM: Artificial Sequence
<220> FEATURE:
<223> OTHER INFORMATION: /note="Description of Artificial Sequence: shFndc5-1 shRNA oligonucleotide"

<400> SEQUENCE: 44

```
ccggccctct gtgaacatca tcaaactcga gtttgatgat gttcacagag ggtttttg       58
```

<210> SEQ ID NO 45
<211> LENGTH: 58
<212> TYPE: DNA
<213> ORGANISM: Artificial Sequence
<220> FEATURE:
<223> OTHER INFORMATION: /note="Description of Artificial Sequence: shFndc5-1 shRNA oligonucleotide"

<400> SEQUENCE: 45
aattcaaaaa ccctctgtga acatcatcaa actcgagttt gatgatgttc acagaggg 58

<210> SEQ ID NO 46
<211> LENGTH: 21
<212> TYPE: DNA
<213> ORGANISM: Artificial Sequence
<220> FEATURE:
<223> OTHER INFORMATION: /note="Description of Artificial Sequence: shFndc5-2 target sequence"

<400> SEQUENCE: 46
gtgcggatgc tccggttcat t 21

<210> SEQ ID NO 47
<211> LENGTH: 58
<212> TYPE: DNA
<213> ORGANISM: Artificial Sequence
<220> FEATURE:
<223> OTHER INFORMATION: /note="Description of Artificial Sequence: shFndc5-2 shRNA oligonucleotide"

<400> SEQUENCE: 47
ccgggtgcgg atgctccggt tcattctcga gaatgaaccg gagcatccgc actttttg 58

<210> SEQ ID NO 48
<211> LENGTH: 58
<212> TYPE: DNA
<213> ORGANISM: Artificial Sequence
<220> FEATURE:
<223> OTHER INFORMATION: /note="Description of Artificial Sequence: shFndc5-2 shRNA oligonucleotide"

<400> SEQUENCE: 48
aattcaaaaa gtgcggatgc tccggttcat tctcgagaat gaaccggagc atccgcac 58

<210> SEQ ID NO 49
<211> LENGTH: 21
<212> TYPE: DNA
<213> ORGANISM: Artificial Sequence
<220> FEATURE:
<223> OTHER INFORMATION: /note="Description of Artificial Sequence: shFndc5-3 target sequence"

<400> SEQUENCE: 49
cgagcccaat aacaacaagg a 21

<210> SEQ ID NO 50
<211> LENGTH: 58
<212> TYPE: DNA
<213> ORGANISM: Artificial Sequence
<220> FEATURE:
<223> OTHER INFORMATION: /note="Description of Artificial Sequence: shFndc5-3 shRNA oligonucleotide"

<400> SEQUENCE: 50
ccgggtgcgg atgctccggt tcattctcga gaatgaaccg gagcatccgc actttttg 58

```
<210> SEQ ID NO 51
<211> LENGTH: 58
<212> TYPE: DNA
<213> ORGANISM: Artificial Sequence
<220> FEATURE:
<223> OTHER INFORMATION: /note="Description of Artificial Sequence:
      shFndc5-3 shRNA oligonucleotide"

<400> SEQUENCE: 51

aattcaaaaa cgagcccaat aacaacaagg actcgagtcc ttgttgttat tgggctcg      58
```

METHODS FOR THE TREATMENT OF NEUROLOGICAL DISORDERS AND DISEASES USING FNDC5

CROSS-REFERENCE TO RELATED APPLICATIONS

This application claims the benefit of U.S. Provisional Application No. 61/885,177, filed on 1 Oct. 2013; the entire contents of said applications is incorporated herein in its entirety by this reference.

STATEMENT OF RIGHTS

This invention was made with government support under grant numbers RO1 DK31405 and DK90861 awarded by The National Institutes of Health. The government has certain rights in the invention.

BACKGROUND OF THE INVENTION

Exercise, especially endurance exercise, is known to have beneficial effects on brain health and cognitive function (Cotman et al. (2007) *Trends Neurosci.* 30, 464-472 and Mattson (2012) *Cell Metab.* 16, 706-722). This improvement in cognitive function with exercise has been most prominently observed in the aging population (Colcombe and Kramer (2003) *Psych Sci.* 14, 125-130). Exercise has also been reported to ameliorate outcomes in neurological diseases like depression, epilepsy, stroke, Alzheimer's and Parkinson's Disease (Ahlskog (2011) *Neurology* 77, 288-294; Arida et al. (2008) *Sports Med.* (Auckland, NZ) 38, 607-615; Buchman et al. (2012) *Neurology* 78, 1323-1329; Russo-Neustadt et al. (1999) *Neuropsychopharm.* 21, 679-682; and Zhang et al. (2012) *Neuroscience* 205, 10-17). The effects of exercise on the brain are most apparent in the hippocampus and its dentate gyrus, a part of the brain involved in learning and memory. Specific beneficial effects of exercise in the brain have been reported to include increases in the size of and blood flow to the hippocampus in humans and morphological changes in dendrites and dendritic spines, increased synapse plasticity and, importantly, de novo neurogenesis in the dentate gyrus in various mouse models of exercise (Cotman et al. (2007) *Trends Neurosci.* 30, 464-472 and Mattson (2012) *Cell Metab.* 16, 706-722). De novo neurogenesis in the adult brain occurs is observed in only two areas; the dentate gyrus of the hippocampus is one of them and exercise is one of the few known stimuli of this de novo neurogenesis (Kobilo et al. (2011) *Learning Mem.* (Cold Spring Harbor, N.Y.) 18, 605-609).

One important molecular mediator for these beneficial responses in the brain to exercise is the induction of neurotrophins/growth factors, most notably brain-derived neurotrophic factor (BDNF). In animal models, BDNF is induced in various regions of the brain with exercise and most robustly in the hippocampus (Cotman et al. (2007) *Trends Neurosci.* 30, 464-472). BDNF promotes many aspects of brain development including neuronal cell survival, differentiation, migration, dendritic arborization, synaptogenesis and plasticity (Greenberg et al. (2009) *J. Neurosci.* 29, 12764-12767 and Park and Poo (2013) *Nat. Rev. Neurosci.* 14, 7-23). In addition, BDNF is essential for synaptic plasticity, hippocampal function and learning (Kuípers et al. (2006) *Curr. Opin. Drug Disc. Dev.* 9, 580-586). Highlighting the relevance of BDNF in human, individuals carrying the Val66Met mutation in the BDNF gene, exhibit decreased secretion of BDNF, display a decreased volume of specific brain regions, deficits in episodic memory function as well as increased anxiety and depression (Egan et al. (2003) *Cell* 112, 257-269 and Haríri et al. (2003) *J. Neurosci.* 23, 6690-6694). Blocking BDNF signaling with anti-TrkB antibodies attenuates the exercise-induced improvement of acquisition and retention in a spatial learning task, as well as the exercise-induced expression of synaptic proteins (Vaynman et al. (2004) *Eur. J. Neurosci.* 20, 2580-2590 and Vaynman et al. (2006) *Brain Res.* 1070, 124-130). However, the underlying mechanism which induces BDNF in exercise remains to be determined.

PGC-1α is induced in skeletal muscle with exercise and is a major mediator of the beneficial effects of exercise in this tissue (Finck and Kelly (2006) *J. Clin. Invest.* 116, 615-622). PGC-1α was initially discovered as a transcriptional co-activator of mitochondrial biogenesis and oxidative metabolism in brown fat (Puigserver et al. (1998) *Cell* 92, 829-839 and Spiegelman (2007) *Novartis Foundation Sympos.* 287, 60-69). Subsequent work has demonstrated an important role of PGC-1α in the brain. Lack of PGC-1α in the brain is associated with neurodegeneration (Lin et al. (2004) *Cell* 119, 121-135 and Ma et al. (2010) *J. Biol. Chem.* 285, 39087-39095), as well as GABAergic dysfunction and a deficiency in neuronal parvalbumin expression (Lucas et al. (2010) *J. Neurosci.* 30, 7227-7235). PGC-1α has been shown to be neuroprotective in the MPTP mouse model of Parkinson's disease (St-Pierre et al. (2006) *Cell* 127, 397-408). It also negatively regulates extrasynaptic NMDA (N-methyl-D-aspartate) receptor activity and thereby reduces excitotoxicity in rat cortical neurons (Puddifoot et al. (2012) *J. Neurosci.* 32, 6995-7000). In addition, the involvement of PGC-1α in the formation and maintenance of neuronal dendritic spines has been reported by Cheng et al. (2012) *Nature Comm.* 3, 1250 and long-term forced treadmill running over 12 weeks increases Pgc1α expression in various areas of the brain (Steiner et al. (2011) *J. Appl. Physiol,* 111, 1066-1071).

It has been determined that a PGC-1α-dependent myokine, FNDC5, is cleaved and secreted from muscle during exercise and induces some major metabolic benefits of exercise (Bostrom et al. (2012) *Nature* 481, 463-468). FNDC5 is a glycosylated type I membrane protein and is released into the circulation after proteolytic cleavage. The secreted form of FNDC5 contains 112 amino acids and has been named irisin. Irisin acts preferentially on the subcutaneous 'beige' fat and causes it to 'brown' by increasing the expression of UCP-1 and other thermogenic genes (Bostrom et al. (2012) *Nature* 481, 463-468 and Wu et al. (2012) *Cell* 150, 366-376). Clinical studies in humans have confirmed this positive correlation between increased FNDC5 expression and circulating irisin with the level of exercise performance (Huh et al. (2012) *Metabolism* 61, 1725-1738 and Lecker et al. (2012) *Circ. Heart Failure* 5, 812-818).

FNDC5 is also expressed in the brain (Dun et al. (2013) *Neurosci.* 240, 155-162; Ferrer-Martinez et al. (2002) *Dev. Dyn.* 224, 154-167; and Teufel et al. (2002) *Gene* 297, 79-83) and in rat pheochromocytoma-derived PC12 cells differentiated into neuron-like cells (Ostadsharif et al. (2011) *Diff. Res. Biol. Diversity* 81, 127-132). Knockdown of FNDC5 in neuronal precursors impaired the development into mature neurons (Hashemi et al. (2013) *Neurosci.* 231, 296-304) and in vitro application of irisin to mouse H19-7 HN hippocampal cells increased cell proliferation without altering markers of hippocampal neurogenesis (Moon et al. (2013) *Metabolism* 62:1131-1136).

Despite the identification of BDNF and other neuromodulatory (e.g., neuroprotective) factors as important regulators of neuronal development and function, such molecules are unstable, difficult to administer to the central nervous system, and are non-specific, general molecules having a range of functions on different parts of the central and peripheral nervous systems. A major part of the pathology of neurodegenerative disease is the progressive destruction and loss of neurons followed by loss of neurological function. Therapeutic efforts have concentrated on the protection and preservation of the endangered neurons as well as regeneration of new neurons. While neurotrophins, which are neuroprotective, promote nerve cell growth and survival, and have been become prime candidates because of their major therapeutic effects in animal studies, clinical trials using neurotrophins themselves as therapeutics have not been successful thus far for the reasons described above. Yet, there is a growing need for such therapeutics. Impairment of the nervous system caused by neurodegenerative diseases, such as Alzheimer's disease or Parkinson's disease, and the associated disability is devastating for the people suffering from it. In the United States at least one million people are believed to suffer from Parkinson's disease and about 60,000 people are newly diagnosed each year. The annual costs alone for Parkinson's disease are estimated at $25 billion per year in the U.S., including the cost of treatment, social security payments and lost income from inability to work.

Accordingly, there is a great need to identify molecular regulators of such neuromodulatory (e.g., neuroprotective) factors having improved properties for administration, neuromodulatory specificity, and stability, including the generation of diagnostic, prognostic, and therapeutic agents to effectively regulate neurological processes in subjects.

SUMMARY OF THE INVENTION

The present invention is based in part on the discovery that Fndc5 and biologically active fragments thereof are secreted polypeptides whose expression is elevated by endurance exercise in the hippocampus and other brain areas; that PGC-1α and FNDC5 regulate BDNF expression in the brain; and, that FNDC5 promotes survival of neurons and inhibits neurodegeneration mediated by its effects on BDNF expression. It was unexpectedly determined that BDNF expression or activity could be modulated in the central and/or peripheral nervous system in subjects by administering an Fndc5 or irisin polypeptide, either within the nervous system or, surprisingly, systemically in the plasma.

In one aspect, as method of increasing expression of brain-derived neurotrophic factor (BDNF) by a cell is provided comprising, contacting the cell with an agent, wherein the agent is selected from the group consisting of an Fndc5 polypeptide or fragment thereof, a nucleic acid that encodes Fndc5 or a fragment thereof, and an enhancer of Fndc5 polypeptide and/or nucleic acid expression and/or activity, to thereby increase the expression of BDNF by the cell. In one embodiment, the step of contacting occurs in vivo, ex vivo, or in vitro. In another embodiment, the cells are neurons (e.g., hippocampal neurons, cerebellar neurons, sciatic nerve neurons, dopaminergic neurons, or substantia nigra neurons). In still another embodiment, the method further comprises contacting the cell with an additional agent that increases the expression of BDNF.

In another aspect, a method for treating or preventing a neurological disease or disorder in a subject is provided comprising the step of administering to the subject an agent selected from the group consisting of an Fndc5 polypeptide or fragment thereof, a nucleic acid that encodes Fndc5 or a fragment thereof, and an enhancer of Fndc5 polypeptide and/or nucleic acid expression and/or activity, that increases BDNF expression or activity in the central or peripheral nervous system of the subject, such that the neurological disease or disorder is treated or prevented. In one embodiment, the agent is administered systemically (e.g., intravenous or subcutaneous administration). In another embodiment, the agent is administered in a pharmaceutically acceptable formulation. In still another embodiment, the neurological disease or disorder would benefit from decreased neuronal cell death and/or increased neuronal survival, optionally wherein the neurological disease or disorder is selected from the group consisting of Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders. In yet another embodiment, the subject is a human.

In still another aspect, a method for assessing whether a subject is afflicted with a neurological disease or disorder or has a risk of developing a neurological disease or disorder is provided comprising the steps of detecting the expression of the Fndc5 gene or the expression or activity of Fndc5 polypeptide in a sample of a subject, wherein a decrease in the expression of the Fndc5 gene or a decrease in the expression or activity of the Fndc5 polypeptide compared to a control indicates the presence of a neurological disease or disorder or the risk of developing a neurological disease or disorder in the subject. In one embodiment, the sample is selected from the group consisting of whole blood, serum, plasma, saliva, cerebrospinal fluid, spinal fluid, and neural tissue. In another embodiment, the expression of the Fndc5 polypeptide or protein thereof is detected using a reagent which specifically binds with the protein (e.g., an antibody, an antibody derivative, and an antibody fragment). In still another embodiment, the expression of the Fndc5 gene is assessed by detecting the presence in the sample of a transcribed polynucleotide or portion thereof (e.g., an mRNA or a cDNA). In yet another embodiment, the step of detecting further comprises amplifying the transcribed polynucleotide. In another embodiment, the level of expression of the marker in the sample is assessed by detecting the presence in the sample of a transcribed polynucleotide which anneals with Fndc5 or anneals with a portion of an Fndc5 polynucleotide under stringent hybridization conditions. In still another embodiment, the neurological disease or disorder would benefit from decreased neuronal cell death and/or increased neuronal survival, optionally wherein the neurological disease or disorder is selected from the group consisting of Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders. In yet another embodiment, the subject is a human.

In yet another aspect, a method for assessing the efficacy of an agent that treats or prevents a neurological disease or disorder in a subject is provided comprising: a) detecting in a subject sample at a first point in time BDNF polypeptide or nucleic acid expression and/or activity in the central and/or peripheral nervous system; b) repeating step a) during at least one subsequent point in time after administration of the agent, wherein the agent is selected from the group consisting of an Fndc5 polypeptide or fragment thereof, a nucleic acid that encodes Fndc5 or a fragment thereof, and an enhancer of Fndc5 polypeptide and/or nucleic acid expression and/or activity; and c) comparing the expression and/or activity detected in steps a) and b), wherein a significantly increased BDNF polypeptide or nucleic acid expression and/or activity in the first subject sample relative to at least one subsequent subject sample, indicates that the agent treats or prevents the neurological disease or disorder in the subject. In one embodiment, the first and/or at least one subsequent sample is selected from the group consisting of whole blood, serum, plasma, saliva, cerebrospinal fluid, spinal fluid, and neural tissue. In another embodiment, the subject has undergone treatment, completed treatment, and/or is in remission for the neurological disease or disorder in between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of the neurological disease or disorder. In another embodiment, the first and/or at least one subsequent sample is a portion of a single sample or pooled samples obtained from the subject. In still another embodiment, the expression of the BDNF polypeptide is detected using a reagent which specifically binds with the protein (e.g., an antibody, an antibody derivative, and an antibody fragment). In yet another embodiment, the expression of the BDNF nucleic acid is assessed by detecting the presence in the sample of a transcribed polynucleotide or portion thereof (e.g., an mRNA or a cDNA). In another embodiment, the step of detecting further comprises amplifying the transcribed polynucleotide. In still another embodiment, the level of expression of the marker in the sample is assessed by detecting the presence in the sample of a transcribed polynucleotide which anneals with BDNF or anneals with a portion of a BDNF polynucleotide under stringent hybridization conditions.

In another aspect, a cell-based assay for screening for agents that modulate the ability of the cell to increase BDNF expression is provided comprising contacting the cell with a test agent selected from the group consisting of an Fndc5 polypeptide or fragment thereof, a nucleic acid that encodes Fndc5 or a fragment thereof, and an enhancer of Fndc5 polypeptide and/or nucleic acid expression and/or activity, and determining the ability of the test agent to increase BDNF expression by the cell. In one embodiment, the step of contacting occurs in vivo, ex vivo, or in vitro. In another embodiment, the cells are neurons (e.g., hippocampal neurons, cerebellar neurons, sciatic nerve neurons, dopaminergic neurons, or substantia nigra neurons).

Further provided are embodiments that can be applied to any composition or method of the present invention described herein. For example, in one embodiment, the Fndc5 polypeptide is selected from the group of polypeptides consisting of: a) a polypeptide encoded by a nucleic acid molecule comprising a nucleotide sequence encoding a fragment of the FNDC5 polypeptide of SEQ ID NO: 2, wherein said fragment lacks the C-terminal domain sequence of said FNDC5 polypeptide, and wherein said polypeptide has one or more of the biological activities of said FNCD5 polypeptide; b) an isolated polypeptide encoded by a nucleic acid molecule comprising a nucleotide sequence encoding an amino acid sequence that is at least 70% identical to the amino acid sequence of residues 73-140 of the FNDC5 polypeptide of SEQ ID NO:2, wherein said polypeptide does not encode the C-terminal domain sequence of said FNDC5 polypeptide, and wherein said polypeptide has one or more of the biological activities of said FNCD5 polypeptide; c) a polypeptide which is a fragment of the FNDC5 polypeptide SEQ ID NO: 2, which fragment is optionally fused to one or more heterologous polypeptides at its N-terminus and/or C-terminus, wherein said fragment consists of a sequence of amino acids in between residues 1 and 150 of SEQ ID NO: 2, and wherein said fragment has one or more of the biological activities of said FNCD5 polypeptide; and d) a polypeptide which is a fragment of the FNDC5 polypeptide of SEQ ID NO: 4, 6 or 8, wherein said fragment is optionally fused to one or more heterologous polypeptides at its N-terminus and/or C-terminus, and wherein said fragment has one or more of the biological activities of said FNCD5 polypeptide. In another embodiment, the Fndc5 polypeptide is selected from the group of polypeptides consisting of: a) an isolated polypeptide fragment of an Fndc5 protein comprising at least one fibronectin domain and is not full-length Fndc5; b) an isolated polypeptide fragment of an Fndc5 protein comprising at least one fibronectin domain and which lacks one or more functional domain(s) selected from the group consisting of signal peptide, hydrophobic, and C-terminal domains; c) an isolated polypeptide comprising an amino acid sequence that is at least 70% identity to the amino acid sequence comprising residues 73-140 of SEQ ID NO:2, residues 30-140 of SEQ ID NO:2 or residues 29-140 of SEQ ID NO:2 and which lacks one or more functional domain(s) of an Fndc5 protein selected from the group consisting of signal peptide, hydrophobic, and C-terminal domains; d) an isolated polypeptide comprising an amino acid sequence that is at least 70% identity to the amino acid sequence comprising residues 73-140 of SEQ ID NO:2, residues 30-140 or SEQ ID NO:2 or residues 29-140 or SEQ ID NO:2 and which is less than 195 amino acids in length; e) an isolated polypeptide consisting essentially of an amino acid sequence that is at least 70% identity to the amino acid sequence comprising residues 73-140 of SEQ ID NO:2, residues 30-140 of SEQ ID NO:2 or residues 29-140 of SEQ ID NO:2; f) an isolated polypeptide fragment of SEQ ID NO:2 comprising residues 73-140 of SEQ ID NO:2, residues 30-140 of SEQ ID NO:2 or residues 29-140 of SEQ ID NO:2 and which is not full-length; g) an isolated polypeptide fragment of SEQ ID NO:2 consisting essentially of residues 73-140 of SEQ ID NO:2, residues 30-140 of SEQ ID NO:2 or residues 29-140 of SEQ ID NO:2; h) an isolated polypeptide which is encoded by a nucleic acid molecule comprising a nucleotide sequence encoding at least one fibronectin domain of an Fndc5 protein and does not encode full-length Fndc5; i) an isolated polypeptide fragment of an Fndc5 protein which is encoded by a nucleic acid molecule comprising a nucleotide sequence encoding at least one fibronectin domain and which does not encode one or more functional domain(s) selected from the group consisting of signal peptide, hydrophobic, and C-terminal domains; j) an isolated polypeptide which is encoded by a nucleic acid molecule comprising a nucleotide sequence encoding an amino acid sequence that is at least 70% identical to the amino acid sequence of residues 73-140 of SEQ ID NO:2, residues 30-140 of SEQ ID NO:2 or residues 29-140 of SEQ ID NO:2 and which does not encode one or more functional domain(s) of an Fndc5 protein selected from the group consisting of signal peptide, hydrophobic, and C-terminal domains; k) an isolated polypeptide which is encoded by a nucleic acid molecule comprising a nucleotide sequence encoding an amino acid sequence that is at least 70% identical to the amino acid sequence of residues 73-140 of SEQ ID NO:2, residues 30-140 of SEQ ID NO:2 or residues 29-140 of SEQ ID NO:2 and which is less than 630 nucleotides in length; l) an isolated polypeptide which is encoded by a nucleic acid molecule consisting essentially of a nucleotide sequence encoding an amino acid sequence having at least 70% identity to the amino acid sequence of residues 73-140 of SEQ ID NO:2, residues 30-140 of SEQ ID NO:2 or residues 29-140 of SEQ ID NO:2; m) an isolated polypeptide which is encoded by a nucleic acid molecule comprising a nucleotide sequence encoding an amino acid sequence that is at least 70% identical to the amino acid sequence of residues 73-140 of SEQ ID NO:2, residues 30-140 of SEQ ID NO:2 or residues 29-140 of SEQ ID NO:2 and which does not encode the full-length amino acid sequence of SEQ ID NO:2; n) an isolated polypeptide which is encoded by a nucleic acid molecule comprising a nucleotide sequence encoding the amino acid sequence of residues 73-140 of SEQ ID NO:2, residues 30-140 of SEQ ID NO:2 or residues 29-140 of SEQ ID NO:2 and which does not encode the full-length amino acid sequence of SEQ ID NO:2; o) an isolated polypeptide which is encoded by a nucleic acid molecule consisting essentially of a nucleotide sequence encoding the amino acid sequence of residues 73-140 of SEQ ID NO:2, residues 30-140 of SEQ ID NO:2 or residues 29-140 of SEQ ID NO:2; p) an isolated polypeptide which is encoded by a nucleic acid molecule comprising a nucleotide sequence which is at least 70% identical to the nucleotide sequence of nucleotides 217-420 of SEQ ID NO:1, SEQ ID NO:15, nucleotides 88-420 of SEQ ID NO:1, or nucleotides 85-420 of SEQ ID NO:1 and which does not encode one or more functional domain(s) of an Fndc5 protein selected from the group consisting of signal peptide, hydrophobic, and C-terminal domains; and q) an isolated polypeptide which is encoded by a nucleic acid molecule consisting essentially of a nucleotide sequence which is at least 70% identical to the nucleotide sequence of nucleotides 217-420 of SEQ ID NO:1, SEQ ID NO:15, nucleotides 88-420 of SEQ ID NO:1, or nucleotides 85-420 of SEQ ID NO:1.

In still another embodiment, the one or more of the biological activities of FNDC5 polypeptide is selected from the group consisting of 1) increasing BDNF expression in the central and/or peripheral nervous system; 2) increasing activity-induced immediate-early gene expression in neurons; 3) increasing neuronal survival; 4) decreasing neurological lesion formation; 5) increasing neurite outgrowth; 6) increasing synaptogenesis; 7) increasing synaptic plasticity; 8) decreasing neuronal mitochondrial dysfunction; 9) increasing dendritic arborization; 10) increasing neuronal differentiation; and 11) increasing neuronal migration. In yet another embodiment, the fragment or encoded amino acid sequence is more than 65 amino acids in length and/or less than 135 amino acids in length. In another embodiment, the polypeptide is between 70 and 125 amino acids in length or is less than 195 amino acids in length. In still another embodiment, the polypeptide is a fragment of SEQ ID NO: 2 which consists of about amino acids 30 to 140 or 73-140 SEQ ID NO: 2, wherein said fragment is optionally fused to one or more heterologous polypeptides at its N-terminus and/or C-terminus. In yet another embodiment, the polypeptide comprises a fibronectin domain. In another embodiment, the polypeptide is glycosylated or pegylated, optionally wherein at least one glycosylated amino acid residue corresponds to asparagine at position 36 and/or the asparagine at position 81 of SEQ ID NO:2. In still another embodiment, the polypeptide comprises an amino acid sequence that is heterologous to said FNDC5 polypeptide (e.g., an Fc domain, an IgG1 Fc domain, an IgG2 Fc domain, an IgG3 Fc domain, and IgG4 Fc domain, a dimerization domain, an oligomorization domain, an agent that promotes plasma solubility, albumin, a signal peptide, a peptide tag, a 6-His tag, a thioredoxin tag, a hemaglutinin tag, a GST tag, or an OmpA signal sequence tag). In yet another embodiment, the polypeptide can cross the blood-brain barrier. In another embodiment, the Fndc5 nucleic acid encodes an Fndc5 polypeptide described herein. In still another embodiment, the Fndc5 nucleic acid is selected from the group consisting of: a) a nucleic acid molecule comprising a nucleotide sequence encoding a fragment of the FNDC5 polypeptide SEQ ID NO: 2, wherein said fragment lacks the C-terminal domain sequence of said FNDC5 polypeptide, and wherein said fragment has one or more of the biological activities of said FNCD5 polypeptide; b) a nucleic acid molecule which encodes a polypeptide comprising an amino acid sequence having at least 70% identity to the amino acid sequence of residues 73-140 of the FNDC5 polypeptide of SEQ ID NO:2, wherein said polypeptide does not encode the C-terminal domain sequence of said FNDC5 polypeptide, and wherein said polypeptide has one or more of the biological activities of said FNCD5 polypeptide; and c) a nucleic acid molecule which encodes a fibronectin domain of the FNCD5 polypeptide of SEQ ID NO: 2 but which does not encode the full length sequence of SEQ ID NO: 2. In yet another embodiment, the Fndc5 nucleic acid is selected from the group consisting of: a) an isolated nucleic acid molecule which encodes at least one fibronectin domain of an Fndc5 protein and which does not encode full-length Fndc5; b) an isolated nucleic acid molecule which encodes at least one fibronectin domain of an Fndc5 protein and which does not encode one or more functional domain(s) of an Fndc5 protein selected from the group consisting of signal peptide, hydrophobic, and C-terminal domains; c) an isolated nucleic acid molecule which encodes a polypeptide comprising an amino acid sequence having at least 70% identity to the 88-amino acid sequence of residues 73-140 of SEQ ID NO:2, residues 30-140 of SEQ ID NO:2 or residues 29-140 of SEQ ID NO:2 and which does not encode one or more functional domain(s) of an Fndc5 protein selected from the group consisting of signal peptide, hydrophobic, and C-terminal domains; d) an isolated nucleic acid molecule which encodes a polypeptide comprising an amino acid sequence having at least 70% identity to the amino acid sequence of residues 73-140 of SEQ ID NO:2, residues 30-140 of SEQ ID NO:2 or residues 29-140 of SEQ ID NO:2 and which is less than 630 nucleotides in length; e) an isolated nucleic acid molecule which encodes a polypeptide consisting essentially of an amino acid sequence having at least 70% identity to the amino acid sequence of residues 73-140 of SEQ ID NO:2, residues 30-140 of SEQ ID NO:2 or residues 29-140 of SEQ ID NO:2; f) an isolated nucleic acid molecule which encodes a polypeptide comprising an amino acid sequence having at least 70% identity to the amino acid sequence of residues 73-140 of SEQ ID NO:2, residues 30-140 of SEQ ID NO:2 or residues 29-140 of SEQ ID NO:2 and which does not encode the full-length amino acid sequence SEQ ID NO:2; g) an isolated nucleic acid molecule which encodes a polypeptide comprising the amino acid sequence of residues 73-140 of SEQ ID NO:2, residues 30-140 of SEQ ID NO:2 or residues 29-140 of SEQ ID NO:2 and which does not encode the full-length amino acid sequence of SEQ ID NO:2; b) an isolated nucleic acid molecule which encodes a polypeptide consisting essentially of the amino acid sequence of residues 73-140 of SEQ ID NO:2, residues 30-140 of SEQ ID NO:2 or residues 29-140 of SEQ ID NO:2; i) an isolated nucleic acid molecule comprising a nucleotide sequence which is at least 70% identical to the nucleotide sequence of nucleotides 217-420 of SEQ ID NO:1, SEQ ID NO:15, nucleotides 88-420 SEQ ID NO:1, or nucleotides 85-420 of SEQ ID NO:1 and which does not encode one or more functional domain(s) of an Fndc5 protein selected from the group consisting of signal peptide, hydrophobic, and C-terminal domains; and j) an isolated nucleic acid molecule consisting essentially of a nucleotide sequence which is at least 70% identical to the nucleotide sequence of nucleotides 217-420 of SEQ ID NO:1, SEQ ID NO:15, nucleotides 88-420 of SEQ ID NO:1, or nucleotides 85-420 of SEQ ID NO:1.

BRIEF DESCRIPTION OF FIGURES

FIGS. 1A-1E show the results of male six week old C57/Bl6 wild type mice that were individually housed in cages with access to a running-wheel (free wheel-running) or without (sedentary). Mice were exercised for 30 days and sacrificed approximately 10 h after their last bout of exercise. The quadriceps muscle (quadriceps) was harvested. The brain was retrieved and the hippocampus was dissected out. mRNA was prepared and gene expression was assessed by qPCR. Data are shown as mRNA levels relative to Rsp18 expression, expressed as mean±SEM. *P<0.05 compared to sedentary control group.

FIG. 3A shows the results of the indicated tissues harvested from male 13 week old C57/Bl6 wild type mice. mRNA was prepared and gene expression was assessed by qPCR. Data are shown as mRNA levels relative to Rsp18 expression, expressed as mean±SEM. Quad=quadriceps muscle, Gastroc=gastrocnemius muscle, Sp. Cord=spinal cord, ingWAT=inguinal white adipose tissue, epiWAT=epididymal white adipose tissue, iBAT=interscapular brown adipose tissue. FIG. 3B shows the results of brains harvested from C57/Bl6 wild type mice at the indicated postnatal (P) time points. mRNA was prepared and gene expression was assessed by qPCR. Data are shown as mRNA levels relative to Rsp18 expression, expressed as mean±SEM. FIG. 3C shows the results of primary cortical neurons isolated from C57/Bl6 wild type E17 embryos and cultured in vitro. At the indicated days in vitro (DIV) mRNA was prepared and gene expression was assessed by qPCR. Data are shown as mRNA levels relative to Rsp18 expression, expressed as mean±SEM. *P<0.05 compared to DIV 1 control group.

FIG. 4A shows the results of primary cortical neurons at DIV 7 treated with either forskolin (10 μM), a stimulator intracellular cAMP levels, or vehicle for overnight. mRNA was prepared and gene expression was assessed by qPCR. Data are shown as mRNA levels relative to Rsp18 expression, expressed as mean±SEM. *P<0.05 compared to vehicle only group. FIG. 4B shows the results of primary cortical neurons at DIV 7 treated with nifedipine (5 μM), a L-type calcium channel blocker, or vehicle for overnight. mRNA was prepared and gene expression was assessed by qPCR. Data are shown as mRNA levels relative to Rsp18 expression, expressed as mean±SEM. *P<0.05 compared to vehicle only group. FIG. 4C shows the results of primary cortical neurons at DIV 7 transduced with either PGC-1α or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding GFP expressing control group. FIG. 4D shows the results of primary cortical neurons at DIV 5 transduced with lentivirus carrying the specified shRNA hairpins against Pgc1a or luciferase (Luc) as control. Four days later mRNA was prepared and gene expression was assessed by qPCR. Data are shown as mRNA levels relative to Rsp18 expression, expressed as mean±SEM. *P<0.05 compared to corresponding shLuc expressing control group. FIG. 4E shows the results of cortices harvested from either male five months old Pgc1a KO (Pgc1−/−) or wild type mice (Pgc1a+/+). mRNA was prepared and gene expression was assessed by qPCR. Data are shown as mRNA levels relative to Rsp18 expression, expressed as mean±SEM. *P<0.05 compared to wild type control group.

FIG. 6A shows the results of primary cortical neurons at DIV 7 transduced with either PGC-1α or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding GFP expressing control group. FIG. 6B shows the results of primary cortical neurons at DIV 7 treated with either XCT 790 (1 μM), a selective inverse ERRα agonist, DY131 (1 μM), a selective ERRβ and ERRγ agonist, or vehicle for overnight. mRNA was prepared and gene expression was assessed by qPCR. Data are shown as mRNA levels relative to Rsp18 expression, expressed as mean±SEM, *P<0.05 compared to vehicle only group. FIG. 6C shows the results of primary cortical neurons at DIV 4 transduced with lentivirus carrying shRNA hairpins against either Erra or luciferase (Luc) as control. Three days later cells were transduced with either PGC-1α or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding shLuc expressing control group. *P<0.05 compared to corresponding GFP expressing control group. FIG. 6D shows the results of analyzing the murine Fndc5 promoter for ERREs. The murine Fndc5 gene and 6 kb of its upstream promoter were searched for the canonical ERRE: TGA CCTT. Genomic coordinates are given according to the assembly mm9 from the UCSC Genome Browser. The bottom diagram indicates the degree of mammalian conservation across the genomic locus. The presented motif was modified from an online tool available on the World Wide Web at factorbook.org (Wang et al. (2012) *Genome Res.* 22, 1798-1812).

FIG. 7A shows the results of primary cortical neurons at DIV 7 transduced with either PGC-1α or GFP adenovirus. Forty-eight hours later mRNA was prepared and gene expression was assessed by qPCR. Data are shown as mRNA levels relative Rsp18 expression, expressed as mean±SEM. *P<0.05 compared to corresponding GFP expressing control group. FIG. 7B shows the results of primary cortical neurons at DIV 7 treated with either GW7647 (1 μM), a potent and highly selective PPARα agonist, GW0742 (1 μM), a potent and highly selective PPARδ or vehicle for overnight. mRNA was prepared and gene expression was assessed by qPCR. Data are shown as mRNA levels relative to Rsp18 expression, expressed as mean±SEM. *P<0.05 compared to vehicle only group. FIG. 7C shows the results of primary cortical neurons at DIV 4 transduced with lentivirus carrying shRNA hairpins against either Erra luciferase (Luc) as control. Three days later cells were transduced with either PGC-1α or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding shLuc expressing control group. $P<0.5 compared to corresponding GFP expressing control group.

FIG. 8A shows the results of primary cortical neurons at DIV 6 transduced with either FNDC5 or GFP adenovirus. Forty-eight hours later, cells were washed with PBS and plain neurobasal was added. Whole cell lysates and conditioned media were harvested the next day. Conditioned media was concentrated and deglycosylated. Samples were analyzed by immunoblotting. Intensity of unspecific bands and Ponceau staining were used to assess equal loading. deglyc.=deglycosylation. FIG. 8B shows the results of primary cortical neurons at DIV 7 transduced with either FNDC5 or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding GFP expressing control group. FIG. 8C shows the results of primary cortical neurons at DIV 5 transduced with lentivirus carrying the specified shRNA hairpins against Fndc5 or luciferase (Luc) as control. Four days later mRNA was prepared and gene expression was assessed by qPCR. Data are shown as mRNA levels relative to Rsp18 expression, expressed as mean±SEM. *P<0.05 compared to corresponding shLuc expressing control group. FIG. 8D shows the results of primary cortical neurons at DIV 7 transduced with either FNDC5 or GFP adenovirus. Three days later cell viability was assessed using the CellTiter-Glo® Luminescent Cell Viability Assay (Promega). Data are expressed as mean±SEM and shown as fold compared to GFP expressing control group. *P<0.05 compared to the GFP expressing control group. AU=arbitrary unit. FIG. 8E shows the results of primary cortical neurons at DIV 5 transduced with lentivirus carrying the specified shRNA hairpins against Fndc5 or luciferase (Luc) as control. Three days later cell viability was assessed using the CellTiter-Glo® Luminescent Cell Viability Assay (Promega). Data are expressed as mean±SEM and shown as fold compared to the shLuc expressing control group. *P<0.05 compared to the shLuc expressing control group. AU=arbitrary unit. FIG. 8F shows the results of primary cortical neurons at DIV 7 stimulated with human recombinant BDNF at the indicated concentrations or vehicle for overnight. mRNA was prepared and gene expression was assessed by qPCR. Data are shown as mRNA levels relative to Rsp18 expression, expressed as mean±SEM. *P<0.05 compared to vehicle only group. FIG. 8G shows the results of primary cortical neurons at DIV 7 stimulated with the indicated recombinant neurotrophins and growth factors (100 ng/ml) for overnight. mRNA was prepared and gene expression was assessed by qPCR. Data are shown as mRNA levels relative to Rsp18 expression, expressed as mean±SEM. *P<0.05 compared to vehicle only group. FIG. 8H shows the results of primary cortical neurons at DIV 6 treated either with the TrkB inhibitor K252a (50 nM) or vehicle. Twenty-four hours later human recombinant BDNF (100 ng/ml) or vehicle was added for overnight stimulation. mRNA was prepared and gene expression was assessed by qPCR. Data are shown as mRNA levels relative Rsp18 expression, expressed as mean±SEM. *P<0.05 compared to vehicle only group.

FIGS. 9A-9C shows the results of five week old male wild-type BALB/c mice injected with GFP- or FNDC5-expressing adenoviral particles intravenously. Animals were sacrificed seven days later and inguinal/subcutaneous fat pads (WAT=while adipose tissues) (FIG. 9A), hippocampus (FIG. 9B), and forebrain (FIG. 9C) were collected. mRNA was prepared, and gene expression was assessed by qPCR. Data are shown as mRNA levels relative to Rsp18 expression, expressed as mean±SEM. *P<0.05 compared to wild type control group. FIG. 9D shows a model of the hippocampal PGC-1α/FNDC5/BDNF pathway in exercise. Endurance exercise increases hippocampal Fndc5 gene expression through a PGC-1α/Errα transcriptional complex. This elevated Fndc5 gene expression stimulates in turn Bdnf gene expression. BDNF is the master regulator of nerve cell survival, differentiation and plasticity in the brain. This will lead to improved cognitive function, learning and memory, which are known beneficial effects of exercise on the brain.

FIG. 11A shows the results of primary hippocampal neurons isolated from C57/Bl6 wild type E17 embryos and cultured in vitro. At the indicated days in vitro (DIV) mRNA was prepared and gene expression was assessed by qPCR. Data are shown as mRNA levels relative to Rsp18 expression, expressed as mean±SEM. *P<0.05 compared to DIV 1 control group. FIG. 11B shows the results of primary hippocampal neurons at DIV 7 transduced with either PGC-1α or GFP adenovirus. Forty-eight hours later mRNA was prepared and gene expression was assessed by qPCR. Data are shown as mRNA levels relative to Rsp18 expression, expressed as mean±SEM. *P<0.05 compared to corresponding GFP expressing control group. FIG. 11C shows the results of primary hippocampal neurons at DIV 5 transduced with lentivirus carrying the specified shRNA hairpin against Pgc1a or luciferase (Luc) as control. Four days later mRNA was prepared and gene expression was assessed by qPCR. Data are shown as mRNA levels relative to Rsp18 expression, expressed as mean±SEM. *P<0.05 compared to corresponding shLuc expressing control group. FIG. 11D shows the results of primary hippocampal neurons at DIV 5 and 6 stimulated with recombinant irisin (1 ug/ml). mRNA was prepared twenty-four hours and gene expression was assessed by qPCR. Data are shown as mRNA levels relative to Rsp18 expression, expressed as mean±SEM. *P<0.05 compared to vehicle only group. FIG. 11A shows the results of primary hippocampal neurons at DIV 5 transduced with lentivirus carrying the specified shRNA hairpins against Fndc5 or luciferase (Luc) as control. Four days later mRNA was prepared and gene expression was assessed by qPCR. Data are shown as mRNA levels relative to Rsp18 expression, expressed as mean±SEM. *P<0.05 compared to corresponding shLuc expressing control group. FIG. 11F shows the results of primary hippocampal neurons at DIV 7 stimulated with recombinant BDNF (100 ng/ml) for overnight. mRNA was prepared and gene expression was assessed by qPCR. Data are shown as mRNA levels relative to Rsp18 expression, expressed as mean±SEM. *P<0.05 compared to vehicle only group.

Figure 1:
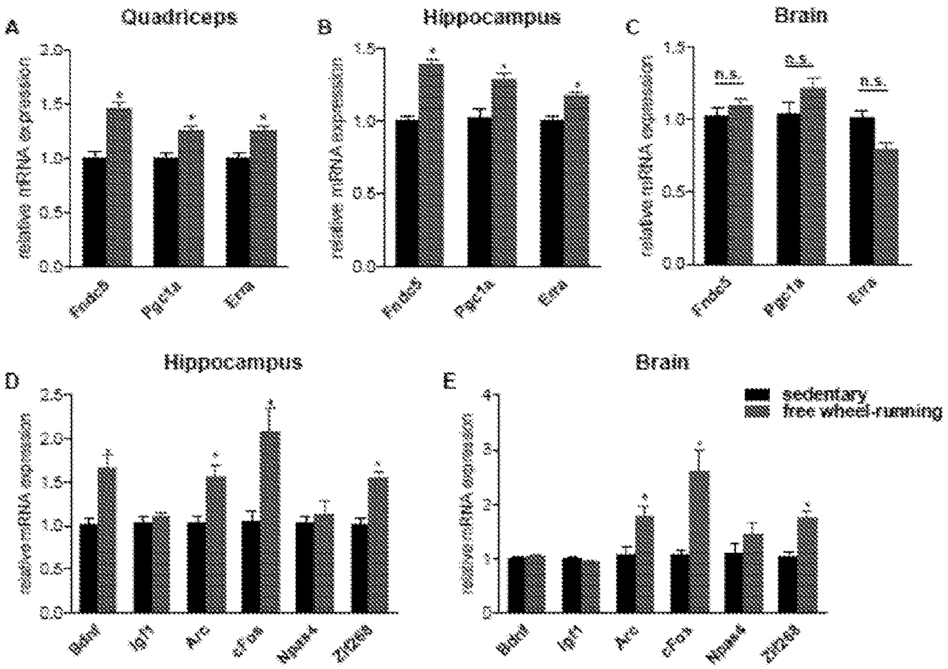
FIGS. 1A-1E shows that endurance exercise induces hippocampal Fndc5 gene expression.

For every figure described herein depicting box plots, the order of displayed boxes from top to bottom in the box plot legend corresponds to the boxes in the box plot in order from left to right.

DETAILED DESCRIPTION OF THE INVENTION

The present invention is based in part on the discovery that Fndc5 or irisin polypeptide, or fragments thereof, can act on neurons of the central and/or peripheral nervous system to enhance BDNF expression/activity and increase neuronal survival and function to thereby prevent or treat undesired neurological disorders.

In order that the present invention may be more readily understood, certain terms are first defined. Additional definitions are set forth throughout the detailed description.

As used herein, the term "administering" a substance, such as a therapeutic entity to an animal or cell" is intended to refer to dispensing, delivering or applying the substance to the intended target. In terms of the therapeutic agent, the term "administering" is intended to refer to contacting or dispensing, delivering or applying the therapeutic agent to an animal by any suitable route for delivery of the therapeutic agent to the desired location in the animal, including delivery by either the parenteral or oral route, intramuscular injection, subcutaneous/intradermal injection, intravenous injection, buccal administration, transdermal delivery and administration by the intranasal or respiratory tract route.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "BDNF" refers to brain-derived neurotrophic factor and is a neurotrophin. The term, "neurotrophins" refers to a class of structurally related growth factors that promote neural survival and differentiation. They stimulate neurite outgrowth, suggesting that they can promote regeneration of injured neurons, and act as target-derived neurotrophic factors to stimulate collateral sprouting in target tissues that produce the neurotrophin (Korsching (1993) *J. Neurosci.* 13:2739). Brain-derived neurotrophic factor (BDNF) was initially characterized as a basic protein present in brain extracts and capable of increasing the survival of dorsal root ganglia (Leibrock et al. (1989) *Nature* 341:149). When axonal communication with the cell body is interrupted by injury, Schwann cells produce neurotrophic factors such as nerve growth factor (NGF) and BDNF. Neurotrophins are released from the Schwann cells and dispersed diffusely in gradient fashion around regenerating axons, which then extend distally along the neurotrophins' density gradient (Ide (1996) *Neurosci. Res.* 25:101). Local application of BDNF to transected nerves in neonatal rats has been shown to prevent massive death of motor neurons that follows axotomy (DiStefano et al. (1992) *Neuron,* 8:983; Oppenheim et al. (1992) *Nature* 360:755; and Yan et al. (1992) *Nature* 360:753). The mRNA titer of BDNF increases to several times the normal level four days after axotomy and reaches its maximum at 4 weeks (Meyer et al. (1992) *J. Cell Biol.* 119:45). Moreover, BDNF has been reported to enhance the survival of cholinergic neurons in culture (Nonomura et al. (1995) *Brain Res.* 683:129). In addition, nucleic acid and polypeptides sequences of BDNF orthologs in numerous species are well known in the art and include human BDNF (NM_001143805.1, NP_001137277.1, NM_001143806.1, NP_001137278.1, NM_001143807.1, NP_001137279.1, NM_001143808.1, NP_001137280.1, NM_001143809.1, NP_001137281.1, NM_001143810.1, NP_001137282.1, NM_001143811.1, NP_001137283.1, NM_001143812.1, NP_001137284.1, NM_001143813.1, NP_001137285.1, NM_001143814.1, NP_001137286.1, NM_001143815.1, NP_001137287.1, NM_001143816.1, NP_001137288.1, NM_001709.4, NP_001700.2, NM_170731.4, NP_733927.1, NM_170732.4, NP_733928.1, NM_170733.3, NP_733929.1, NM_170734.3, NP_733930.1, NM_170735.5. and NP_733931.1), chimpanzee BDNF (NM_001012441.1 and NP_001012443.1), monkey BDNF (XM_001089568.2 and XP_001089568.2), dog BDNF (NM_001002975.1 and NP_001002975.1), cow BDNF (NM_001046607.2 and NP_001040072.1), mouse BDNF (NM_001048139.1, NP_001041604.1, NM_001048141.1, NP_001041606.1, NM_001048142.1, NP_001041607.1, NM_007540.4, and NP_031566.4), rat BDNF (NM_001270630.1, NP_001257559.1, NM_001270631.1, NP_001257560.1, NM_001270632.1, NP_001257561.1, NM_001270633.1, NP_001257562.1, NM_001270634.1, NP_001257563.1, NM_001270635.1, NP_001257564.1, NM_001270636.1, NP_001257565.1, NM_001270637.1, NP_001257566.1, NM_001270638.1, NP_001257567.1, NM_012513.4, and NP_036645.2), chicken BDNF (NM_101031616.1 and NP_001026787.1), and zebrafish BDNF (NM_1131595.2 and NP_571670.2). In addition, numerous anti-BDNF antibodies having a variety of characterized specificities and suitabilities for various immunochemical assays are commercially available and well known in the art, including antibody pa1014 from Boster Immunoleader, antibody BDNF-#9 from DSHB Iowa, antibody 209-401-C27 from Rockland, antibody BML-SA665 from Enzo Life Sciences, antibody EB08117 from Everest Biotech, antibody AHP1831 from AbD Serotec, antibody ANT-010 from Alomone, and the like.

The term "binding" or "interacting" refers to an association, which may be a stable association, between two molecules, e.g., between a polypeptide of the invention and a binding partner, due to, for example, electrostatic, hydrophobic, ionic and/or hydrogen-bond interactions under physiological conditions. Exemplary interactions include protein-protein, protein-nucleic acid, protein-small molecule, and small molecule-nucleic acid interactions.

The term "biological sample" when used in reference to a diagnostic assay is intended to include tissues, cells and biological fluids isolated from a subject, as well as tissues, cells and fluids present within a subject.

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

As used herein, the terms "neurological diseases" or "neurological disorders" refers to a host of undesirable conditions affecting neurons in the brain of a subject. Representative examples of such conditions include, without limitation, Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders. As used herein, the term "movement disorder" includes neurological diseases or disorders that involve the motor and movement systems, resulting in a range of abnormalities that affect the speed, quality and ease of movement. Movement disorders are often caused by or related to abnormalities in brain structure and/or function. Movement disorders include, but are not limited to (i) tremors: including, but not limited to, the tremor associated with Parkinson's Disease, physiologic tremor, benign familial tremor, cerebellar tremor, rubral tremor, toxic tremor, metabolic tremor, and senile tremor; (ii) chorea, including, but not limited to, chorea associated with Huntington's Disease, Wilson's Disease, ataxia telangiectasia, infection, drug ingestion, or metabolic, vascular or endocrine etiology (e.g., chorea gravidarum or thyrotoxicosis); (iii) ballism (defined herein as abruptly beginning, repetitive, wide, flinging movements affecting predominantly the proximal limb and girdle muscles); (iv) athetosis (defined herein as relatively slow, twisting, writhing, snakelike movements and postures involving the trunk, neck, face and extremities); (v) dystonia (defined herein as a movement disorder consisting of twisting, turning tonic skeletal muscle contractions, most, but not all of which are initiated distally); (vi) paroxysmal choreoathetosis and tonic spasm; (vii) tics (defined herein as sudden, behaviorally related, irregular, stereotyped, repetitive movements of variable complexity); (viii) tardive dyskinesia; (ix) akathesia, (x) muscle rigidity, defined herein as resistance of a muscle to stretch; (xi) postural instability; (xii) bradykinesia; (xiii) difficulty in initiating movements; (xiv) muscle cramps; (xv) dyskinesias and (xvi) myoclonus.

As used herein, the term "neurodegenerative disease" or "neurodegenerative disorder" encompass a subset of neurological diseases characterized by involving a progressive loss of neurons or loss of neuronal function. Accordingly, the term "neurodegeneration" refers to the progressive loss or function of at least one neuron or neuronal cell. The ordinarily skilled artisan will appreciate that the term "progressive loss" can refer to cell death or cell apoptosis. The ordinarily skilled artisan would further appreciate that "neuronal cell loss" refers to the loss of neuronal cells. The loss of neuronal cells may be a result of a genetic predisposition, congenital dysfunction, apoptosis, ischemic event, immune-mediated, free-radical induced, mitochondrial dysfunction, lesion formation, misregulation or modulation of a central nervous system-specific pathway or activity, chemical induced, or any injury that results in a loss of neuronal cells, as well as a progressive loss of neuronal cells. Thus, a neurodegenerative disorder or neurodegenerative disease, as used in the current context, includes any abnormal physical or mental behavior or experience where the death of neuronal cells is involved in the etiology of the disorder, or is affected by the disorder. As used herein, neurodegenerative diseases encompass disorders affecting the central and peripheral nervous systems, and include such afflictions as memory loss, stroke, dementia, personality disorders, gradual, permanent or episodic loss of muscle control. Examples of neurodegenerative disorders or diseases for which the current invention can be used preferably include, but are not limited to, Alzheimer's Disease, Parkinson's Disease, Huntington's Disease, amyotrophic lateral sclerosis (ALS), Pick's disease, prion diseases, dystonia, dementia with Lewy bodies, multiple system atrophy, progressive supranuclear palsy, Friedreich's Ataxia, temporal lobe epilepsy, stroke, traumatic brain injury, mitochondrial encephalopathies, Guillain-Barre syndrome, multiple sclerosis, epilepsy, myasthenia gravis, chronic idiopathic demyelinating disease (CID), neuropathy, ataxia, dementia, chronic axonal neuropathy and stroke.

As used herein, the term "neuronal" or "neuron" refers to one or more cells that are a morphologic and functional unit of the brain, spinal column, and peripheral nerves consisting of nerve cell bodies, dendrites, and axons. Neuronal cell types can include, but are not limited to, typical nerve cell body showing internal structure, horizontal cell from cerebral cortex, Martinotti cell, bipolar cell, unipolar cell, Purkinje cell, and pyramidal cell of motor area of cerebral cortex. Exemplary neuronal cells can include, but are not limited to, cholinergic, adrenergic, noradrenergic, dopaminergic, serotonergic, glutaminergic, GABAergic, and glycinergic.

The term "treatment," as used herein, is defined as the application or administration of a therapeutic agent to a patient, or application or administration of a therapeutic agent to an isolated tissue or cell line from a patient, who has a disease or disorder, a symptom of a disease or disorder or a predisposition toward a disease or disorder, with the purpose of curing, healing, alleviating, relieving, altering, remedying, ameliorating, improving or affecting the disease or disorder, the symptoms of disease or disorder or the predisposition toward a disease or disorder. A therapeutic agent includes, but is not limited to, polypeptides, small molecules, peptides, peptidomimetics, nucleic acid molecules, antibodies, ribozymes, siRNA molecules, and sense and antisense oligonucleotides described herein As used herein, the terms "Fndc5" and "Frcp2" refer to fibronectin type III domain containing 5 protein and are intended to include fragments, variants (e.g., allelic variants) and derivatives thereof. The nucleotide and amino acid sequences of mouse Fndc5, which correspond to Genbank Accession number NM_027402.3 and NP_081678.1 respectively, are set forth in SEQ ID NOs: 1 and 2. At least three splice variants encoding distinct human Fndc5 isoforms exist (isoform 1, NM_001171941.2, NP_001165412.1; isoform 2, NM_153756.2, NP_715637.1; and isoform 3, NM_001171940.1, NP_001165411). The nucleic acid and polypeptide sequences for each isoform is provided herein as SEQ ID NOs: 3-8, respectively. Nucleic acid and polypeptide sequences of FNDC5 orthologs in organisms other than mice and human are well known and include, for example, chimpanzee FNDC5 (XM_003949350.1, XP_003949399.1, XM_001155446.3, and XP_001155446.3), monkey FNDC5 (XM_001098747.2 and XP_001098747.2), worm FNDC5 (XM_544428.4 and XP_544428.4), rat FNDC5 (XM_002729542.3 and XP_002729588.2), chicken FNDC5 (XM_417814.2; XP_417814.2), and zebrafish FNDC5 (XM_001335368.1; XP_001335404.1). In addition, numerous anti-BDNF antibodies having a variety of characterized specificities and suitabilities for various immunochemical assays are commercially available and well known in the art, including antibody LS-C166197 from Lifespan Biosciences, antibodies AG-25B-0027 and -0027B from Adipogen, antibody HPA051290 from Atlas Antibodies, antibodies PAN576Hu71 and Hu01 and Hu02 and Mu01 from Usen Lifesciences, antibody AP18024PU-N from Acris Antibodies, antibody OAAB05345 from Aviva Systems Biology, antibody CPBT-33932RH from Creative Biomart, antibody orb39441 from Biorbyt, antibody ab93373 from Abcam, antibody NBP2-14024 from Novus Biologicals, antibody F4216-25 from United States Biological, antibody AP8746b from Abgent, and the like.

In some embodiments, fragments of Fndc5 having one or more biological activities of the full-length Fndc5 protein are described and employed. Such fragments can comprise or consist of at least one fibronectin domain of an Fndc5 protein without containing the full-length Fndc5 protein sequence. In some embodiments, Fndc5 fragments can comprise or consist of a signal peptide, extracellular, fibronectin, hydrophobic, and/or C-terminal domains of an Fndc5 protein without containing the full-length Fndc5 protein sequence. As further indicated in the Examples, Fndc5 orthologs are highly homologous and retain common structural domains well known in the art. In other embodiments, the term "irisin" refers to the fragment representing residues 29 or 30 to 140 of SEQ ID NO: 2 or the corresponding residues in an FNDC5 ortholog thereof.

TABLE 1

Mouse Fndc5 cDNA Sequence

SEQ ID NO: 1 atg acc aca ggg ccg tga gcc tgg ccg acc cgc gcc gcg ctc cgc ctg tgg cta ggc tgc gtc tgc ttc gag ctg gtg cag gag gaa agc cac tca gcc cat gtg aac gtg acc gtc cgg cac ctc aag gcc aac tct gcc gtg gtc agc tgg gat gtc ctg gag gat gaa gtg gtc att ggc ttt gcc atc tct cag cag aag aag gat gtg cgg atg ctc cgg ttc att cag gag gtg aac acc acc acc cgg tcc tgc gct ctc tgg gac ctg gag gag gac aca gaa tat atc gtc cat gtg cag gcc atc tcc atc cag gga cag agc cca gcc agt gag act gtg ctc ttc aag acc cca cgc gag gct gaa aag atg gcc tca aag aac aaa gat gag Gtg acc atg aag gag atg ggg agg aac cag cag ctg cga acg (ggg) gag gtg ctg atc att gtt gtg gtc ctc ttc atg tgg gca ggt gtt ata gct ctc ttc tgc cgc cag tat gat atc Atc aag gac aac gag ccc aat aaa aaa aag gag aaa acc aag agc gca tca gaa acc agc Aca ccg gag cat cag ggt ggg ggt ctc ctc cgc agc aag ata tga Mouse Fndc5 Amino Acid Sequence

SEQ ID NO: 2

M P P G P C A W P P R A A L R L W L G C V C F A L V Q A D S P S A P V N

V T V R H L K A N S A V V S W D V L E D E V V I G F A I S Q Q K K D V R

M L R F I Q E V N T T T R S C A L W D L E E D T E Y I V H V Q A I S I Q

G Q S P A S E P V L F K T P R E A E K M A S K N K D E V T M K E M G R N

Q Q L R T G E V L I I V V V L F M W A G V I A L F C R Q Y D I I K D N E

P N N N K E K T K S A S E T S T P E H Q G G G L L R S K I

Human Fndc5 (isoform 1) cDNA Sequence

SEQ ID NO: 3

1 atgctgcgct tcatccagga ggtgaacacc accacccgct catgtgccct ctgggacctg 61 gaggaggata cggagtacat agtccacgtg caggccatct ccattcaggg ccagagccca 121 gccagcgagc ctgtgctctt caagaccccg cgtgaggctg agaagatggc ctccaagaac 181 aaagatgagg taaccatgaa agagatgggg aggaaccaac agctgcggac aggcgaggtg 241 ctgatcatcg tcgtggtcct gttcatgtgg gcaggtgtca ttgccctctt ctgccgccag 301 tatgacatca tcaaggacaa tgaacccaat aacaacaagg aaaaaaccaa gagtgcatca 361 gaaaccagca caccagagca ccagggcggg ggcttctcc gcagcaaggt gagggcaaga 421 cctgggcctg ggtgggccac cctgtgcctc atgctctggt aa TABLE 1-continued Human Fndc5 (isoform 1) Amino Acid Sequence

SEQ ID NO: 4

1 mlrfigevnt ttrscalwdl eedteyivhv qaisiqgqsp asepvlfktp reaekmaskn 61 kdevtmkemg raqqlrtgev liivvvlfmw agvialfcrq ydiikdnepn nnkektksas 121 etstpehqgg gllrskvrar pgpgwatlcl mlw Human Fndc5 (isoform 2) cDNA Sequence

SEQ ID NO: 5

1 atgctgcgct tcatccagga ggtgaacacc accacccgct catgtgccct ctgggacctg 61 gaggaggata cggagtacat agtccacgtg caggccatct ccattcaggg ccagagccca 121 gccagcgagc ctgtgctctt caagaccccg cgtgaggctg agaagatggc ctccaagaac 181 aaagatgagg taaccatgaa agagatgggg aggaacaaac agctgcggac aggcgaggtg 241 ctgatcatcg tcgtggtcct gttcatgtgg gcaggtgtca ttgccctctt ctgccgccag 301 tatgacatca tcaaggacaa tgaacccaat aacaacaagg aaaaaaccaa gagtgcatca 361 gaaaccagca caccagagca ccagggcggg gggcttctcc gcagcaagat atga Human Fndc5 (isoform 2) Amino Acid Sequence

SEQ ID NO: 6

1 mlrfiqevnt ttrscalwdl eedteyivhv qaisiqgqsp asepvlfktp reaekmaskn 61 kdevtmkemg rnqqlrtgev liivvvlfmw agvialfcrq ydiikdnepn nnkektksas 121 etstpehqgg gllrski Human Fndc5 (isoform 3) cDNA Sequence

SEQ ID NO: 7

1 atgctgcgct tcatccagga ggtgaacacc accacccgct catgtgccct ctgggacctg 61 gaggaggata cggagtacat agtccacgtg caggccatct ccattcaggg ccagagccca 121 gccagcgagc ctgtgctctt caagaccccg cgtgaggctg agaagatggc ctccaagaac 181 aaagatgagg taaccatgaa agagatgggg aggaaccaac agctgcggac aggcgaggtg 241 ctgatcatcg tcgtggtcct gttcatgtgg gcaggtgtca ttgccctctt ctgccgccag 301 tatgacatca ttgaagcgtg a Human Fndc5 (isoform 3) Amino Acid Sequence

SEQ ID NO: 8

1 mlrfiqevnt ttrscalwdl eedteyivhv qaisiqgqsp asepvlfktp reaekmaskn 61 kdevtmkemg rnqqlrtgev liivvvlfmw agvialfcrq ydiiea Chicken Fndc5 cDNA Sequence

SEQ ID NO: 9

1 atggagaaga acagggacgg acgcggcacc cctggtgtcc atctggggat ggagaaggaa 61 gatgatttag agcccggtga cacgccgggg ctgcgcgaag ccctggtggc gagatgtcac 121 cgctgacgcg cacccgccgg gggtatcacc gggacgggac cogtttgctc cttccggcga 181 tggggagcgg tccgggccga gggctcccgg tcccgcctgg gggaaactga ggcagacggc 241 ggggccgggc ggggcggggg ccgagccgcc cccgggccgg gggagggacc ggagcggggc 301 tgaccagagc tgcagcgggc ggagccgggg ctaggcgggg ccgcctcccg gccgagccga 361 gccgaaccga gacgcgctgc cgagggccgc cgagcccgaa gccgcccccg gccgaaccgg 421 gcggcccagc cggttccggg ccccggagct ctccgcggtg ctgaacggcg ccgccgagcc 481 agagggacga cggccacgga gaggctaggc ccaggcgcgg agcggagggc cgcgggggga

541 tggagccctt cctgggctgc accggcgccg cgctcctgct ctgctttcag ctacgccggt 601 ctgcggccgg tggaggcaga cagcccttcg gctccggtca atgtcacagt caaacacctg 661 aaggcaaact cagctgtagt gacttgggac gttctggagg atgaagttgt cattggattt 721 gccatttccc agcagaagaa ggacgtgcgg atgctgcgct tcatccagga ggtgaacacc TABLE 1-continued

```
 781   accacccgct cctgtgccct ctgggaccta gaggaggaca ctgagtacat tgtgcatgtc

 841   caggccatca gcatccaagg ccagagccct gccagtgagc cagtcctctt caagaccccc

 901   agggaagctg agaaactggc ttctaaaaat aaagatgagg tgacaatgaa ggagatggcg

 961   aagaaaaacc aacagctgcg cgcaggggaa atactcatca ttgtggtggt gttgtttatg

1021   tgggcagggg tgatcgccct gttctgcagg cagtacgaca tcatcaaaga caacgagccg

1081   aacaacagca aggagaaagc caagagcgcc tcagagaaca gcaccaccga gcaccagggt

1141   ggggggctgc tccgcagcaa gttcccaaaa aacaaaccct cagtgaacat cattgaggca

1201   taa
```

Chicken Fndc5 Amino Acid Sequence

SEQ ID NO: 10

```
   1   meknrdgrgp pgvhlgmeke ddlepgdtpg lrealvarch rcrapagglt gtgpvcsfrr

  61   wgavraegsr srlgeteadg gagrgggraa pgpgegperg apalgraepg lggaasrpsr

 121   aepsraaegr rarsrprpnr aappvpgpga lrgaerrrra rgtpaperlg pgaarraagg

 181   wspswaapap rscsafsyag lrpveadsps apvnvtvkhl kansavvtwd vledevvigf

 241   aisqgkkdvr mlrfigevnt ttrscalwdl eedteyivhv qaisigggsp asepvifktp

 301   reaeklaskn kdevtmkema kknggglrage iliivvvlfm wagvialfcr qydlikdnep

 361   nnskekaksa senstpebgg ggllrsktpk nkpsvniiea
```

Zebrafish Fndc5 cDNA Sequence

SEQ ID NO: 11

```
   1   atgagttctt acagtttggc agctccagtg aatgtgtcca tcagggatct gaagagcagc

  61   tcagccgtgg tgacatggga cacgccagac ggagagccag tcatcggctt cgccatcaca

 121   caacagaaga aagatgtccg catgctgcgc tttattcaag aagtgaacac caccacgcgg

 181   agctgtgcat tgtgggatct ggaagctgat acggattaca ttgtgcacgt tcagtctatc

 241   agcataagcg gggcgagtcc tgttagtgaa gctgtgcact tcaagacccc gacagaagtt

 301   gaaacacagg cctccaagaa caaagacgag gtgacgatgg aggaggtcgg gccgaacgct

 361   cagctcaggg coggagagtt catcattatt gtggtggtcc tcatcatgtg ggcaggtgtg

 421   atcgcactat tctgccgtca gtatgacatc attaaagaca acgaaccaaa caataacaag

 481   gataaagcca agaactcgtc tgaatgcagc actccagagc acacgtcagg tggcctgctg

 541   cgcagtaagg tataa
```

Zebrafish Fndc5 Amino Acid Sequence

SEQ ID NO: 12

```
   1   mssyslaapv nvsirdlkss savvtwdtpd gepvigfait qqkkdvrmlr fiqevntttr

  61   scalwdlead tdyivhvqsi sisgaspvse avhfktptev etqasknkde vtmeevgpna

 121   qlragefiii vvvlimwagv ialfcrqydi ikdnepnnnk dkaknssecs tpehtsggll

 181   rskv
```

Fragment of Murine Fndc5 Nucleic Acid Sequence that encodes amino acid residues 29-140 of murine Fndc5

SEQ ID NO: 13

```
 104                                                  gacagcc cctcagcccc

 121   tgtgaacgtg accgtccggc acctcaaggc caactctgcc gtggtcagct gggatgtcct

 181   ggaggatgaa gtggtcattg gctttgccat ctctcagcag aagaaggatg tgcggatgct

 241   ccggttcatt caggaggtga acaccaccac ccggtcctgc gctctctggg acctggagga

 301   ggacacagaa tatatcgtcc atgtgcaggc catctccatc cagggacaga gcccagccag
```

TABLE 1-continued

```
361   tgagcctgtg ctcttcaaga ccccacgcga ggctgaaaag atggcctcaa agaacaaaga

421   tgaggtgacc atgaaggag
```

Murine Fndc5 (residues 29-140)

SEQ ID NO: 14

```
DSPSAPVNVTVRHLKANSAVVSWDVLEDEVVIGFAISQQKKDVRMLRFIQEVNTTT

RSCALWDLEEDTEYIVHVQAISIQGQSPASEPVLFKTPREAEKMASKNKDEVTMKE
```

Frament of Human Fndc5 Nucleic Acid Sequence

SEQ ID NO: 15

```
161                                           gacagtccct cagccccagt

181   gaacgtcacc gtcaggcacc tcaaggccaa ctctgcagtg gtgagctggg atgttctgga

241   ggatgaggtt gtcatcggat ttgccatctc ccagcagaag aaggatgtgc ggatgctgcg

301   cttcatccag gaggtgaaca ccaccacccg ctcatgtgcc ctctgggacc tggaggagga

361   tacggagtac atagtccacg tgcaggccat ctccattcag ggccagagcc cagccagcga

421   gcctgtgctc ttcaagaccc cgcgtgaggc tgagaagatg gcctccaaga acaaagatga

481   ggtaaccatg aaagag
```

It will be appreciated that specific sequence identifiers (SEQ ID NOs) have been referenced throughout the specification for purposes of illustration and should therefore not be construed to be limiting. Any marker of the invention, including, but not limited to, the markers described in the specification and markers described herein (e.g., BDNF, Pgc1 alpha, Npas4, Err alpha, cFos, Zrc, Zif268, and the like), are well known in the art and can be used in the embodiments of the invention.

I. Screening Assays

Methods (also referred to herein as a "screening assay") are provided for identifying enhancers of the expression or activity of Fndc5 or irisin, or fragments thereof, i.e., candidate or test compounds or agents (e.g., polypeptides, peptides, peptidomimetics, small molecules (organic or inorganic) or other drugs) which promote BDNF expression. Compounds identified using assays described herein may be useful for modulating BDNF expression or activity, e.g., increasing BDNF expression or activity. Thus, these compounds would be useful for treating or preventing neurological diseases or disorders as BDNF is an important neuroregulator of neuron survival.

These assays are designed to identify agents that replicate the function of Fndc5 or irisin, fragments thereof, bind to or interact with such a protein, or bind to or interact with other intracellular or extracellular proteins that interact with such a protein. Such compounds may include, but are not limited to peptides, antibodies, nucleic acid molecules, siRNA molecules, or small organic or inorganic compounds. Such compounds may also include other cellular proteins.

Agents identified via assays such as those described herein may be useful, for example, increasing BDNF expression or activity or activity-induced gene expression in the central and/or peripheral nervous system and, for example, increasing neuronal survival, decreasing lesion formation, increasing neurite growth and/or synapses, decreasing mitochondrial dysfunction, increasing neuronal differentiation, modulating neuronal migration, increasing dendritic arborization, increasing synaptic plasticity. Thus, these compounds would be useful for treating or preventing a neurological disease or disorder, particularly neurodegenerative diseases or disorders. In some embodiments, increased activity or expression of Fndc5 or irisin, fragments thereof, would bring about an effective increase in the level of BDNF protein activity, thus identifying, treating or preventing neurological diseases or disorders. For example, a partial agonist or an agonist administered in a dosage or for a length of time to increase expression or activity of Fndc5 or irisin, or fragments thereof would act to increase neuronal survival, decrease lesion formation, increase neurite outgrowth and/or synapses, increase mitochondrial function, and treat or prevent a neurological disease or disorder.

In one embodiment, the invention provides assays for screening candidate or test compounds which are substrates of or interact with Fndc5 or irisin, or fragments thereof. In another embodiment, the invention provides assays for screening candidate or test compounds which bind to or modulate the activity of Fndc5 or irisin, or fragments thereof. In still another embodiment, the invention provides assays for screening candidate Fndc5 or irisin proteins, or fragments thereof, having desired functional characteristics. The test agents of the present invention can be obtained using any of the numerous approaches in combinatorial library methods known in the art, including: biological libraries, spatially addressable parallel solid phase or solution phase libraries; synthetic library methods requiring deconvolution; the 'one-bead one-compound' library method; and synthetic library methods using affinity chromatography selection. The biological library approach is limited to polypeptide or peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993)

*Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell, such as a neuron, is contacted with a test agent, such as an Fndc5 or irisin polypeptide, or fragments thereof, and the ability of the test compound to modulate BDNF expression or activity is determined. Determining the ability of the test agent to modulate BDNF expression or activity can be accomplished by monitoring, for example, neuronal survival, BDNF expression levels, the level of transcription of genes downstream of BDNF, and the like. The cell can be of mammalian origin, e.g., a neuron.

The ability of the test agent to modulate the binding of Fndc5 or irisin polypeptide, or fragments thereof, to a substrate such as a modulator of BDNF expression (e.g., NPas4 or other upstream gene or protein) can also be determined. Determining the ability of the test agent to modulate such binding can be accomplished, for example, by coupling the substrate with a radioisotope or enzymatic label such that binding of the substrate to Fndc5 or irisin polypeptide, or fragments thereof can be determined by detecting the labeled substrate in a complex. The Fndc5 or irisin polypeptide, fragments thereof, can also be coupled with a radioisotope or enzymatic label to monitor the ability of a test agent to modulate binding to the substrate in a complex. Determining the ability of the test agent to bind Fndc5 or irisin polypeptide, or fragments thereof, can be accomplished, for example, by coupling the agent with a radioisotope or enzymatic label such that binding of the agent to Fndc5 or irisin polypeptide, or fragments thereof, can be determined by detecting the labeled agent in a complex. For example, such agents can be labeled with $^{125}I$, $^{35}S$, $^{14}C$, or $^{3}H$, either directly or indirectly, and the radioisotope detected by direct counting of radioemmission or by scintillation counting. Agents can further be enzymatically labeled with, for example, horseradish peroxidase, alkaline phosphatase, luciferase, and the enzymatic label detected by determination of conversion of an appropriate substrate to product.

It is also within the scope of the present invention to determine the ability of an agent to interact with Fndc5 or irisin polypeptide, or fragments thereof, or with a modulator BDNF expression or activity, without the labeling of any of the interactants. For example, a microphysiometer can be used to detect the interaction without labeling any component (McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS).

In another embodiment, modulators of BDNF expression are identified in a method wherein a cell is contacted with a candidate agent, such as Fndc5 or irisin polypeptide, or fragments thereof, and the expression of BDNF mRNA or protein in the cell is determined. The level of expression of BDNF mRNA or protein in the presence of the candidate agent is compared to the level of expression of BDNF mRNA or protein in the absence of the candidate agent. When expression of BDNF mRNA or protein is greater (statistically significantly greater) in the presence of the candidate agent than in its absence, the candidate agent is identified as a stimulator of BDNF mRNA or protein expression. The level of BDNF mRNA or protein expression in the cells can be determined by methods described herein for detecting BDNF mRNA or protein.

In some embodiments, the assays can be conducted in cell-free formats using known components of BDNF gene expression (e.g., Npas4). It may be desirable to immobilize certain components of the assay, such as the Fndc5 or irisin polypeptide, or fragments thereof and such embodiments may benefit from the use of well-known adaptations for biomolecule immobilization, such as the use of microtiter plates, beads, test tubes, micro-centrifuge tubes in combination with derivatizable moieties, such as fusion protein domains, biotinylzation, antibodies, and the like.

The present invention further pertains to novel agents identified by the above-described screening assays. Accordingly, it is within the scope of this invention to further use an agent identified as described herein in an appropriate animal model.

Any of the compounds, including but not limited to compounds such as those identified in the foregoing assay systems, may be tested for a compound capable of treating or preventing a neurological disease or disorder comprising the ability of the compound to modulate BDNF nucleic acid expression or BDNF polypeptide activity, thereby identifying a compound capable of treating or preventing a neurological disease or disorder. Cell-based and animal model-based assays for the identification of compounds exhibiting such an ability to treat or prevent a neurological disease or disorder described herein.

In one aspect, cell-based systems, described herein, may be used to identify agents such as an Fndc5 or irisin polypeptide, or fragments thereof, that modulate BDNF nucleic acid expression or BDNF polypeptide activity or treat neurological diseases or disorders. For example, such cell systems may be exposed to an agent at a sufficient concentration and for a time sufficient to elicit such an amelioration of disease symptoms in the exposed cells. After exposure, the cells are examined to determine whether one or more of the disease phenotypes, e.g., neuronal survival, for example, has been altered to resemble a more normal or more wild type disease phenotype.

In addition, animals or animal-based disease systems, such as those described herein, may be used to identify such agents. Such animal models may be used as test substrates for the identification of drugs, pharmaceuticals, therapies, and interventions which may be effective in modulating PGC-1α, treating or preventing neurological diseases or disorders. In some embodiments, the parameters of the assay are defined to allow for systemic or serum expression of the agent to cross the blood-brain barrier.

Additionally, gene expression patterns may be utilized to assess the ability of a compound to modulate BDNF expression or activity. Thus, these compounds would be useful for treating, preventing, or assessing a neurological disease or disorder. For example, the expression pattern of one or more genes may form part of a "gene expression profile" or "transcriptional profile" which may be then be used in such an assessment. "Gene expression profile" or "transcriptional profile", as used herein, includes the pattern of mRNA expression obtained for a given tissue or cell type wider a given set of conditions. Gene expression profiles may be generated, for example, by utilizing a differential display procedure. Northern analysis and/or RT-PCR. Gene expression profiles may be characterized for known states within the cell- and/or animal-based model systems. Subsequently, these known gene expression profiles may be compared to ascertain the effect a test compound has to modify such gene expression profiles, and to cause the profile to more closely resemble that of a more desirable profile. For example, useful markers are described herein and include, without limitation, markers of mitochondrial function such as LDH2, Ndufb5, COX6a1, and ATP5j, markers of neuronal activity, such as immediate early genes, NF-H, NF-M, MOBP, ATPa1, and ATP1a2, upstream and downstream regulators of BDNF gene expression, and the like.

II. Methods of Treatment

The present invention provides for both prophylactic and therapeutic methods of treating or preventing a neurological disease or disorder in a subject, e.g., a human, at risk of (or susceptible to) a neurological disease or disorder, by administering to said subject an enhancer of BDNF expression or activity, such as Fndc5 or irisin polypeptide, or fragments thereof, such that the neurological disease or disorder is treated or prevented. In some embodiments, which includes both prophylactic and therapeutic methods, the BDNF modulator is administered by in a pharmaceutically acceptable formulation.

With regard to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers to the study of how a patient's genes determine his or her response to a drug (e.g., a patient's "drug response phenotype", or "drug response genotype").

Thus, another aspect of the invention provides methods for tailoring a subject's prophylactic or therapeutic treatment with either Fndc5 or irisin polypeptide, or fragments thereof, or other BDNF modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

A. Prophylactic Methods

In one aspect, the present invention provides a method for treating or preventing a neurological disease or disorder by administering to a subject an agent which modulates BDNF expression or activity in the central and/or peripheral nervous system using an Fndc5 or irisin polypeptide, or fragments thereof, or an enhancer of such a polypeptide's expression or activity. The present invention also provides methods for modulating neuronal survival, formation of brain lesions, neurodegeneration, and/or neurite/synapse growth in the subject. Subjects at risk for a neurological disease or disorder can be identified by, for example, any or a combination of the diagnostic or prognostic assays described herein. Administration of a prophylactic agent can occur prior to the manifestation of symptoms characteristic of a neurological disease or disorder, such that the neurological disease or disorder or symptom thereof, e.g., neuronal cell death, is prevented or, alternatively, delayed in its progression.

B. Therapeutic Methods

The present invention provides methods for modulating BDNF expression or activity in the central and/or peripheral nervous system in a subject by administering an agent which modulates BDNF expression or activity in the central and/or peripheral nervous system using an Fndc5 or irisin polypeptide/nucleic acid, or fragments thereof, or an enhancer of such a polypeptide/nucleic acid expression or activity. In one embodiment, BDNF expression or activity is increased by administering an inducer or agonist of BDNF expression or activity, thereby modulating modulating neuronal survival, formation of brain lesions, neurodegeneration, and/or neurite/synapse growth in the subject.

Accordingly, another aspect of the invention pertains to methods of modulating BDNF expression or activity for therapeutic purposes and for use in treatment of neurological diseases or disorders. In an exemplary embodiment, the modulatory method of the invention involves contacting a cell with an Fndc5 or irisin polypeptide, or fragments thereof, or an enhancer of such a polypeptide's or nucleic acid's expression or activity. In one embodiment, the agent simulates one or more activities of an Fndc5 or irisin polypeptide, or fragments thereof, or an enhancer of such a polypeptide's expression or activity. Examples of such simulator agents include small molecule agonists and mimetics, e.g., a peptidomimetic. These modulatory methods can be performed in vitro or ex vivo (e.g., by culturing the cell with the agent) or, alternatively, in vivo (e.g., by administering the agent to a subject). In one embodiment, the method involves administering an agent (e.g., an agent identified by a screening assay described herein), or combination of agents that modulate BDNF expression or activity or are otherwise useful for treating or preventing neurological diseases or disorders, such as neurotrophic factors, free radical inhibitors, and the like.

Increasing BDNF expression or activity leads to treatment or prevention of a neurological disease or disorder, therefore providing a method for treating, preventing, and assessing a neurological disease or disorder. A variety of techniques may be used to increase the expression, synthesis, or activity of BDNF using an Fndc5 or irisin polypeptide, or fragments thereof, or an enhancer of such a polypeptide's expression or activity.

For example, an Fndc5 or irisin polypeptide/nucleic acid, or fragments thereof, or an enhancer of such a polypeptide/nucleic acid expression or activity protein may be administered to a subject. Any of the techniques discussed below may be used for such administration. One of skill in the art will readily know how to determine the concentration of effective, non-toxic doses of the protein, utilizing techniques such as those described below.

Additionally, nucleic acid sequences, such as RNA sequences encoding such proteins may be directly administered to a subject, at a concentration sufficient to produce a level of an Fndc5 or irisin polypeptide, or fragments thereof, or an enhancer of such a polypeptide's expression or activity, such that BDNF expression or activity in the peripheral and/or central nervous system is modulated. Any of the techniques discussed below, which achieve intracellular administration of compounds, such as, for example, liposome administration, may be used for the administration of such nucleic acid molecules. RNA molecules may be produced, for example, by recombinant techniques such as those described herein. Other pharmaceutical compositions, medications, or therapeutics may be used in combination with the agents described herein. Further, subjects may be treated by gene replacement therapy. For example, one or more copies of an Fndc5 or irisin polypeptide, or fragments thereof, or an enhancer of such a polypeptide's expression or activity, may be inserted into cells using vectors which include, but are not limited to adenovirus, adeno-associated virus, and retrovirus vectors, in addition to other particles that introduce DNA into cells, such as liposomes. Additionally, techniques such as those described above may be used for the introduction of desired gene sequences into human cells. Furthermore, expression or activity of transcriptional activators which act upon BDNF may be increased to thereby increase expression and activity of BDNF. Small molecules enhance the expression or activity of an Fndc5 or irisin polypeptide, or fragments thereof, either directly or indirectly may also be used.

Cells, preferably, autologous cells, containing PGC-1α expressing gene sequences may then be introduced or reintroduced into the subject. Such cell replacement techniques may be preferred, for example, when the gene product is a secreted, extracellular gene product.

C. Pharmaceutical Compositions

The methods of the invention involve administering to a subject an agent which modulates BDNF expression or activity in the central and/or peripheral nervous system in a subject by administering an agent which modulates BDNF expression or activity in the central and/or peripheral nervous system using an Fndc5 or irisin polypeptide, or fragments thereof, or an enhancer of such a polypeptide's expression or activity, either alone or in combination with other agents useful for treating or preventing an undesirable neurological disorder or condition.

The agents which modulate BDNF expression or activity can be administered in a therapeutically effective amount to a subject using pharmaceutical compositions suitable for such administration. Such compositions typically comprise the agent (e.g., nucleic acid molecule or protein) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "effective amount" of an agent that induces expression and/or activity of Fndc5 is that amount necessary or sufficient to modulate (e.g., increase or decrease) expression and/or activity of Fndc5 in the subject or population of subjects. The effective amount can vary depending on such factors as the type of therapeutic agent(s) employed, the size of the subject, or the severity of the disorder.

The term "therapeutically effective amount" as used herein means that amount of an agent that modulates (e.g., enhances) the expression or activity of Fndc5 or irisin, or fragments thereof, or composition comprising an agent that modulates (e.g., enhances) such expression or activity, which is effective for producing some desired therapeutic effect, e.g., BDNF expression in the central and/or peripheral nervous system, at a reasonable benefit/risk ratio.

A pharmaceutical composition used in the therapeutic methods of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the agent that modulates BDNF activity (e.g., Fndc5 or irisin polypeptide, or fragments thereof, or an enhancer of such a polypeptide's expression or activity) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents that modulate BDNF expression or activity can also be prepared in the form of suppositories (e.g., with conventional suppository bases such as cocoa butter and other glycerides) or retention enemas for rectal delivery.

In one embodiment, the agents that modulate BDNF expression or activity are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for case of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the agent that modulates PGC-1α activity and the particular therapeutic effect to be achieved, and the limitations inherent in the art of compounding such an agent for the treatment of subjects.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio L50/ED50. Agents which exhibit large therapeutic indices are preferred. While agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage for use in humans. The dosage of such BDNF modulating agents lies preferably within a range of circulating concentrations that include the ED50 with little or no toxicity. The dosage may vary within this range depending upon the dosage form employed and the route of administration utilized. For any agent used in the therapeutic methods of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with a polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grains per mole, organic or inorganic compounds having a molecular weight less than about 5,000 grams per mole, organic or inorganic compounds having a molecular weight less than about 1,000 grams per mole, organic or inorganic compounds baying a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal. (e.g., a human) in order to modulate expression or activity of a BDNF molecule, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated, e.g., the intended use of the agonist or antagonize.

Further, the BDNF modulating agents described herein can be conjugated to additional therapeutic moieties of interest, such as a growth factor, intracellular targeting domain, and the like, that are well known in the art. The conjugates of the invention can be used for modifying a given biological response, the drug moiety is not to be consulted as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

The nucleic acid molecules used in the methods of the invention can be inserted into vectors and used as gene therapy vectors. Gene therapy vectors can be delivered to a subject by for example, intravenous injection, local administration (see U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Any means for the introduction of a polynucleotide into mammals, human or non-human or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am Respir Cell Mol Biol 10:24-29, 1994; Tsan et al. Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vector, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777, 127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant Fndc5 polypeptides, and fragments thereof, can be administered to subjects. In some embodiments, fusion proteins can be constructed and administered which have enhanced biological properties (e.g., Fc fusion proteins discussed above). In addition, the Fndc5 polypeptides, and fragment thereof, can be modified according to well known pharmacological methods in the art (e.g., pegylation, glycosylation, oligomerization, etc.) in order to further enhance desirable biological activities, such as increased bioavailability and decreased proteolytic degradation.

III. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the levels of protein and/or nucleic acid expression or activity of a BDNF and/or Fndc5 or irisin polypeptide, or fragments thereof, in the context of a biological sample (e.g., blood, serum, fluid, e.g., cerebrospinal fluid, spinal fluid, cells, or tissue, e.g., neural tissue) to thereby determine whether an individual is afflicted with a neurological disease or disorder neurological disease or disorder has a risk of developing a neurological disease or disorder. The invention also provides for prognostic (or predictive) assays for determining whether an individual is at risk of developing a neurological disease or disorder.

One particular embodiment includes a method for assessing whether a subject is afflicted with a neurological disease or disorder or is at risk of developing a neurological disease or disorder comprising detecting the expression or activity of the Fndc5 or irisin polypeptide, or fragments thereof in a cell or tissue sample of a subject, wherein a decrease in the expression or activity thereof indicates the presence of a neurological disease or disorder or the risk of developing a neurological disease or disorder in the subject. In this embodiment, subject samples tested are, for example, cerebrospinal fluid, spinal fluid, and neural tissue.

Another aspect of the invention pertains to monitoring the influence of modulators of BDNF expression in clinical trials.

These and other agents are described in further detail in the following sections.

A. Prognostic and Diagnostic Assays

To determine whether a subject is afflicted with a neurological disease or disorder has a risk of developing, a neurological disease or disorder, a biological sample may be obtained from a subject and the biological sample may be contacted with a compound or an agent capable of detecting an Fndc5 or irisin polypeptide, or fragments thereof, or nucleic acid (e.g., mRNA or genomic DNA) that encodes such a protein, in the biological sample. A preferred agent for detecting the mRNA or genomic DNA is a labeled nucleic acid probe capable of hybridizing to the mRNA or genomic DNA. The nucleic acid probe can be, for example, a sequence that is complementary to an Fndc5 or irisin nucleic acid set forth in Table 1, or a portion thereof, such as an oligonucleotide of at least 15, 20, 25, 30, 25, 40, 45, 50, 100, 250 or 500 nucleotides in length and sufficient to specifically hybridize under stringent conditions to the desired mRNA or genomic DNA. Other suitable probes for use in the diagnostic assays of the invention are described herein.

The term "biological sample" is intended to include tissues, cells, and biological fluids isolated from a subject, as well as tissues, cells, and fluids present within a subject, e.g., cerebrospinal fluid, spinal fluid, and neural tissue. That is, the detection method of the invention can be used to detect mRNA, protein, or genomic DNA of Fndc5 or irisin, or portions thereof, in a biological sample in vitro as well as in vivo. For example, in vitro techniques for detection of mRNA include Northern hybridizations and in situ hybridizations. In vitro techniques for detection of protein include enzyme linked immunosorbent assays (ELISAs), Western blots, immunoprecipitations and immunofluorescence. In vitro techniques for detection of genomic DNA include Southern hybridizations. Furthermore, in vivo techniques for detection of protein include introducing into a subject a labeled antibody against the desired protein to be detected. For example, the antibody can be labeled with a radioactive marker whose presence and location in a subject can be detected by standard imaging techniques.

In another embodiment, the methods further involve obtaining a control biological sample from a control subject, contacting the control sample with a compound or agent capable of detecting protein, mRNA, or genomic DNA, such that the presence of the desired protein, mRNA or genomic DNA is detected in the biological sample, and comparing the presence of the protein, mRNA or genomic DNA in the control sample with the presence of the protein, mRNA or genomic DNA in the rest sample.

Analysis of one or more polymorphic regions of Fndc5 or irisin nucleic acids, or fragments thereof in a subject can be useful for predicting whether a subject has or is likely to develop a neurological disease or disorder. In preferred embodiments, the methods of the invention can be characterized as comprising detecting, in a sample of cells from the subject, the presence or absence of a specific allelic variant of one or more polymorphic regions of the gene, such as a premature truncation that does not encode a biologically active protein or a mutation in the stop codon or other region that prevents protein access across the blood-brain barrier. The allelic differences can be: (i) a difference in the identity of at least one nucleotide or (ii) a difference in the number of nucleotides, which difference can be a single nucleotide or several nucleotides. The invention also provides methods for detecting differences in an Fndc5- or irisin-encoding gene such as chromosomal rearrangements, e.g., chromosomal dislocation. The invention can also be used in prenatal diagnostics.

A preferred detection method is allele specific hybridization using probes overlapping the polymorphic site and having about 5, 10, 20, 25, or 30 nucleotides around the polymorphic region. In a preferred embodiment of the invention, several probes capable of hybridizing specifically to allelic variants are attached to a solid phase support e.g., a "chip". Oligonucleotides can be bound to a solid support by a variety of processes, including lithography. For example, a chip can hold up to 250,000 oligonucleotides (GeneChip, Affymetrix). Mutation detection analysis using, these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment. For example, the identity of the allelic variant of the nucleotide polymorphism in the 5' upstream regulatory element can be determined in a single hybridization experiment.

In other detection methods, it is necessary to first amplify at least a portion of nucleic acid prior to identifying the allelic variant. Amplification can be performed, e.g., by PCR and/or LCR (see Wu and Wallace, (1989) *Genomics* 4:560), according to methods known in the art. In one embodiment, genomic DNA of a cell is exposed to two PCR primers and amplification for a number of cycles sufficient to produce the required amount of amplified DNA. In preferred embodiments, the primers are located between 150 and 350 base pairs apart.

Alternative amplification methods include: self sustained sequence replication (Guatelli, J. C. et al., 1990, *Proc. Natl. Acad. Sci. USA* 87:1874-1878), transcriptional amplification system (Kwoh, D. Y. 1989, *Proc. Natl. Acad. Sci. USA* 86:1173-1177), Q-Beta Replicase (Lizardi, P. M. et al., 1988, *Bio/Technology* 6:1197), and self-sustained sequence replication (Guatelli et al., (1989) *Proc. Nat. Acad. Sci.* 87:1874), and nucleic acid based sequence amplification (NABSA), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment, any of a variety of sequencing reactions known in the art can be used to directly sequence at least a portion of an Fndc5- or irisin-encoding gene, or portion thereof, and detect allelic variants, e.g., mutations, by comparing the sequence of the sample sequence with the corresponding reference (control) sequence. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci.* 74:5463). It is also contemplated that any of a variety of automated sequencing procedures may be utilized when performing the subject assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled "DNA Sequencing by Mass Spectrometry Via Exonuclease Degradation" by H. Köster), and U.S. Pat. No. 5,605,798 and International Patent Application No. PCT/US96/03651 entitled DNA Diagnostic's Based on Mass Spectrometry by H. Köster; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA sequencing employing a mixed DNA-polymer chain probe" and U.S. Pat. No. 5,571,676 entitled "Method for mismatch-directed in vitro DNA sequencing".

In some cases, the presence of a specific allele of an Fndc5- or irisin-encoding gene in DNA from a subject can be shown by restriction enzyme analysis. For example, a specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (Myers, et al. (1985) *Science* 230:1242). In general, the technique of "mismatch cleavage" starts by providing heteroduplexes formed by hybridizing a control, nucleic acid, which is optionally labeled, e.g., RNA or DNA, comprising a nucleotide sequence of an PGC-1α allelic variant with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing, polyacrylamide gels to determine whether the control and sample nucleic acids have an identical nucleotide sequence or in which nucleotides they are different. See, for example, Cotton et al. (1988) *Proc. Acad Sci USA* 85:4397 Saleeba et al. (1992) *Methods Enzymol.* 217:286-295. In a preferred embodiment, the control or sample nucleic acid is labeled for detection.

In another embodiment, an allelic variant can be identified by denaturing high-performance liquid chromatography (DHPLC) (Oefner and Underhill, (1995) *Am. J. Human Gen.* 57:Suppl. A266). DHPLC uses reverse-phase ion-pairing chromatography to detect the heteroduplexes that are generated during amplification of PCR fragments from individuals who are heterozygous at a particular nucleotide locus within that fragment (Oefner and Underhill (1995) *Am. J. Human Gen.* 57:Suppl. A266). In general, PCR products are produced using PCR primers flanking the DNA of interest. DHPLC analysis is carried out and the resulting chromatograms are analyzed to identify base pair alterations or deletions based on specific chromatographic profiles (see O'Donovan et al. (1998) *Genomics* 52:44-49).

In other embodiments, alterations in electrophoretic mobility is used to identify the type of desired allelic variant. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat Res* 285:125-144; and Hayashi (1992) *Genet Anal Tech. Appl* 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the identity of an allelic variant of a polymorphic region is obtained by analyzing the movement of a nucleic acid comprising the polymorphic region in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) *Biophys Chem* 265:1275).

Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) *Nature* 324:163); Saiki et al (1989) *Proc. Natl Acad. Sci USA* 86:6230; and Wallace et al. (1979) *Nucl. Acids Res.* 6:3543). Such allele specific oligonucleotide hybridization techniques may be used for the simultaneous detection of several nucleotide changes in different polylmorphic regions of Fndc5- or irisin-encoding genes. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238, Newton et al. (1989) *Nucl. Acids Res.* 17:2503). This technique is also termed "PROBE" for Probe Oligo Base Extension. In addition, it may be desirable to introduce a novel restriction site in the region of the mutation to create cleavage-based detection (Gasparini et al. (1992) *Mol Cell Probes* 6:1).

In another embodiment, identification of the allelic variant is carried out using an oligonucleotide ligation assay (OLA), as described, e.g., in U.S. Pat. No. 4,998,617 and Landegren, U. et al., (1988) *Science* 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., (1990) *Proc. Natl. Acad. Sci.* (*U.S.A.*) 87:8923-8927. In this method, PCR is used to achieve the exponential amplification of target DNA, which is then detected using OLA.

Several techniques based on this OLA method have been developed and can be used to detect specific allelic variants of a polymorphic region of an PGC-1α gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) *Nucleic Acids Res* 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in an Fndc5- or irisin-encoding gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each subject. Several methods have been developed to facilitate the analysis of such single nucleotide polymorphisms.

In one embodiment, the single base polymorphism can be detected by using a specialized exonuclease-resistant nucleotide, as disclosed, in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide presents in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site (Cohen, D. et al. (French Patent 2,650,840; PCT Application No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA is described by Goelet, P. et al. (PCT Application No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Several primer-guided nucleotide incorporation procedures for assaying polymorphic sites in DNA have been described (Komher, J. S. et al., *Nucl. Acids. Res.* 17:7779-7784 (1989), Sokolov, B. P., *Nucl. Acids Res.* 18:3671 (1990), Syvanen, A.-C., et al., *Genomics* 8:684-692 (1990); Kuppuswamy, M. N. et al., Proc. Natl. Acad. Sci. (U.S.A.) 88:1143-1147 (1991); Prezant, T. R. et al., *Hum. Mutat.* 1:159-164 (1992); Ugozzoli, L. et al., *GATA* 9:107-112 (1992); Nyren, P. et al., *Anal. Biochem.* 208:171-175 (1993)). These methods differ from GBA in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., *Amer. J. Hum. Genet.* 52:46-59 (1993)).

For determining the identity of the allelic variant of as polymorphic region located in the coding region of an Fndc5- or irisin-encoding gene, yet other methods than those described above can be used. For example, identification of an allelic variant which encodes a mutated protein can be performed by using an antibody specifically recognizing the mutant protein in, e.g., immunohistochemistry or immunoprecipitation. Antibodies to wild-type Fndc5 or irisin, or fragment thereof, or mutated forms of such proteins can be prepared according to methods known in the art.

Alternatively, one can also measure an activity of a BDNF or Fndc5 or irisin polypeptide, or fragments thereof, such as the ability to cross the blood-brain barrier, to enhance BDNF expression, to bind to neurons, and the like. Binding assays are known in the art and involve, e.g., obtaining cells from a subject, and performing binding experiments with a labeled lipid, to determine whether binding to the mutated form of the protein differs from binding to the wild-type of the protein.

Antibodies directed against reference or mutant BDNF or Fndc5 or irisin polypeptides, or fragments thereof can also be used in disease diagnostics and prognostics. Such antibodies are well known in the art (see, for example, antibody LS-C166197 from Lifespan Biosciences, antibody AG-25B-0027 from Adipogen, antibody HPA051290 from Atlas Antibodies, antibody PAN576Hu02 from Uscn Lifesciences, antibody AP18024PU-N from Acris Antibodies, antibody OAAB05345 from Aviva Systems Biology, antibody CPBT-33932RH from Creative Biomart, antibody Orb39441 from Biorbyt, and antibody NBP2-14024 from Novus Biologicals). In addition, such diagnostic methods, may be used to detect abnormalities in the level of such polypeptide expression, or abnormalities in the structure and/or tissue, cellular, or subcellular location of such polypeptides. Structural differences may include, for example, differences in the size, electronegativity, or antigenicity of the mutant polypeptide relative to the normal polypeptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al. 1989, supra, at Chapter 18. The protein detection and isolation methods employed herein may also be such as those described in Harlow and Lane, for example (Harlow, E. and Lane, D., 1988, “Antibodies: A Laboratory Manual”, Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of Fndc5 or irisin polypeptide, or fragments thereof. In situ detection may be accomplished by removing a histological specimen from a subject, and applying thereto a labeled antibody of the present invention. The antibody (or fragment) is preferably applied by overlaying the labeled antibody (or fragment) onto a biological sample. Through the use of such a procedure, it is possible to determine not only the presence of the Fndc5 or irisin polypeptide, or fragments thereof, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an antibody is via linkage to an enzyme and use in an enzyme immunoassay (EIA) (Voller, "The Enzyme Linked Immunosorbent Assay (ELISA)", *Diagnostic Horizons* 2:1-7, 1978, Microbiological Associates Quarterly Publication, Walkersville, Md.; Voller, et al., *J. Clin. Pathol.* 31:507-520 (1978); Butler, *Meth. Enzymol.* 73:482-523 (1981); Maggio, (ed.) *Enzyme Immunoassay*, CRC Press Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate, dehydrogenase, those phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the Chemiluminescent-tagged antibody is then determined by detecting the presence of luminescence that arises during the course of a chemical reaction. Examples of particularly useful chemiluminescent labeling compounds are luminol, isoluminal, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

If a polymorphic region is located in an exon, either in a coding or non-coding portion of the gene, the identity of the allelic variant can be determined by determining the molecular structure of the mRNA, pre-mRNA, or cDNA. The molecular structure can be determined using any of the above described methods for determining the molecular structure of the genomic DNA.

The methods described herein may be performed, for example, by utilizing pre-packaged diagnostic kits, such as those described above, comprising at least one probe or primer nucleic acid described herein, which may be conveniently used, e.g., to determine whether a subject has or is at risk of developing a disease associated with a specific allelic variant of interest. Sample nucleic acid to be analyzed by any of the above-described diagnostic and prognostic methods can be obtained from any cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of subject tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

B. Monitoring of Effects During Clinical Trials

The present invention further provides methods for determining the effectiveness of a BDNF modulator (e.g., an FNDC5 polypeptide/nucleic acid, or fragment thereof) in treating or preventing a neurological disease or disorder or assessing risk of developing a neurological disease or disorder in a subject. For example, the effectiveness of such a modulator in increasing BDNF gene expression, protein levels can be monitored in clinical trials of subjects. In such clinical trials, the expression or activity of an Fndc5 gene, BDNF gene, or other genes that have been implicated in, for example, a BDNF expression pathway can be used as a "read out" or marker of the phenotype of a particular cell.

For example, and not by way of limitation, genes, including BDNF, that are modulated in cells by treatment with an agent that modulates Fndc5 expression or activity can be identified. Thus, to study the effect of agents which modulate BDNF expression or activity in subjects suffering from or at risk of developing a neurological disease or disorder, or agents to be used as a prophylactic, for example, a clinical trial, cells can be isolated and RNA prepared and analyzed for the levels of expression of BDNF and other genes implicated in BDNF activity or expression. The levels of gene expression (e.g., a gene expression pattern) can be quantified by Northern blot analysis or RT-PCR, as described herein, or alternatively by measuring the amount of protein produced, by one of the methods described herein, or by measuring the levels of activity of BDNF or other genes, such as the BDNF regulator, Npas4. In this way, the gene expression pattern can serve as a marker, indicative of the physiological response of the cells to the agent which modulates BDNF expression or activity. This response state may be determined before, and at various points during treatment of the individual with the agent which modulates BDNF expression or activity In a preferred embodiment, the present invention provides a method for monitoring the effectiveness of treatment of a subject with an agent which modulates BDNF expression or activity (e.g., an agonist, antagonist, peptidomimetic, protein, peptide, nucleic acid, siRNA, or small molecule identified by the screening assays described herein) including the steps of (i) obtaining a pre-administration simple from a subject prior to administration of the agent, preferably a sample from the central or peripheral nervous system; (ii) detecting the level of expression of a BDNF protein, mRNA, or genomic DNA in the pre-administration sample; (iii) obtaining, one or more post-administration samples from the subject; (iv) detecting the level of expression or activity of the BDNF protein, mRNA, or genomic DNA in the post-administration samples; (v) comparing the level of expression or activity of the BDNF protein, mRNA, or genomic DNA in the pre-administration sample with the BDNF protein, mRNA, or genomic DNA in the post administration sample or samples; and (vi) altering the administration of the agent to the subject accordingly. For example, increased administration of the agent may be desirable to increase the expression or activity of BDNF to higher levels than detected, i.e., to increase the effectiveness of the agent. According to such an embodiment, BDNF expression or activity may be used as an indicator of the effectiveness of an agent, even in the absence of an observable phenotypic response.

IV. Isolated Nucleic Acids, Polypeptides, Antibodies, Vectors, and Host Cells Useful for the Methods Described Herein Nucleic acids, polypeptides, vectors, and host cells related to Fndc5 or irisin, or fragments thereof, are useful for carrying out the methods described herein.

Isolated nucleic acid molecules that encode Fndc5 or irisin, or biologically alive portions thereof, are well known in the art. As used herein, the term "nucleic acid molecule" is intended to include DNA molecules cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated Fndc5 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a brown adipocyte). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g. a nucleic acid molecule having, the nucleotide sequence of SEQ ID NO: 1, 3, 5, 7, 9, 11, 13 and 15 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NOs: 1, 3, 5, 7, 9, 11, 13 and 15 or a portion thereof (i.e., 100, 200, 300, 400, 450, 500, or more nucleotides), can be isolated using standard molecular biology techniques and the sequence information provided herein. For example, a human Fndc5 cDNA can be isolated from a human muscle cell line (from Stratagene, LaJolla, Calif., or Clontech, Palo Alto, Calif.) using all or portion of SEQ ID NOs: 1, 3, 5, 7, 9, 11, 13 or 15, or fragment thereof, as a hybridization probe and standard hybridization techniques (i.e., as described in Sambrook, Fritsh, E. F., and Maniatis, T. *Molecular Cloning: A Laboratory Manual, 2nd, ed., Cold Spring Harbor Laboratory*, Cold Spring Harbor Laboratory Press, Cold Spring Harbor, N.Y., 1989). Moreover, a nucleic acid molecule encompassing or a portion of SEQ ID NOs: 1, 3, 5, 7, 9, 11, 13 or 15 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NOs: 1, 3, 5, 7, 9, 11, 13 or 15, or fragment thereof, can be isolated by the polymerase chain reaction using oligonucleotide primers designed based upon the sequence of SEQ ID NOs: 1, 3, 5, 7, 9, 11, 13 or 15, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NOs: 1, 3, 5, 7, 9, 11, 13 or 15, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an Fndc5 nucleotide sequence can be prepared by standard synthetic techniques, i.e., using an automated DNA synthesizer.

Probes based on the Fndc5 nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express an Fndc5 protein, such as by measuring, a level of an Fndc5-encoding nucleic acid in a sample of cells from a subject, i.e., detecting Fndc5 mRNA levels.

Nucleic acid molecules encoding other Fndc5 members and thus which have a nucleotide sequence which differs from the Fndc5 sequences of SEQ ID NOs: 1, 3, 5, 7, 9, 11, 13 or 15, or fragment thereof, are contemplated. Moreover, nucleic acid molecules encoding Fndc5 proteins from different species, and thus which have a nucleotide sequence which differs from the Fndc5 sequences of SEQ ID NOs: 1, 3 5, 7, 9, 11, 13 or 15 are also intended to be within the scope of the present invention. For example, rat or monkey Fndc5 cDNA can be identified based on the nucleotide sequence of a human and/or mouse Fndc5.

In one embodiment, the nucleic acid molecule(s) of the invention encodes a protein or portion thereof which includes an amino acid sequence which is sufficiently homologous to an amino acid sequence of SEQ ID NO: 2, 4, 6, 8, 10, 12 or 14, or fragment thereof, such that the protein or portion thereof modulates (e.g., enhance) one or more of the following biological activities: 1) BDNF expression in the central and/or peripheral nervous system; 2) activity-induced immediate-early gene expression in neurons; 3) neuronal survival; 4) neurological lesion formation; 5) neurite outgrowth; 6) synaptogenesis; 7) synaptic plasticity; 8) neuronal mitochondrial function; 9) dendritic arborization; 10) neuronal differentiation; and 11) neuronal migration.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO: 2, 4, 6, 8, 10, 12 or 14, or fragment thereof) amino acid residues to an amino acid sequence of SEQ ID NO: 2, 4, 6, 8, 10, 12 or 14, or fragment thereof, such that the protein or portion thereof modulates (e.g., enhance) one or more of the following biological activities: 1) BDNF expression in the central and/or peripheral nervous system; 2) activity-induced immediate-early gene expression in neurons; 3) neuronal survival; 4) neurological lesion formation; 5) neurite outgrowth; 6) synaptogenesis; 7) synaptic, plasticity; 8) neuronal mitochondrial function; 9) dendritic arborization; 10) neuronal differentiation; and 11) neuronal migration.

In another embodiment, the protein is at least about 50%, re tenthly at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO: 2, 4, 6, 8, 10, 12 or 14, or fragment thereof, or a fragment thereof.

Portions of proteins encoded by Fndc5 or irisin nucleic acid molecules are preferably biologically active portions of the Fndc5 or irisin protein. As used herein, the term "biologically active portion" is intended to include a portion, e.g., a domain/motif, of Fndc5 or irisin that has one or more of the biological activities of the full-length Fndc5 or irisin protein.

Standard binding assays, e.g., immunoprecipitations and yeast two-hybrid assays, as described herein, or functional assays, RNAi or overexpression experiments, can be performed to determine the ability of an Fndc5 or irisin protein or a biologically active fragment thereof to maintain a biological activity of the full-length Fndc5 or irisin protein.

The invention further encompasses nucleic acid molecules that differ from the nucleotide sequence shown in SEQ ID NO: 1, 3, 5, 7, 9, 11, 13 or 15, or fragment thereof due to degeneracy of the genetic code and thus encode the same Fndc5 or irisin protein as that encoded by the nucleotide sequence shown in SEQ ID NO: 1, 3, 5, 7, 9, 11, 13 or 15, for fragment thereof. In another embodiment, an isolated nucleic acid molecule of the invention has a nucleotide sequence encoding a protein having an amino acid sequence shown in SEQ ID NO: 2, 4, 6, 8, 10, 12 or 14, or fragment thereof, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO: 2, 4, 6, 8, 10, 12 or 14, or fragment thereof, or a fragment thereof, or differs by at least 1, 2, 3, 5 or 10 amino acids but not more than 30, 20, 15 amino acids from SEQ ID NO: 2, 4, 6, 8, 10, 12 or 14. In another embodiment, a nucleic acid encoding an Fndc5 or irisin polypeptide consists of nucleic acid sequence encoding a portion of a full-length Fndc5 or irisin fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of Fndc5 or irisin may exist within a population (e.g., a mammalian population, a human population). Such genetic polymorphism in the Fndc5 gene exist among individuals within a population due to natural allelic variation. As used herein, the terms "gene" and "recombinant gene" refer to nucleic acid molecules comprising an open reading frame encoding Fndc5 or irisin protein, preferably a mammalian, e.g., human, Fndc5 or irisin protein. Such natural variations can typically result in 1-5% variance in the nucleotide sequence of the Fndc5 gene. Any and all such nucleotide variations and resulting amino acid polymorphisms in Fndc5 that are the result of natural allelic variation and that do not alter the functional activity of Fndc5 or irisin are intended to be within the scope of the invention. Moreover, nucleic acid molecules encoding Fndc5 or irisin proteins from other species, and thus which have a nucleotide sequence which differs from the human or mouse sequences of SEQ ID NO: 1, 3, 5, or 7, are intended to be within the scope of the invention. Nucleic acid molecules corresponding to natural allelic variants and homologues of the human or mouse Fndc5 cDNAs of the invention can be isolated based on their homology to the human or mouse Fndc5 nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the Fndc5 sequence that may exist in the population, the skilled artisan will further appreciate that changes can be introduced by mutation into the nucleotide sequence of SEQ ID NO: 1, 3, 5, 7, 9, 11, 13 or 15, or fragment thereof, thereby leading to changes in the amino acid sequence of the encoded Fndc5 or irisin protein, without altering the functional ability of the Fndc5 or irisin protein. For example, nucleotide substitutions leading to amino acid substitutions at “non-essential” amino acid residues can be made in the sequence SEQ ID NO: 1, 3, 5, 7, 9, 11, 13 or 15, or fragment thereof. A “non-essential” amino acid residue is a residue that can be altered from the wild-type sequence of Fndc5 (e.g., the sequence of SEQ ID NO: 2, 6, 8, 10, 12 or 14, or fragment thereof) without altering the activity of Fndc5 or irisin, whereas an “essential” amino acid residue is required for Fndc5 or irisin activity. Other amino acid residues, however, (e.g., those that are not conserved or only semi-conserved between mouse and human) may not be essential for activity and thus are likely to be amenable to alteration without altering Fndc5 or irisin activity. Furthermore, amino acid residues that are essential for Fndc5 or irisin functions related to neurological disorders, but not essential for Fndc5 functions related to thermogenesis, gluconeogenesis, cellular metabolism, and the like are likely to be amenable to alteration.

Accordingly, another aspect of the invention pertains to nucleic acid molecules encoding Fndc5 or irisin proteins that contain changes in amino acid residues that are not essential for Fndc5 or irisin activity. Such Fndc5 or irisin proteins differ in amino acid sequence from SEQ ID NO: 2, 4, 6, 8, 10, 12 or 14, or fragment thereof yet retain at least one of the Fndc5 or irisin activities described herein. In one embodiment, the isolated nucleic acid molecule comprises a nucleotide sequence encoding a protein, wherein the protein lacks one or more Fndc5 or irisin domains (e.g., a fibronectin, extracellular, signal peptide, hydrophobic, and/or C-terminal domain).

“Sequence identity or homology”, as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100, For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified “loop out regions”, e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6, In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding an Fndc5 or irisin protein homologous to the protein of SEQ ID NO: 2, 4, 6, 8, 10, 12 or 14, or fragment thereof, can be created by introducing one or more nucleotide substitutions, additions or deletions into the nucleotide sequence of SEQ ID NO: 1, 3, 5, 7, 9, 11, 13 or 15, or fragment thereof, or a homologous nucleotide sequence such that one or more amino acid substitutions, additions or deletions are introduced into the encoded protein. Mutations can be introduced into SEQ ID NO: 1, 3, 5, 7, 9, 11, 13 or 15, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A “conservative amino acid substitution” is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alimine, valine, leucine, isoleucine, proline, phenylalanine, methionine, tryptophan), bet217-420ranched side chains e.g., threonine, valine, isoleucine) and aromatic side chains (e.g., tyrosine, phenylalanine, tryptophan histidine). Thus, a predicted nonessential amino acid residue in Fndc5 or irisin is preferably replaced with another amino acid residue from the same side chain family. Alternatively, in another embodiment, mutations can be introduced randomly along all or part of an Fndc5 coding sequence, such as by saturation mutagenesis, and the resultant mutants can be screened for an Fndc5 or irisin activity described herein to identify mutants that retain Fndc5 or irisin activity. Following mutagenesis of SEQ ID NO: 1, 3, 5, 7, 9, 11, 13 or 15, or fragment thereof, the encoded protein can be expressed recombinantly (as described herein) and the activity of the protein can be determined using, for example, assays described herein.

Fndc5 levels may be assessed by any of a wide variety of well known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, Fndc5 levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the Fndc5 mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to lose of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA genomic DNA encoding Fndc5. Other suitable probes for use in the diagnostic assays of the invention are described herein. Hybridization of an mRNA with the probe indicates that Fndc5 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array e.g., an Affymetrix™ gene chip array. A skilled artisan can readily adapt known mRNA detection methods for use in detecting the level of the Fndc5 mRNA expression levels.

An alternative method for determining the Fndc5 mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection in such methods, a cell or tissue sample is prepared/processed using known histological methods. The sample is then immobilized on a support, typically a glass slide, and then contacted with a probe that can hybridize to the Fndc5 mRNA.

As an alternative to making determinations based on the absolute Fndc5 expression level, determinations may be based on the normalized Fndc5 expression level. Expression levels are normalized by correcting the absolute Fndc5 expression level by comparing its expression to the expression of a non-Fndc5 gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of an Fndc5 or irisin protein can also be detected and/or quantified by detecting or quantifying the expressed polypeptide. The Fndc5 or irisin polypeptide can be detected and quantified by any of a number of means well known to those of skill in the art. These may include analytic biochemical methods such as electrophoresis, capillary electrophoresis, high performance chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express Fndc5 or irisin, or fragments thereof.

Also provided are soluble, purified and/or isolated forms of Fndc5 or irisin, or fragments thereof. Hereinafter, irisin and fragments thereof will be considered to be encompassed within the term "fragments of Fndc5."

In one aspect, an Fndc5 polypeptide may comprise a full-length Fndc5 amino acid sequence or a full-length Fndc5 amino acid sequence with 1 to about 20 conservative amino acid substitutions. Amino acid sequence of any Fndc5 polypeptide described herein can also be at least 50, 55, 60, 65, 70, 75, 80, 85, 90, 91, 92, 93, 94, 95, 96, 97, 98, 99, or 99.5% identical to an Fndc5 polypeptide sequence of interest, described herein, well known in the art, or a fragment thereof. In addition, any Fndc5 polypeptide, or fragment thereof, described herein has modulates (e.g., enhance) one or more of the following biological activities: 1) BDNF expression in the central and/or peripheral nervous system; 2) activity-induced immediate-early gene expression in neurons; 3) neuronal survival; 4) neurological lesion formation; 5) neurite outgrowth; 6) synaptogenesis; 7) synaptic plasticity; 8) neuronal mitochondrial function; 9) dendritic arborization; 10) neuronal differentiation; and 11) neuronal migration. In another aspect, the present invention contemplates a composition comprising an isolated Fndc5 polypeptide and less than about 25%, or alternatively 15%, of alternatively 5%, contaminating biological macromolecules of polypeptides.

The present invention further provides compositions related to producing, detecting, or characterizing an Fndc5 polypeptide, or fragment thereof, such as nucleic acids, vectors, host cells, and the like. Such compositions may serve as compounds that modulate an Fndc5 polypeptide's expression and/or activity, such as antisense nucleic acids.

In certain embodiments, an Fndc5 polypeptide of the invention may be a fusion protein containing a domain which increases its solubility and bioavailability and/or facilitates its purification, identification, detection, and/or structural characterization. Exemplary domains, include, for example, glutathione S-transferase (GST), protein A, protein G, calmodulin-binding peptide thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, an Fndc5 polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, Fndc5 polypeptides, or fragments thereof, are fused to an antibody (e.g., IgG 1, IgG2, IgG3, IgG4) fragment (e.g., polypeptides). Techniques for preparing these fusion proteins are known, and are described, for example, in WO 99/31241 and in Cosman et al. (2001) *Immunity* 14:123-133. Fusion to an Fc polypeptide offers the additional advantage of facilitating purification by affinity chromatography over Protein A or Protein G columns.

In still another embodiment, an Fndc5 polypeptide may be labeled with a fluorescent label to facilitate their detection, purification, or structural characterization. In an exemplary embodiment, an Fndc5 polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated Fndc5 proteins, and biologically active portions thereof, as well as peptide fragments suitable for use as immunogens to raise anti-Fndc5 antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of Fndc5 protein in which the protein is separated from cellular components of the cells in which it is naturally or recombinantly produced. In one embodiment, the language "substantially free of cellular material" includes preparations of Fndc5 protein having less than about 30% (by dry weight) of non-Fndc5 protein (also referred to herein as a "contaminating protein"), more preferably less than about 20% of non-Fndc5 protein, still more preferably less than about 10% of non-Fndc5 protein, and most preferably less than about 5% non-Fndc5 protein. When the Fndc5 protein or biologically active portion thereof is recombinantly produced, it is also preferably substantially free of culture medium, culture medium represents less than about 20%, more preferably less than about 10%, and most preferably less than about 5% of the volume of the protein preparation. The language "substantially free of chemical precursors or other chemicals" includes preparations of Fndc5 protein in which the protein is separated from chemical precursors or other chemicals which are involved in the synthesis of the protein. In one embodiment, the language "substantially free of chemical precursors or other chemicals" includes preparations of Fndc5 protein having less than about 30% (by dry weight) of chemical precursors of non-Fndc5 chemicals, more preferably less than about 20% chemical precursors of non-Fndc5 chemicals, still more preferably less than about 10% chemical precursors of non-Fndc5 chemicals, and most preferably less than about 5% chemical precursors of non-Fndc5 chemicals. In preferred embodiments, isolated proteins or biologically active portions thereof lack contaminating proteins from the same animal from which the Fndc5 protein is derived. Typically, such proteins are produced by recombinant expression of for example, a human Fndc5 protein in a nonhuman cell.

In preferred embodiments, the protein or portion thereof comprises an amino acid sequence which is sufficiently homologous to an amino acid sequence of SEQ ID NO: 2, 4, 6, 8, 10, 12 or 14, or fragment thereof, such that the protein or portion thereof maintains one or more of the following biological activities or, in complex, modulates (e.g., enhance) one or more of the following biological activities: 1) BDNF expression in the central and/or peripheral nervous system; 2) activity-induced immediate-early gene expression in neurons; 3) neuronal survival; 4) neurological lesion formation; 5) neurite outgrowth; 6) synaptogenesis; 7) synaptic plasticity; 8) neuronal mitochondrial function; 9) dendritic arborization; 10) neuronal differentiation; and 11) neuronal migration. The portion of the protein is preferably a biologically active portion as described herein. In another preferred embodiment, the Fndc5 protein has an amino acid sequence shown in SEQ ID NO: 2, 4, 6, 8, 10, 12 or 14, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 2, 4, 6, 8, 10, 12 or 14, or fragment thereof. In yet another preferred embodiment, the Fndc5 protein has an amino acid sequence which is encoded by a nucleotide sequence which hybridizes, e.g., hybridizes under stringent conditions, to the nucleotide sequence of SEQ ID NO:1, 3, 5, 7, 9, 11, 13 or 15, or fragment thereof, or a nucleotide sequence which is at least about 50%, preferably at least about 60%, more preferably at least about 70%, yet more preferably at least about 80%, still mom preferably at least about 90%, and most preferably at least about 95% or more homologous to the nucleotide sequence shown in SEQ ID NO: 1, 3, 5, 7, 9, 11, 13 or 15, or fragment thereof. The preferred Fndc5 proteins of the present invention also preferably possess at least one of the Fndc5 biological activities, or activities associated with the complex, described herein. For example, a preferred Fndc5 protein of the present invention includes an amino acid sequence encoded by a nucleotide sequence which hybridizes, e.g., hybridizes under stringent conditions, to the nucleotide sequence of SEQ ID NO:1, 3, 5, 7, 9, 11, 13 or 15, or fragment thereof and which can maintain one or more of the following biological activities or, in complex, modulates (e.g., enhance) one or more of the following biological activities: 1) BDNF expression in the central and/or peripheral nervous system; 2) activity-induced immediate early gene expression in neurons; 3) neuronal survival; 4) neurological lesion formation; 5) neurite outgrowth; 6) synaptogenesis; 7) synaptic plasticity; 8) neuronal mitochondrial function; 9) dendritic arborization; 10) neuronal differentiation; and 11) neuronal migration.

Biologically active portions of the Fndc5 protein include peptides comprising amino acid sequences derived from the amino acid sequence of the Fndc5 protein, e.g., the amino acid sequence shown in SEQ ID NO: 2, 4, 6, 8, 10, 12 or 14, or fragment thereof, or the amino acid sequence of a protein homologous to the Fndc5 protein, which include fewer amino acids than the full length Fndc5 protein or the full length protein which is homologous to the Fndc5 protein, and exhibit at least one activity of the Fndc5 protein, or complex thereof. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, extracellular domain, fibronectin domain, hydrophobic, and/or C-terminal domain). In a preferred embodiment, the biologically active portion of the protein which includes one or more the domains/motifs described herein can increase 1) BDNF expression in the central and/or peripheral nervous system; 2) activity-induced immediate-early gene expression in neurons; 3) neuronal survival; 4) neurological lesion formation; 5) neurite outgrowth; 6) synaptogenesis; 7) synaptic plasticity; 8) neuronal mitochondrial function; 9) dendritic arborization; 10) neuronal differentiation; and 11) neuronal migration. Moreover, other biologically active portions, in which other regions of the protein are deleted, can be prepared by recombinant techniques and evaluated for one or more of the activities described herein. Preferably, the biologically active portions of the Fndc5 protein include one or more selected domains/motifs or portions thereof having biological activity. In an exemplary embodiment, an Fndc5 fragment comprises and/or consists of about amino acids 29-140, 29-150, 30-140, 30-150, 73-140, 73-150, 1-140, 1-150, or any range in between residues 1 and 150 of SEQ ID NO:2. In another embodiment, an Fndc5 fragment consists of a portion of a full-length Fndc5 fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

Fndc5 proteins can be produced by recombinant DNA techniques. For example, a nucleic acid molecule encoding the protein is cloned into an expression vector (as described above), the expression vector is introduced into a host cell (as described above) and the Fndc5 protein is expressed in the host cell. The Fndc5 protein can then be isolated from the cells by an appropriate purification scheme using standard protein purification techniques. Alternative to recombinant expression, an Fndc5 protein, polypeptide, or peptide can be synthesized chemically using standard peptide synthesis techniques. Moreover, native Fndc5 protein can be isolated from body fluids like plasma or cells (e.g., neurons), for example using an anti-Fndc5 antibody (described further below).

Also provided are Fndc5 chimeric or fusion proteins. As used herein, an Fndc5 "chimeric protein" or "fusion protein" comprises an Fndc5 polypeptide operatively linked to a non-Fndc5 polypeptide. A "Fndc5 polypeptide" refers to a polypeptide having an amino acid sequence corresponding to Fndc5, whereas a "non-Fndc5 polypeptide" refers o a polypeptide having an amino acid sequence corresponding to a protein which is not substantially homologous to the Fndc5 protein, respectively, e.g., a protein which is different from the Fndc5 protein and which is derived from the same or a different organism. Within the fusion protein, the term "operatively linked" is intended to indicate that the Fndc5 polypeptide and the non-Fndc5 polypeptide are fused in-frame to each other. The non-Fndc5 polypeptide can be fused to the N-terminus or C-terminus of the Fndc5 polypeptide, respectively. For example, in one embodiment the fusion protein is a Fndc5-GST and/or Fndc5-Fc fusion protein in which the Fndc5 sequences, respectively, are fused to the N-terminus of the GST or Fc sequences. Such fusion proteins can facilitate the purification, expression, and/or bioavailability of recombinant Fndc5. In another embodiment, the fusion protein is an Fndc5 protein containing a heterologous signal sequence at its C-terminus. In certain host cells (e.g., mammalian host cells), expression and/or secretion of Fndc5 can be increased through use of a heterologous signal sequence.

Preferably, an Fndc5 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An Fndc5-encoding nucleic acid can be cloned into such an expression vector such that the fusion moiety is linked in-frame to the Fndc5 protein.

Also provided are homologues of the Fndc5 proteins which function as either an Fndc5 agonist (mimetic) or an Fndc5 antagonist. In a preferred embodiment, the Fndc5 agonists and antagonists stimulate or inhibit, respectively, a subset of the biological activities of the naturally occurring form of the Fndc5 protein. Thus, specific biological effects can be elicited by treatment with a homologue of limited function. In one embodiment, treatment of a subject with a homologue having a subset of the biological activities of the naturally occurring form of the protein has fewer side effects in a subject relative to treatment with the naturally occurring form of the Fndc5 protein.

Homologues of the Fndc5 protein can be generated by mutagenesis, e.g., discrete point mutation or truncation of the Fndc5 protein. As used herein, the term "homologue" refers to at variant form of the Fndc5 protein which acts as an agonist or antagonist of the activity of the Fndc5 protein. An agonist of the Fndc5 protein can retain substantially the same, or a subset, of the biological activities of the Fndc5 protein. An antagonist of the Fndc5 protein can inhibit one or more of the activities of the naturally occurring form of the Fndc5 protein, by, for example, competitively binding, to a downstream or upstream member of the Fndc5 cascade which includes the Fndc5 protein. Thus, the mammalian Fndc5 protein and homologues thereof of the present invention can be, for example, either positive or negative regulators of adipocyte differentiation and/or thermogenesis in brown adipocytes.

In an alternative embodiment, homologues of the Fndc5 protein can be identified by screening combinatorial libraries of mutants, e.g., truncation mutants, of the Fndc5 protein for Fndc5 protein agonist or antagonist activity. In one embodiment, a variegated library of Fndc5 variants is generated in combinatorial mutagenesis at the nucleic acid level and is encoded by a variegated gene library. A variegated library of Fndc5 variants can be produced by, for example, enzymatically ligating a mixture of synthetic oligonucleotides into gene sequences such that a degenerate set of potential Fndc5 sequences is expressible as individual polypeptides, or alternatively, as a set of larger fusion proteins (e.g., for phage display) containing the set of Fndc5 sequences therein. There are a variety of methods which can be used to produce libraries of potential Fndc5 homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential Fndc5 sequences. Methods for synthesizing degenerate oligonucleotides are known in the art (see, e.g., Narang, S. A, (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the Fndc5 protein coding can be used to generate a variegated population of Fndc5 fragments for screening and subsequent selection of homologues of an Fndc5 protein. In one embodiment, a library of coding sequence fragments can be generated by treating a double stranded PCR fragment of an Fndc5 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the Fndc5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Fndc5 homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify Fndc5 homologues (Arkin and Youvan (1992) *Proc. Natl. Acad. Sci. USA* 89:7811-7815; Delagrave et al. (1993) *Protein Engineering* 6(3):327-331).

In addition, useful host cells and vectors are described supra for expressing desired nucleic acids and proteins for use according to the methods described herein.

EXEMPLIFICATION

This invention is further illustrated by the following examples, which should not be construed as limiting.

Example 1: Materials and Methods for Examples 1-10

A. Reagents

All primers used are listed with their sequences in Table 2. Recombinant human BDNF was purchased from PeproTech. Recombinant human GDNF and CNTF and forskolin were obtained from Sigma. Recombinant mouse IGF-1 was obtained, from R&D Systems. Recombinant mouse NGF and K252a were obtained from EMD Nifedipine, XCT 790, DY131, GW7647, and GW0742 were purchased from Tocris. Recombinant irisin (human, rat, mouse, canine) was obtained from Phoenix Pharmaceuticals (Burlingame, Calif.).

TABLE 2

| Primer | Sequence (5' to 3') |
|---|---|
| mRps18 QS | CATGCAGAACCCACGACAGTA |
| mRps18 AS | CCTCACGCAGCTTGTTGTCTA |
| mFndc5QS | ATGAAGGAGATGGGGAGGAA |
| mFndc5QA | GCGGCAGAAGAGAGCTATAACA |
| mPGC-1aQS | TGATGTGAATGACTTGGATACAGACA |
| mPGC-1aQA | GCTCATTGTTGTACTGGTTGGATATG |
| mErra QS | CACTACGGTGTGGCATCCTG |
| mErra AS | ACAGCTGTACTCGATGCTCC |
| mErrb QS | AACCGAATGTCGTCCGAAGAC |
| mErrb AS | GTGGCTGAGGGCATCAATG |
| mErrg QS | ATGGATTCGGTAGAACTTTGCC |

TABLE 2-continued

| Primer | Sequence (5' to 3') |
|---|---|
| mErrg AS | CTTCTTCGTAGTGCAGGGAAAA |
| mBdnf QS | TGGCCCTGCGGAGGCTAAGT |
| mBdnf AS | AGGGTGCTTCCGAGCCTTCCT |
| mIgf1 QS | TGGATGCTCTTCAGTTCGTG |
| mIgf1 AS | GTCTTGGGCATGTCAGTGTG |
| mNpas4QS | CTGCATCTACACTCGCAAGG |
| mNpas4QA | GCCACAATGTCTTCAAGCTCT |
| mc-FosQS | ATGGGCTCTCCTGTCAACACAC |
| mc-FosQA | ATGGCTGTCACCGTGGGGATAAAG |
| mArcQS | TACCGTTAGCCCCTATGCCATC |
| mArcQA | TGATATTGCTGAGCCTCAACTG |
| mZif268QS | TATGAGCACCTGACCACAGAGTCC |
| mZif268QA | CGAGTCGTTTGGCTGGGATAAC |

Key
QS: qPCR-sense
QA: qPCR-antisense

In addition to the Fndc5 sequences described herein (e.g., Table 1), the following sequences are useful for generating the constructs used in the experiments described below.

For example, the IrisinFc constructs encode or are composed of the following amino acid sequence:

DSPSAPVNVTVRHLKANSAVVSWDVLEDEVVIGFAISQQKKDVRM
LRFIQEVNTTTRSCALWDLEEDTEYIVHVQAISIQGQSPASEPVL
FKTPREAEKMASKNKDEVTMKEGGGGAGGGGVECPPCPAPPVAGP
SVFLFPPKPKDTLMISRTPEVTCVVVDVSHEDPEVQFNWYVDGVE
VHNAKTKPREEQFNSTFRVVSVLTVVHQDWLNGKEYKCKVSNKGL
PAPIEKTISKTKGQPREPQVYTLPPSREEMTKNQVSLTCLVKGFY
PSDIAVEWESNGQPENNYKTTPPMLDSDGSFFLYSKLTVDKSRWQ
QGNVFSCSVMHEALHNHYTQKSLSLSPGK.

The control human Fc (hFc) constructs encode or are composed of the following amino acid sequence:

VECPPCPAPPVAGPSVFLFPPKPKDTLMISRTPEVTCVVVDVSHE
DPEVQFNWYVDGVEVHNAKTKPREEQFNSTFRVVSVLTVVHQDWL
NGKEYKCKVSNKGLPAPIEKTISKTKGQPREPQVYTLPPSREEMT
KNQVSLTCLVKGFYPSDIAVEWESNGQPENNYKTTPPMLDSDGSF
FLYSKLTVDKSRWQQGNVFSCSVMHEALHNHYTQKSLSLSPGK.

The GFP sequence used in the GFP adenovirus constructs are encoded by the following nucleic acid sequence:

AAGCTTGGGATGGTGAGCAAGGGCGAGGAGCTGTTCACCGGGGTG
GTGCCCATCCTGGTCGAGCTGGACGGCGACGTAAACGGCCACAAG

-continued

TTCAGCGTGTCCGGCGAGGGCGAGGGCGATGCCACCTACGGCAAG
CTGACCCTGAAGTTCATCTGCACCACCGGCAAGCTGCCCGTGCCC
TGGCCCACCCTCGTGACCACCCTGACCTACGGCGTGCAGTGCTTC
AGCCGCTACCCCGACCACATGAAGCAGCACGACTTCTTCAAGTCC
GCCATGCCCGAAGGCTACGTCCAGGAGCGCACCATCTTCTTCAAG
GACGACGGCAACTACAAGACCCGCGCCGAGGTGAAGTTCGAGGGC
GACACCCTGGTGAACCGCATCGAGCTGAAGGGCATCGACTTCAAG
GAGGACGGCAACATCCTGGGGCACAAGCTGGAGTACAACTACAAC
AGCCACAACGTCTATATCATGGCCGACAAGCAGAAGAACGGCATC
AAGGTGAACTTCAAGATCCGCCACAACATCGAGGACGGCAGCGTG
CAGCTCGCCGACCACTACCAGCAGAACACCCCCATCGGCGACGGC
CCCGTGCTGCTGCCCGACAACCACTACCTGAGCACCCAGTCCGCC
CTGAGCAAAGACCCCAACGAGAAGCGCGATCACATGGTCCTGCTG
GAGTTCGTGACCGCCGCCGGGATCACTCTCGGCATGGACGAGCTG
TACAAGTAACGCGGATCCACTAGTTCTAGAGC.

Additional information as to construct generation and sequences, such as Fc fusion constructs, are described in Bostrom et al. (2012) *Nature* 481, 463-468.

B. Animal Studies

All animal experiments were performed according to procedures approved by the IACUC of Dana-Farber Cancer Institute and the BIDMC. Generation and characterization of the Pgc1a total body KO (Pgc1a$^{-/-}$) mice have been described previously in Lin et al. (2004) *Cell* 119, 121-135. Mice were kept under 14-hour light/10-hour dark cycles at constant temperature (22° C.) with free access to food and water. Mice were fed a standard diet (Rodent Diet 8664, Harlan Teklad). For free wheel running exercise, six week old male wild type C56/Bl6 mice (Jackson Laboratory) were housed individually with stainless steel running wheels. Sedentary controls were housed without wheels. Mice were exercised for 30 days and sacrificed approximately 10 h after their last bout of exercise and the indicated tissues were harvested. For the tissue panel, 13 weeks old male C57/Bl6 mice were used. For the developmental time-course pups were sacrificed at the indicated time-points and brains were harvested for total RNA. For RNA expression studies, animals were sacrificed and tissues harvested and stored at −80° C. until analysis.

C. Cell Culture

Primary cortical and hippocampal neurons were isolated as described in great detail previously in Bartlett and Banker (1984) *J. Neurosci.* 4, 1944-1953. Briefly, cortices and hippocampi were dissected from E16-E18 embryos, dissociated with trypsin (Sigma) and DNAse (Roche), and plated on poly-L-lysine-coated (Sigma) plates. Dissociated neurons were cultured in Neurobasal Media supplemented with B27, GlutaMAX™ (Life Technologies), and Penicillin-Streptomycin (Cellgro).

D. RNA Preparation and Expression Analysis

Cells or tissues were lysed and homogenized in TRIzol (Invitrogen). Total RNA was subsequently isolated using the RNeasy Mini or Micro Kit (Qiagen). First-strand cDNA was generated using the High Capacity cDNA Reverse Transcription Kit (Life Technologies), and qPCR was performed using SYBR Green Master Mix in a 7900HT Real-Time PCR system (Applied Biosystems). mRNA quantities were normalized to Rsp18 after determination by the comparative Ct method (Schmittgen and Livak (2008) *Nat. Protocols* 3, 1101-1108).

E. Protein Extraction and Western Blot Analysis

Cell lysates were prepared with RIPA buffer supplemented with complete protease inhibitor cocktails. For generation of conditioned media cells were washed three times with PBS and plain neurobasal with glutamine and antibiotics but without B27 supplement was added. Cells and media were collected the next morning. The conditioned media was spun twice at low speed and then concentrated in spin-filter columns with a molecular weight cut-off of 3 KDa Deglycosylation was performed using Protein Deglycosylation Mix (New England Biolabs). Blood was collected in lithium heparinized tubes (BD Biosciences) and plasma was separated by centrifugation. Albumin and IgG was removed using the ProteoExtract-kit (Millipore). Then the samples were concentrated using Ultra-2 Centrifugal Filter (Millipore) and deglycosylated with PNGase F (New England Biolabs).

For Western blot analyses, 80-100 μg protein was subjected to SDS-PAGE under reducing conditions, transferred, and blotted with anti-PGC-1α mouse (4C1.3) antibody (Calbiochem/EMD Millipore,) and anti-FNDC5 (Irisin) rabbit polyclonal antibody (Adipogen). Equal loading was assessed by Ponceau staining (Sigma-Aldrich).

F. Forced Expression and Knockdown

Generation and delivery of the PGC-1α, GFP, and FNDC5 adenovirus has been described in detail in Bostrom et al. (2012) *Nature* 481, 463-468 and Lustig et al. (2011) *Genes Dev.* 25, 1232-1244.

Primary cortical neurons were transduced at the indicated time-points and were harvested 48 hrs later for RNA isolation. For knockdown studies, primary cortical neurons were transduced with viral supernatants from HEK293T cells transfected with pLKO.1 vector (TRC) containing the specified shRNAs at the indicated time-points. The sequences of shRNAs used are as follows:

| | Target Sequence (5' to 3') | Forward Oligo Sequence (5' to 3') | Reverse Oligo Sequence (5' to 3') |
|---|---|---|---|
| shFndc5-1 | CCCTCTGTGAACATCATCAAA | CCGGCCCTCTGTGAACATCATCAAACTCGAGTTTGATGATGTTCACAGAGGGTTTTTG | AATTCAAAAACCCTCTGTGAACATCATCAAACTCGAGTTTGATGATGTTCACAGAGGG |
| shFndc5-2 | GTGCGGATGCTCCGGTTCATT | CCGGGTGCGGATGCTCCGGTTCATTCTCGAGAATGAACCGGAGCATCCGCACTTTTTG | AATTCAAAAAGTGCGGATGCTCCGGTTCATTCTCGAGAATGAACCGGAGCATCCGCAC |
| shFndc5-3 | CGAGCCCAATAACAACAAGGA | CCGGCGAGCCCAATAACAACAAGGACTCGAGTCCTTGTTGTTATTGGGCTCGTTTTTG | AATTCAAAAACGAGCCCAATAACAACAAGGACTCGAGTCCTTGTTGTTATTGGGCTCG |

Cells were harvested four days later for total RNA. To produce lentiviral supernatants, HEK293T cells cultured in DMEM with 10% FBS, were transfected using Lipofectamine2000™ (Life Technologies) with the specified shRNA plasmid and the packing plasmid psPAX2 and pMD2.G in a 2:1:1 ratio. After an overnight incubation, media was exchanged to neurobasal media supplemented as described above and supernatants were harvested 24 hrs later.

G. Cell Viability Assay

Cell viability of cultured neurons was assessed using CellTiter-Glo® Luminescent Cell Viability Assay (Promega, Madison, Wis.) according to the manufacturer's instructions. Luminescence of cell lysates was measured using the FLUOstar Omega plate reader (BMG LABTECH, Offenburg, Germany).

H. Analysis of the Murine Fndc5 Promoter for Erra Transcription Factor Binding Sites The genomic sequence of the murine Fndc5 gene and 6 kb of its upstream promoter was retrieved from the USCS Genome browser (available on the World Wide Web at genome.ucsc.edu; assembly mm9). This genomic sequence was searched for the canonical Erra transcription facto binding motif: TGACCTT. This motif had been identified and established in previous studies described in Charest-Marcotte et al. (2010) *Genes Dev.* 24, 537-542; Mootha et al. (2004) *Proc. Natl. Acad. Sci.* 101, 6570-6575; and Wang et al. (2012) *Genome Res.* 22, 1798-1812.

I. Peripheral Delivery of FNDC5 by Adenoviral Vectors

High titer GFP- or FNDC5-expressing adenoviral particles were obtained by ViraQuest Inc. (North Liberty, Iowa). Five week old male wild-type BALB/c mice were injected with GFP- or FNDC5-expressing adenoviral particles ($10^{11}$/animal) intravenously. Animals were sacrificed seven days later and the indicated tissues were harvested for gene expression analyses using qPCR.

J. Stem Cell Differentiation and Glial Co-Culture

Growth of human embryonic stem cells, differentiation of human embryonic stem cells into motor neurons, and glial co-culture were performed as described in DiGiorgio et al. (2008) *Cell Stem Cell* 3:637-648.

Example 2: Endurance Exercise Induces Hippocampal Fndc5 Gene Expression

Figure 2:
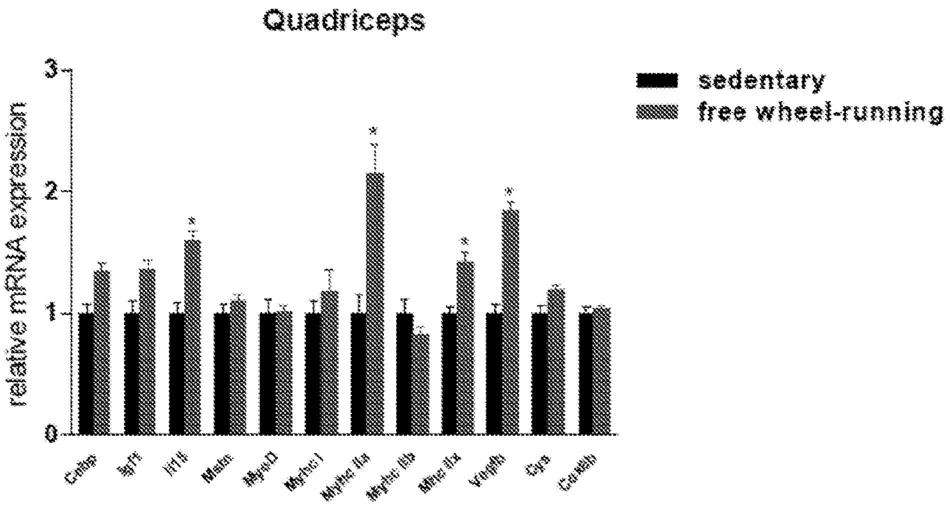
FIG. 2 shows an adaptive endurance exercise response in quadriceps muscle using qPCR analyses from mice treated as described in FIG. 1.

Although FNDC5 is highly expressed in the brain, as well as in skeletal muscle (Ferrer-Martinez et al. (2002) *Dev. Dyn.* 224, 154-167 and Teufel et al. (2002) *Gene* 297, 79-83), very little is known about its function in the brain. In order to investigate the effects of exercise on FNDC5 expression and function, an established endurance exercise regimen of 30 days of voluntary free running-wheel exercise was used. This regimen is known to induce BDNF expression, neurogenesis, dendritic spines and improved memory function in mice (Eadie et al. (2005) *J. Comp. Neurol.* 486, 39-47 and Kobilo et al. (2011) *Learning Mem.* (Cold Spring Harbor, N.Y.) 18, 605-609). As has previously been established, this training was sufficient to induce muscle Fndc5 gene expression (FIG. 1A), as well as the transcriptional regulators Pgc1a and Erra, known mediators of the exercise-response in skeletal muscle. In addition, other known genes of the exercise gene program were induced, confirming an adaptive endurance exercise response in the muscle (FIG. 2). The same exercise regime led to a significant elevation of Fndc5 expression in the hippocampus (FIG. 1B) but not in the remainder of the brain (FIG. 1C). The hippocampus is a region of the brain involved in learning and memory and has been identified as a major site where changes induced by exercise occur. Even though genes that are induced by neuronal activity, such as Arc, cFos and Zif268, were upregulated in both the remainder of the brain and the hippocampus, the important exercise-related neurotrophin Bdnf was induced only in the hippocampus (FIGS. 1D-1E). However, Npas4, an important transcriptional component in hippocampal function and a key regulator of activity-induced Bdnf expression (Lin et al. (2008) *Nature* 455, 1198-1204 and Ramamoorthi et al. (2011) *Science* 334, 1669-1675) was not increased in the exercise regimen used here (FIGS. 1D-1E). These data indicate that the induction of FNDC5 is part of the transcriptional response to exercise in the hippocampus.

Figure 3:
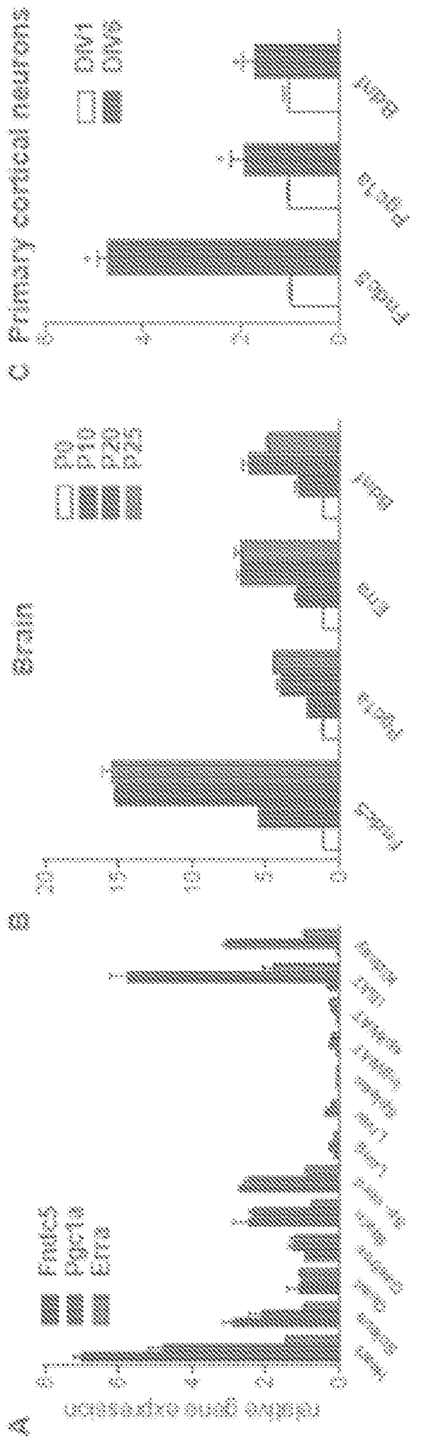
FIGS. 3A-3C shows that Fndc5 gene expression correlates with Pgc1a expression levels in various tissues and developmental stages.

Example 3: Fndc5 Gene Expression Correlates with Pgc1a Expression Levels in Various Tissues and Developmental Stages It was previously reported that elevations in Fndc5 gene expression in exercised muscle was dependent on PGC-1α (Bostrom et al. (2012) *Nature* 481, 463-468). It was therefore investigated whether Fndc5 expression in the brain is also regulated by PGC-1α. To first assess if there is a correlation between the gene expression of these two proteins, different tissues were isolated from C57/Bl6 mice, total RNA was extracted, and gene expression was measured for Fndc5 and Pgc1a. Consistent with earlier reports, the highest level of Fndc5 gene expression was detected in heart, skeletal muscle, brain and spinal cord (Ferrer-Martinez et al. (2002) *Dev. Dyn.* 224, 154-167 and Teufel et al. (2002) *Gene* 297, 79-83). When the different tissues were grouped according to their levels of Fndc5 expression, most tissues with very high Fndc5 expression also showed relatively high levels of Pgc1a gene expression (FIG. 3A). Fndc5 and Pgc1a expression levels correlated well, even within very distinct muscle beds. Fndc5 expression was higher in oxidative muscle, such as the soleus muscle, which also contains higher levels of Pgc1a, than in glycolytic or mixed muscles, such as gastrocnemius or quadriceps muscle. Exceptions to this tight correlation of Fndc5 and Pgc1a expression are the interscapular brown adipose tissue and the kidney. Both are tissues with extremely high mitochondrial content, which might explain their requirement for high Pgc1a levels without very high expression of Fndc5.

To examine whether FNDC5 and PGC-1α were developmentally regulated in synchrony during maturation of the brain, a time-course experiment of postnatal development was performed. Brains were harvested from pups at postnatal day 0 (P0), P10, P20, P25, and P30 and gene expression was measured by qPCR. These time-points were chosen because they cover an important time period of postnatal brain developmental, up to the mature state at P30. A two-step pattern of increased Fndc5 gene expression during development was observed, with a first increase between P0 and P10 and second increase between P10 and P20, which then leveled off (FIG. 3B). Pgc1a gene expression followed essentially the same pattern. This two-step pattern of increased gene expression during brain development was also observed for the key neural regulatory protein, Bdnf. Next, the gene expression patterns for these factors were assessed during the maturation of primary cortical neurons in culture. The correlation was observed again: Fndc5 gene expression increased between in vitro days (DIV) 1 and DIV 6, when the expression levels of Pgc1a and Bdnf were also elevated (FIG. 3C). These data illustrate that, similar to muscle, there is a strong correlation between PGC-1α and FNDC5 gene expression in the brain.

Example 4: Neuronal Fndc5 Gene Expression is Regulated by PGC-1α

Figure 4:
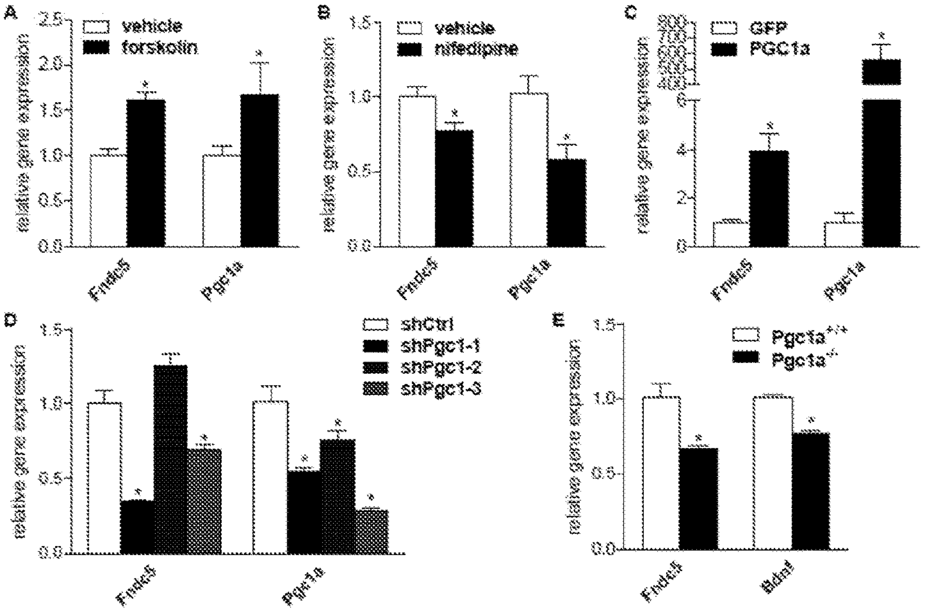
FIGS. 4A-4E show that neuronal Fndc5 gene expression is regulated by PGC-1α.

To investigate whether PGC-1α is a transcriptional regulator of Fndc5 gene expression in the brain, dissociated primary conical neurons in culture were used. Although more heterogeneous than neurons from the dentate gyrus of the hippocampus, these cultures can be isolated in sufficient quantities for molecular studies and can be readily manipulated Primary cortical neurons were stimulated with forskolin (10 μM), a strong inducer of intracellular cAMP, which is known to increase Pgc1a gene expression in cell types as diverse as brown adipocytes, hepatocytes and Schwann cells (Cowell et al. (2008) *Neurosci. Lett.* 439, 269-274; Herzig et al. (2001) *Nature* 413, 179-183; and Yoon et al. (2001) *Nature* 413, 131-138). This increase in Pgc1a gene expression was accompanied by a significant increase in Fndc5 gene expression (FIG. 4A). On the other hand, treatment of cortical neurons with nifedipine (5 μM), a selective L-type calcium channel blocker, which leads to decreased intracellular calcium levels and decreased Pgc1a gene expression, was accompanied by decreased Fndc5 gene expression (FIG. 4B).

Figure 5:
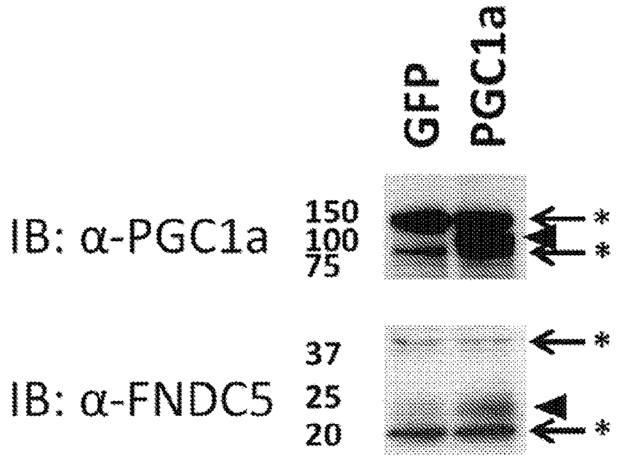
FIG. 5 shows the results of primary cortical neurons at DIV 6 transduced with either PGC-1α or GFP adenovirus. Forty-eight hours later, whole cell lysates were harvested and analyzed by immunoblotting. *=unspecific band. Intensity of unspecific bands and Ponceau staining were used to assess equal loading.

Next, genetic gain- and loss-of-function approaches were used to test causality. Forced expression of PGC-1α by adenoviral deliver in primary cortical neurons resulted in a 4-fold increase in Fndc5 gene expression (FIG. 4C). Immunoblotting confirmed that the increase in Fndc5 mRNA translated into elevated FNDC5 protein levels (FIG. 5). Conversely, reducing Pgc1a gene expression with lentiviral-mediated shRNA knockdown by more than 40% significantly decreased Fndc5 gene expression by 66 and 31%, respectively (FIG. 4D). As an additional loss-of-function model, the brains of global Pgc1a knockout mice (Pgc1a−/−) were used. The same requirement of PGC-1α for Fndc5 gene expression in brains of these mice, which display a reduction in Fndc5 gene expression by 32%, was observed (FIG. 4E). Taken together, these results demonstrate that PGC-1α is a regulator of neuronal Fndc5 gene expression in neural cultures and in the brain.

Example 5: ERRα is a Key Interacting Transcription Factor with PGC-1α for Regulating Fndc5 Gene Expression in Neurons PGC-1α is a transcriptional co-activator, meaning it does not bind to the DNA itself but interacts with transcription factors to execute its effects on gene expression (Spiegelman (2007) *Novartis Foundation Sympos.* 287, 60-69). The orphan nuclear receptor estrogen-related receptor alpha (ERRα; also known as NR3B1) is a central metabolic regulator (Giguere et al. (1988) *Nature* 331, 91-94 and Luo et al. (2003) Mol. Cell. Biol. 23, 7947-7956) and a very important interactor with PGC-1α (Laganiere et al. (2004) *J. Biol. Chem,* 279, 18504-18510; Mootha et al. (2004) *Proc. Natl. Acad. Sci. U.S.A.* 101, 6570-6575; and Schreiber et al. (2004) *Proc. Natl. Acad. Sci. U.S.A.* 101, 6472-6477). The interaction of Errα with PGC-1α has been best studied in skeletal muscle, where it is required for mitochondrial biogenesis, induction of angiogenesis, oxidative metabolism, and oxidative muscle fibers (Arany et al. (2008) *Nature* 451, 1008-1012; Mootha et al. (2004) *Proc. Natl. Acad. U.S.A.* 101, 6570-6575; and Schreiber et al. (2004) *Proc. Natl. Acad. Sci. U.S.A.* 101, 6472-6477).

Figure 6:
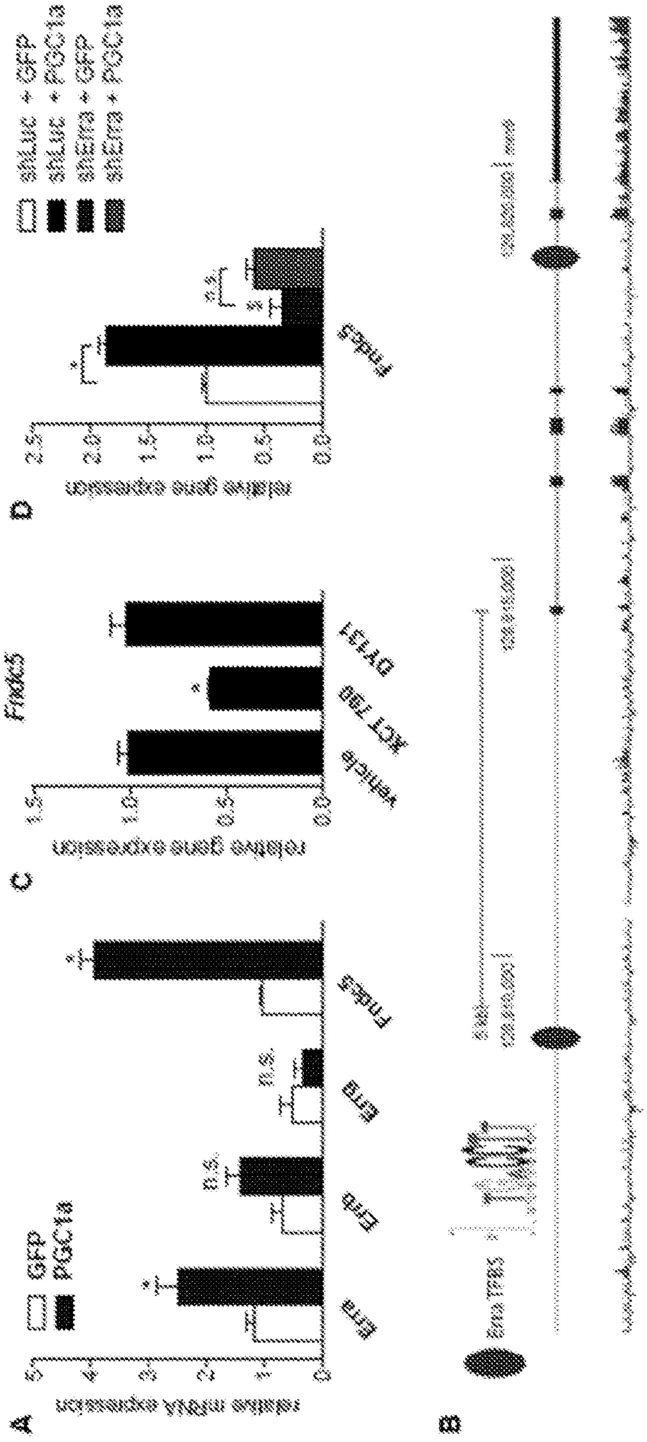
FIGS. 6A-6D show that ERRα is a key interacting transcription factor with PGC-1α for regulating Fndc5 gene expression in neurons.
Figure 7:
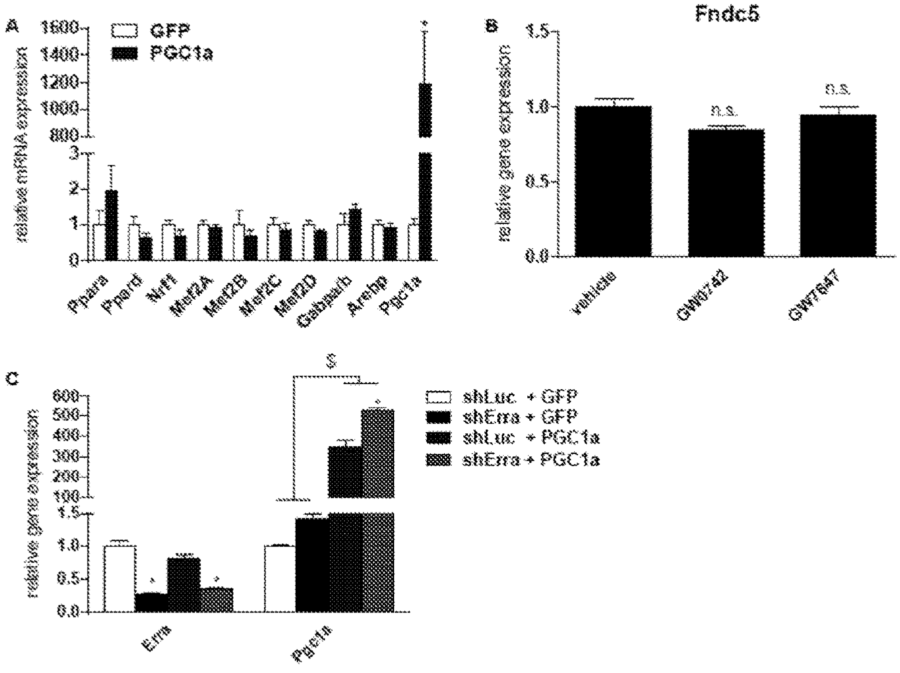
FIGS. 7A-7C provide additional data demonstrating that ERRα is a key interacting transcription factor with PGC-1α for regulating Fndc5 gene expression in neurons.

Erra follows the exercise-induced gene expression pattern of Fndc5 in the brain. Erra is up-regulated in the hippocampus upon exercise but not in the rest of the brain (FIGS. 1B-1C). In addition, there was a correlation between Fndc5 and Erra gene expression in the tissue-panel (FIG. 3A) as well as in the developmental time-course (FIG. 3B). PGC-1α is well-known to often increase the expression of transcription factors that it interacts with, thereby positively regulating its own regulators (Handschin et al. (2003) *Proc. Natl. Acad. Sci. U.S.A.* 100, 7111-7116 and Mootha et al. (2004) *Proc. Natl. Acad. Sci. U.S.A.* 101, 6570-6575). It was therefore asked if forced expression of PGC-1α in primary cortical neurons results in an increase Erra mRNA. Indeed, adenoviral expression of PGC-1α significantly increased Erra gene expression, but not Errb or Errg gene expression (FIG. 6A). However, mRNA for other common binding partners of PGC-1α, such as Mef2, Ppara, Nrf1 or Gabpa/b was not induced in these experiments (FIG. 7A).

The murine Fndc5 gene and 6 kb of its upstream promoter were searched for putative ERRα transcription factor binding sites, (ERRE), with the canonical 'TGACCTT' sequence (Charest-Marcotte et al. (2010) *Genes Dev.* 24, 537-542; Mootha et al. (2004) *Proc. Natl. Acad. Sci. U.S.A.* 101, 6570-6575; and Wang et al. (2012) *Genome Res.* 22, 1798-1812). Two putative ERRE's were identified: one around 5.3 kb upstream of the transcriptional start site and one in the fourth intron of the Fndc5 gene (FIG. 6B). ERRα had been previously reported to also bind to intronic sequences to exert its biological function (Arany et al. (2008) *Nature* 451, 1008-1012). This further indicates that ERRα is important in FNDC5 gene regulation.

Treatment of primary cortical neurons with XCT 790 (1 μM), a selective ERRα inhibitor (inverse agonist), which disrupts the ERRα/PGC-1α transcriptional complex (Mootha et al. (2004) *Proc. Natl. Acad. Sci. U.S.A.* 101, 6570-6575), significantly reduced Fndc5 gene expression compared to vehicle treated cells (FIG. 6C). However, stimulation with DY131 (1 μM), a selective ERRβ and ERRγ agonist, had no effect on Fndc5 gene expression. This results indicates certain specificity for the involvement of ERRα compared to other ERR subfamily members. Since the nuclear receptor PPARα, another common binding partner of PGC-1α, was slightly induced by forced expression of PGC-1α, the effect of GW7647, a potent and highly selective PPARα agonist, and GW0742, a potent and highly selective PPARδ agonist were tested on Fndc5 gene expression. However, under the conditions tested, no effect on Fndc5 gene expression in primary cortical neurons by these compounds was observed (FIG. 7B).

The results from the treatment with ERRα antagonist indicate that interaction of the PGC-1α with ERRα is required for the PGC-1α-dependent induction of Fndc5 gene expression. To test this, ERRα was first knocked down in primary cortical neurons using lentivirally expressed shRNA hairpins and then three days later the cells were transduced with either the PGC-1α adenovirus or GFP expressing adenovirus. Erra mRNA was efficiently knocked-down by this hairpin (70%) and forced expression of PGC-1α did not affect the efficiency of the knock-down (FIG. 3CC). Knockdown of ERRα significantly reduced Fndc5 gene expression at base line (FIG. 6D). Furthermore, forced expression of PGC-1α by adenovirus in the cells with reduced ERRα failed to significantly increase Fndc5 gene expression (FIG. 6D). However, this failure to increase Fndc5 gene expression was not due to a lack over expression of PGC-1α in the shErra
treated neurons (FIG. 7C).

Figure 8:
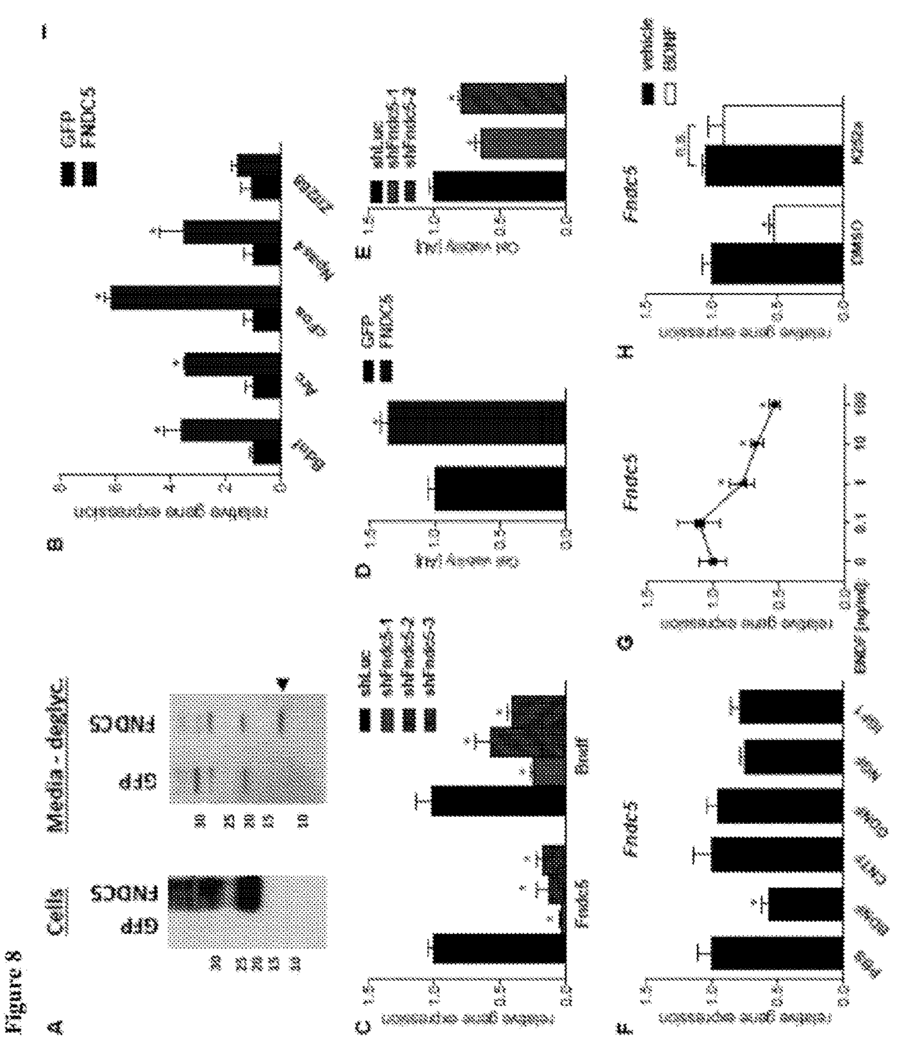
FIGS. 8A-8H shows that FNDC5 regulates Bdnf gene expression in a cell-autonomous manner and recombinant BDNF decreases Fndc5 gene expression as part of negative feedback loop.

Example 6: FNDC5 Regulates Bdnf Gene Expression in a Cell-Autonomous Manner and Recombinant BDNF Decreases Fndc5 Gene Expression as Part of Potential Feedback Loop As described above, BDNF is a major mediator of certain beneficial effects on the brain. In addition, an increase in the Bdnf gene expression in the hippocampus was observed, where Fndc5 gene expression was also induced (FIGS. 1B-1D), but not in the rest of the brain, where Fndc5 was not induced (FIGS. 1C-1E). It was therefore tested whether FNDC5 could be a regulator of Bdnf gene expression in a cell culture model. Primary cortical neurons were transduced with either FNDC5 adenovirus or a GFP adenovirus as control. Forced expression of FNDC5 resulted in a clear increase in FNDC5 protein in the whole cell lysate, as well as an increase in the secreted form of FNDC5 (irisin) in the cell culture supernatant (FIG. 8A). After deglycosylation, this protein had the same apparent molecular mass (2 kDa) as predicted for irisin (FIG. 8A). In addition, forced expression of FNDC5 significantly upregulated Bdnf gene expression by four fold (FIG. 8B). Importantly, FNDC5 expression also induced other important activity-induced genes involved in hippocampal function including Npas4, cFos, and Arc. However, Zif268 was only slightly elevated.

Figure 13:
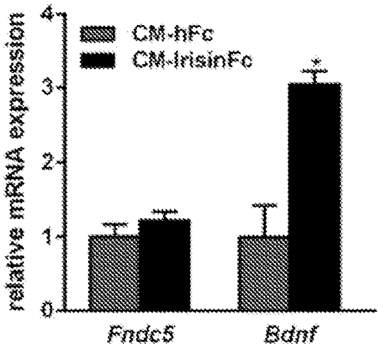
FIG. 13 shows that a secreted from of FNDC5 is sufficient to increase Bdnf gene expression in neurons release a secreted form of FNDC5 into culture media. Primary cortical neurons were treated with conditioned media (CM, 5× concentrated) from CHO cell lines overexpressing irisinFc or human Fc (hFc) as control. Total RNA for qPCR was harvested the next day. Results are shown as mean+SEM, n=3 and n=4, respectively. *P<0.05.
Figure 14:
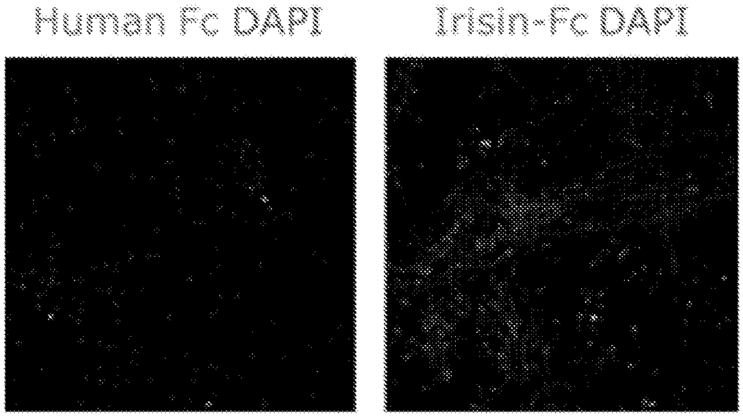
FIG. 14 shows that neurons bind irisinFc. PEA-fixed cultured primary cortical neurons were incubated with either irisin-Fc or humanFc as control and binding of irisinFc was detected by a secondary anti-human Fc fluorescent antibody. IrisinFc clearly binds to neurons in culture, especially given that the observed pattern of the binding and the fact that the cultures are highly enriched in neurons (>90%).
Figure 15:
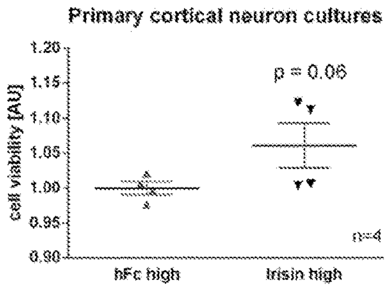
FIG. 15 shows that irisin promotes cell survival of primary cortical neurons. Primary cortical neurons were treated with either irisin-Fc or humanFc as control during in vivo culture for 7 days and cell viability was assessed using the CellGlo™ Assay from Promega as described in the Examples.

Primary cortical neurons treated with 5× concentrated conditioned media from CHO cell lines overexpressing either irisinFc or human Fc (hFc) as a control showed increased expression of Fndc5 and Bdnf (FIG. 13). In addition, FIG. 14 demonstrates that neurons bind irisinFc. Moreover, primary cortical neurons treated with either irisinFc during in vitro culture for 7 days showed significantly increased cell viability relative to treatment with hFc (FIG. 15).

To investigate if FNDC5 is required for Bdnf gene expression, lentivirally delivered shRNA was used to knockdown FNDC5 in primary cortical neurons. To address possible off-targets of a single hairpin, a total of five hairpins of which three significantly knocked down Fndc5 mRNA (FIG. 8C). The same three hairpins also significantly reduced Bdnf gene expression. The role of PGC-1α in controlling Bdnf gene expression in vivo was also analyzed. To do this, the brains of global Pgc1a knockout mice ($Pgc1a^{-/-}$) were used. As shown in FIG. 4E, Bdnf gene expression was significantly reduced in the brains of $Pgc1a^{-/-}$ mice.

BDNF is well-known for its ability to improve survival of neurons in culture. Thus, the effects of gain- and loss-of-function of FNDC5 on cell viability of cultured neurons were assessed using a luminescence/ATP-based assay. Gain-of-function of FNDC5 significantly improved neuron survival in culture (FIG. 8D), while loss-of-function of FNDC5 using shRNA mediated knockdown of FNDC5 with two different hairpins significantly impaired the survival of neurons in culture (FIG. 8E).

To examine how BDNF might, in turn, alter FNDC5 gene expression, primary cortical neurons were stimulated with recombinant BDNF overnight at various concentrations at physiological and pharmacological dosages (0.1-100 ng/ml). BDNF concentrations as low as 1 ng/ml significantly reduced Fndc5 gene expression (FIG. 8F) and a dose-response was observed. To ask whether the reduction in Fndc5 gene expression was specific to BDNF, primary cortical neurons were treated with a variety of central and peripheral neurotrophic factors in addition to BDNF, such as CNTF (ciliary neurotrophic factor), GDNF (glial cell-derived neurotrophic factor), NGF (nerve growth factor), and IGF-1 (insulin-like growth factor 1) at 100 ng/ml for overnight. However, only BDNF stimulation significantly reduced Fndc5 mRNA expression (FIG. 8G). This effect was abolished by pre-incubating the cortical neurons with a low dose (50 nM) of K252a, well-characterized inhibitor of TrkB, the receptor of BDNF signaling (Gimenez-Cassina et al. (2012) *Neurosci. Lett.* 531, 182-187 and Tapley et al.

(1992) *Oncogene* 7, 371-381) (FIG. 8H). In summary, these data indicate a homeostatic FNDC5/BDNF feed-back loop.

Example 7: Peripheral Delivery of FNDC5 by Adenoviral Vectors Increases Bdnf Expression in the Central Nervous System, Including the Hippocampus, Cerebellum, and Sciatic Nerve It was previously shown that adenoviral overexpression of FNDC5 in the liver, a major secretory organ, increases circulating levels of irisin, the secreted form of FNDC5 (Bostrom et al. (2012) *Nature* 481, 463-468). This resulted in the activation of a thermogenic gene program in certain fat tissues. To determine if peripheral delivery of FNDC5/irisin could elevate central BDNF levels, adenoviral overexpression of FNDC5 in the liver was conducted and Bdnf gene expression in the hippocampus was measured seven days later. As previously shown, forced expression of FNDC5 in the liver resulted in the induced 'browning' of the inguinal fat depot (FIG. 9A), including increased expression of mRNA for a group of key thermogenic genes, such as Pgc1a, Ucp1 and Cidea. In addition, plasma levels of irisin were elevated in mice overexpressing FNDC5 as compared to GFP-overexpressing control mice (FIG. 10A).

Figure 16:
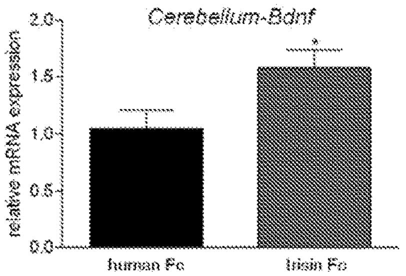
FIG. 16 shows that peripheral injections of irisin-Fc increase Bdnf gene expression in the cerebellum. Wild type C56/Bl6 mice were injected with either irisinFc or humanFc (5 mg/kg) i.p. Total RNA for qPCR was harvested 10 d later. Results are shown as mean+SEM, n=6, *P<0.05.
Figure 17:
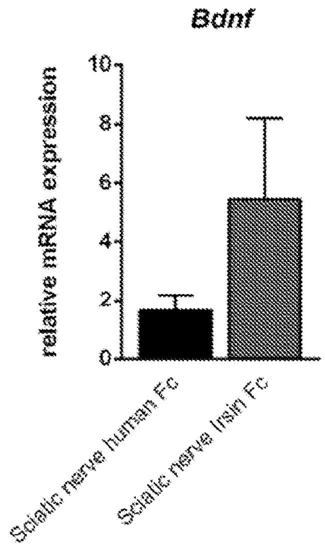
FIG. 17 shows that peripheral injections of irisin-Fc increase Bdnf gene expression in the sciatic nerve. Wild type C56/Bl6 mice were injected with either irisinFc or humanFc (5 mg/kg) i.p. Total RNA for qPCR was harvested 10 d later. Results are shown as mean+SEM, n=6, *P<0.05.

Interestingly, Bdnf expression in the hippocampus was significantly increased, as was expression of Npas4, cFos, Are, and Zif268, all part of the activity-induced immediate early gene (IEG) program as mentioned before. Importantly, this was not caused by any viral-mediated expression of Fndc5 in the brain or hippocampus (FIG. 9B), indicating that the secreted form of the peripherally-expressed FNDC5 was responsible for the observed effect. This effect of increased Bdnf expression was specific to the hippocampus and was not observed in the forebrain (FIG. 9C), whereas the IEG response was observed in both, which is consistent with the findings of the exercise effects described above (FIGS. 1D-1E). Similarly, peripheral injections of irisinFc caused a significant increase in Bdnf expression in the cerebellum (FIG. 16) and sciatic nerve (FIG. 17).

Example 8: PGC-1α/FNDC5/BDNF Pathway in Primary Hippocampal Neurons

Cortical neurons were used in the experiments described above because this is the most widely used system of primary CNS cultures and because reasonable numbers of cells can be obtained. However, since some of the described in vivo observations were made in the hippocampus, the findings were validated in primary hippocampal neurons.

Figure 11:
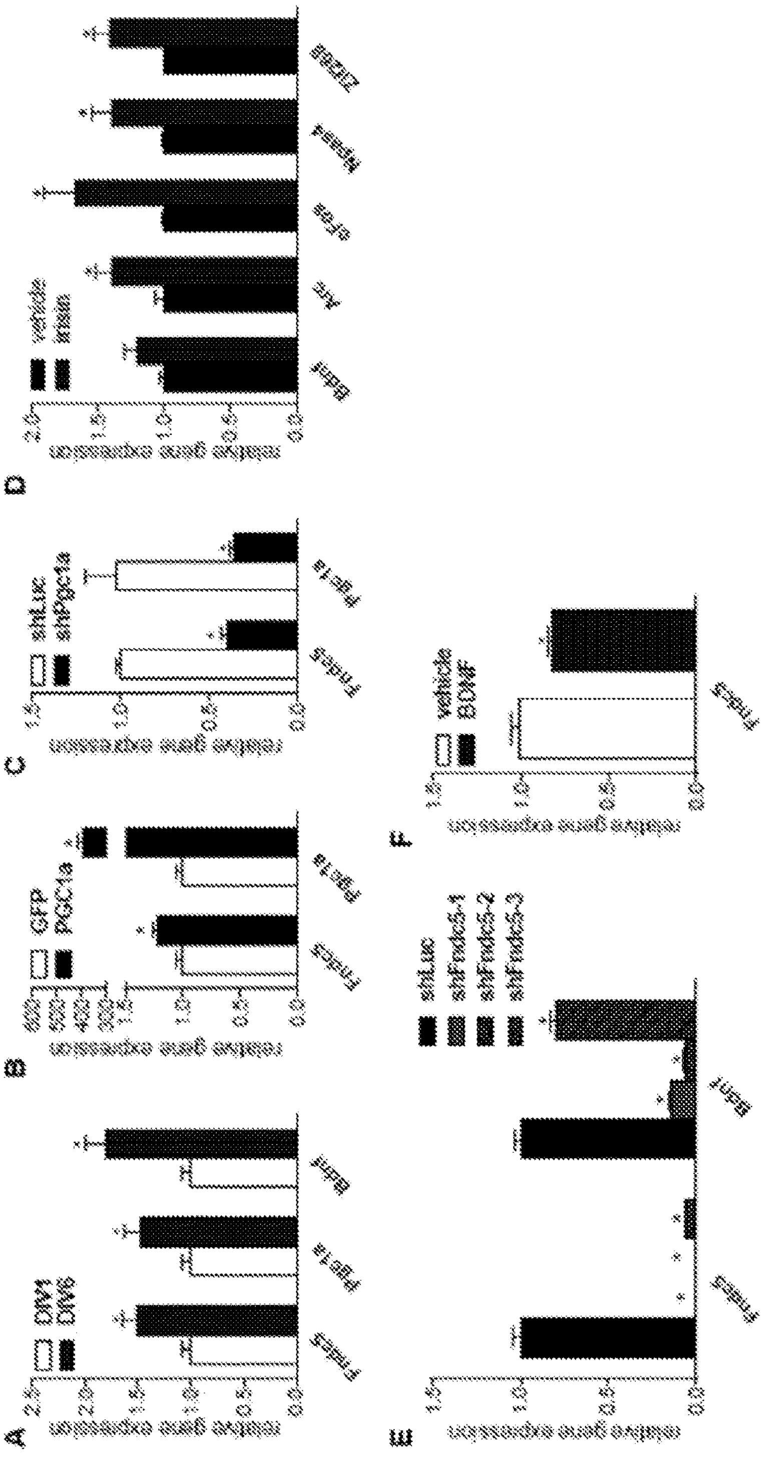
FIGS. 11A-11F show that the PGC-1α/FNDC5/BDNF pathway functions in primary hippocampal neurons.
Figure 12:
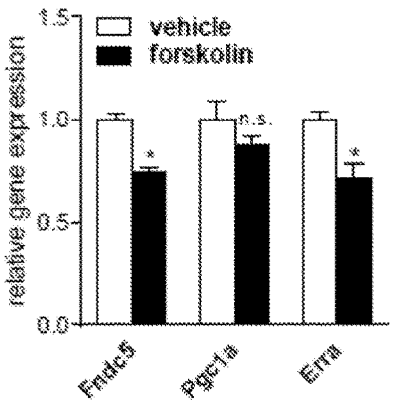
FIG. 12 provides additional data showing that the PGC-1α/FNDC5/BDNF pathway functions in primary hippocampal neurons. Primary hippocampal neurons at DIV 7 were treated with either forskolin (10 μM), a stimulator intracellular cAMP levels, or vehicle for overnight. mRNA was prepared and gene expression was assessed by qPCR. Data are shown as mRNA levels relative to Rsp18 expression, expressed as mean±SEM. *P<0.05 compared to vehicle only group.

Therefore, a key set of experiments were repeated in primary hippocampal neuron cultures. It was confirmed that Fndc5 gene expression is significantly increased in primary hippocampal neurons cultured in vitro from DIV 1 to DIV6 and that the expression of Pgc1a and Bdnf mRNA is similarly increased (FIG. 11A). To test whether PGC-1α regulates Fndc5 gene expression in hippocampal neurons, gain- and loss of function studies were performed. Forced expression of PGC-1α significantly induced Fndc5 gene expression (FIG. 11B). Stimulation with forskolin (10 μM) failed to induce Pgc1a gene expression, but decreased the expression of Erra and Fndc5 (FIG. 12). Efficient knockdown of Pgc1a by lentivirally-delivered shRNA significantly reduced Fndc-5 gene expression (FIG. 11C). Stimulation of primary hippocampal neurons with commercially available recombinant irisin induced a similar gene program (Arc, cFos, Npas4, and Zif268) as was found in the in vivo adenoviral experiments (FIG. 11D). However, the increase in Bdnf gene expression did not reach statistical significance. Loss-of-function of FNDC5 by shRNA mediated-knockdown with three different hairpins against Fndc5 significantly reduced Bdnf gene expression in hippocampal neurons (FIG. 11E). In addition, treatment of hippocampal neurons with recombinant BDNF reduced Fndc5 gene expression (FIG. 11F). Together, these data demonstrate that the basic observations made in the primary cortical neurons also apply to primary hippocampal neuron cultures.

Example 9: Fndc5 is Functionally Associated with Neurodegenerative Disorders

Figure 18:
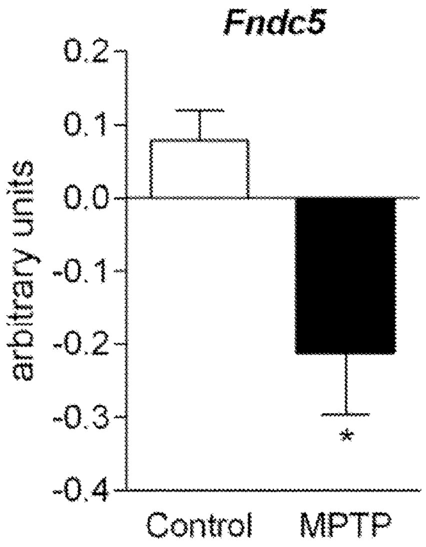
FIG. 18 shows that Fndc5 expression is reduced by MPTP treatment. Mice were treated with MPTP (4 mg/kg/d), the subtantia nigra was harvested 2 days later and gene expression was analyzed by microarray. n=3. Data from Phani et al. (2010) *Brain Res.* 1343:1-13.
Figure 19:
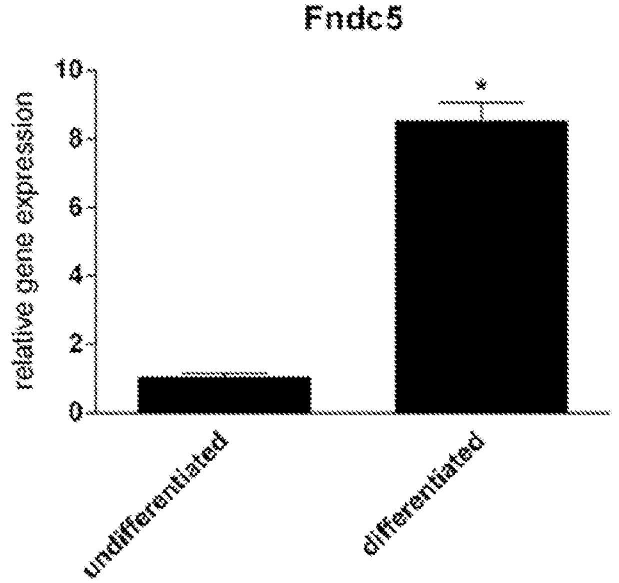
FIG. 19 shows that Fndc5 gene expression increases during differentiation of SH-SY5Y neurons. The cells were differentiated with retinoic acid. Gene expression was assessed with qPCR.
Figure 20:
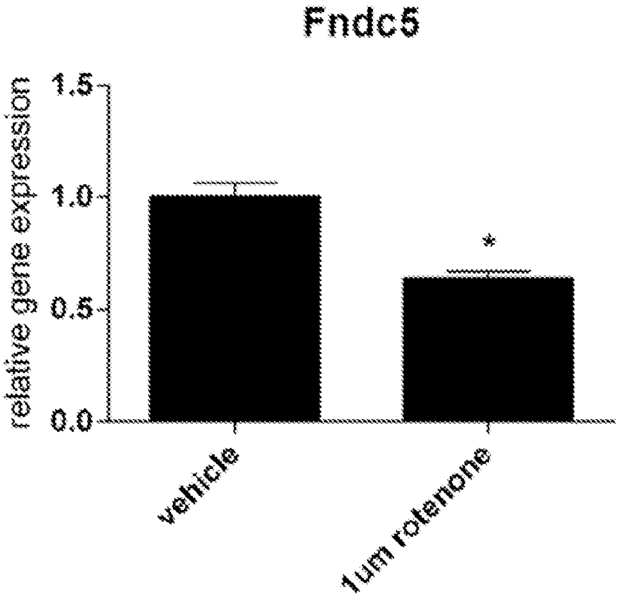
FIG. 20 shows that treatment of SH-SY5Y neurons with the neurotoxin, rotenone, reduces Fndc5 gene expression. Gene expression was assessed with qPCR and the results are consistent with the results shown in FIG. 18.

In addition to promoting neuronal survival described above, Fndc5 expression and activity modulates neurons in neurodegenerative disorders. MPTP (1-methyl-4-phenyl-1,2,3,6-tetrahydropyridine) is a neurotoxin that destroys dopaminergic neurons in the substantia nigra of the brain to thereby model Parkinson's disease (St-Pierre et al. (2006) *Cell* 127, 397-408). FIG. 18 shows that mice treated with MPTP have significantly lower Fndc5 expression in their substantia nigra compared to control mice not treated with MPTP in a human dopaminergic neuronal cell line. SH-SSY5Y, commonly used as a research model of Parkinson's disease, Fndc5 gene expression increases during differentiation of SH-SSY5Y neurons with retinoic acid (FIG. 19) and treatment of SH-SSY5Y neurons with the neurotoxin rotenone commonly used to induce experimental Parkinsonism in animals reduces Fndc5 gene expression (FIG. 20; Krueger et al. (1990) *Biochem. Biophys. Res. Comm.* 169:123-128; and Samantaray et al. (2007) *Neurosci.* 146: 741-755).

Figure 21:
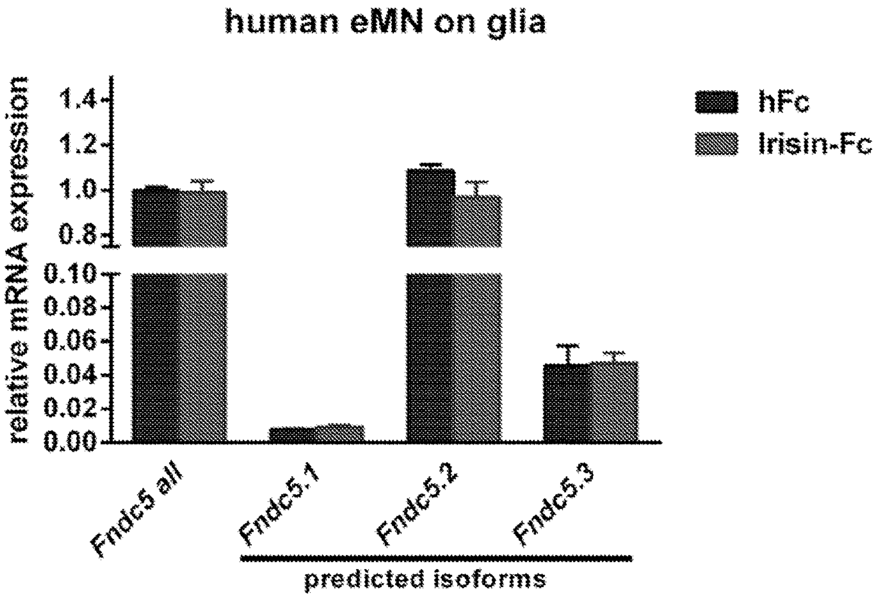
FIG. 21 shows that human embryonic stem cells differentiated into motor neurons (eMN) express Fndc5, with the predicted isoform Fndc5.2 being the most abundant. Gene expression was assessed with qPCR.
Figure 22:
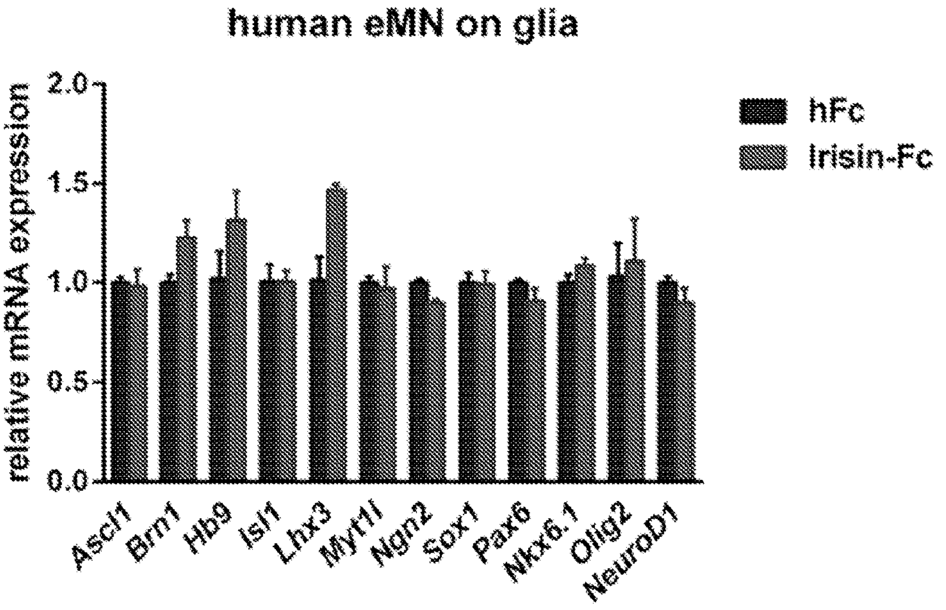
FIG. 22 shows that irisin-Fc promotes motor neuron differentiation of eMN (top panel) and increases eMN synapse formation (bottom panel). Gene expression was assessed with qPCR.
Figure 22:
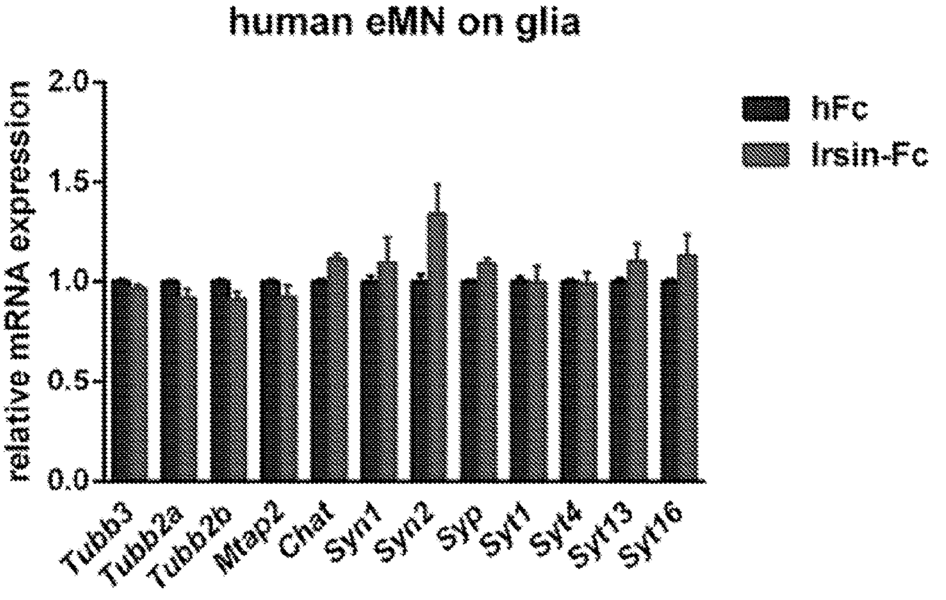

Fndc5 also has effects on motor neuron differentiation and synapse formation. For example, human embryonic stein cells differentiated into motor neurons (eMN) show Fndc5 gene expression in response to irisin (FIG. 21) and, in response, such irisin activity on eMN promotes motor neuron differentiation and increases synapse formation (FIG. 22).

A recent study has reported a positive correlation between human brain size and endurance exercise capacity suggesting a co-evolution between human cognition and locomotion (Raichlen and Gordon (2011) *PLoS ONE* 6, e20601). More complex tasks require a more complex brain and foraging in wide and open spaces in the savannas put high demands on spatial orientation, as well as the ability to acquire and retain new information. Therefore individuals with a more complex brain who performed better at these tasked might have had an evolutionary advantage. On the other hand, since endurance exercise clearly increases expression of BDNF in the brain, improvements in the exercise capacity might have positively enforced brain growth (Mattson (2012) *Ageing Res. Rev.* 11, 347-352), especially in the hippocampus.

Figure 9:
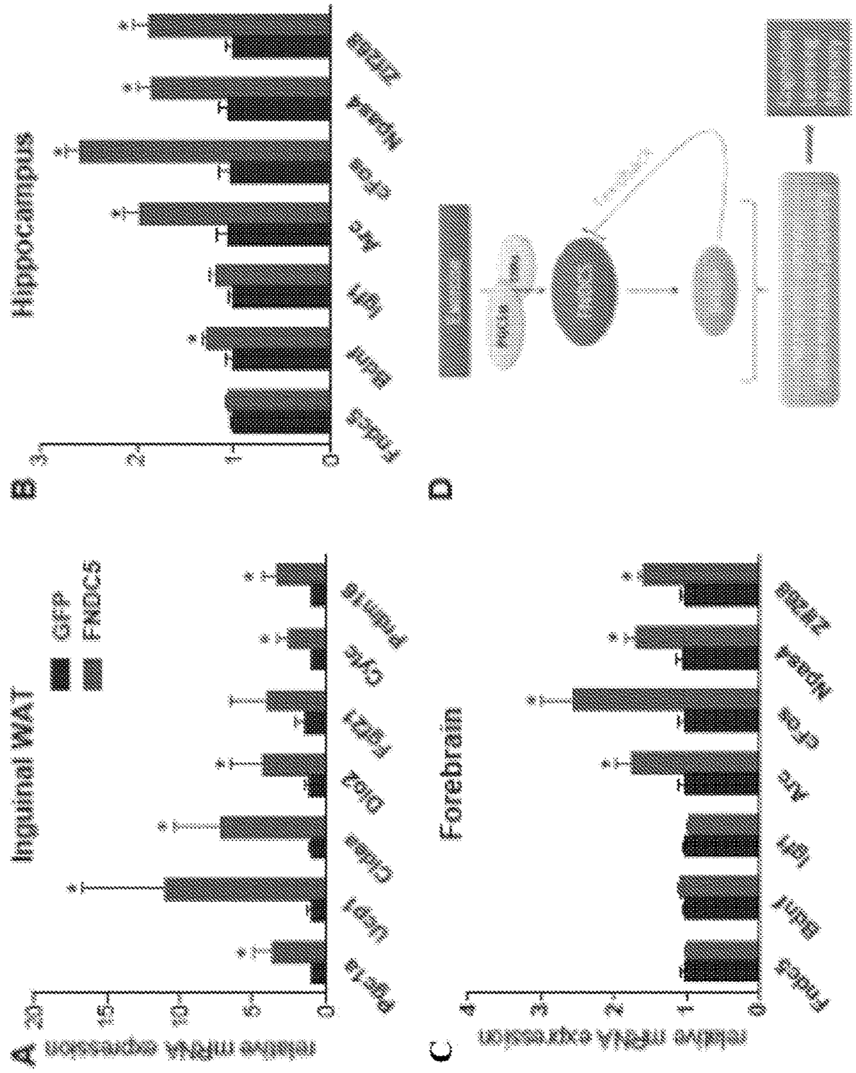
FIGS. 9A-9D shows that peripheral delivery of FNDC5 by adenoviral vectors increases Bdnf expression in the hippocampus.
Figure 10:
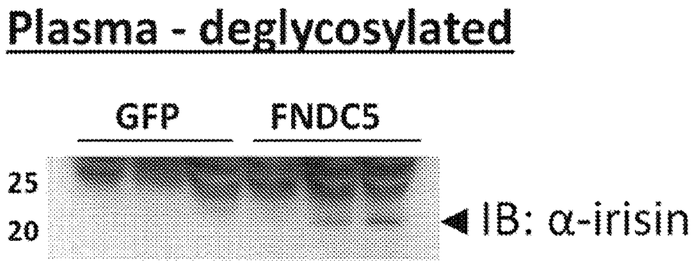
FIG. 10 provides additional data showing that peripheral delivery of FNDC5 by adenoviral vectors increases Bdnf expression in the hippocampus. Five week old male wild-type BALB/c mice were injected with GFP- or FNDC5-expressing adenoviral particles intravenously. Animals were sacrificed seven days later. Plasma samples were collected, depleted from albumin/IgG, deglycosylated, and subjected to WB analysis as shown.

A PGC-1α/FNDC5/BDNF pathway is described herein that is activated in the hippocampus by endurance exercise (FIG. 9). In this model, exercise leads to increased transcription of Pgc1a and Erra. It has been observed previously that PGC-1α often induces the expression of transcription factors to which it binds and co-activates (Handschin et al. (2003) *Proc. Natl. Acad. Sci. U.S.A.* 100, 7111-7116 and Mootha et al. (2004) *Proc. Natl. Acad. Sci. U.S.A.* 101. Indeed, the ability of PGC-1α to induce FNDC5 gene expression depends on ERRα availability (FIG. 6D). This PGC-1α/Erra complex, in turn, likely binds to one or more of the canonical ERRE's found in or near the Fndc5 gene, thus activating Fndc5 gene expression. As shown in a cell culture model in FIG. 8A, FNDC5 is a positive regulator of BDNF expression. Based on this, it is believed that the increased Fndc5 gene expression in exercise will lead to increased BDNF levels. BDNF also can signal to reduce the expression of FNDC5 as part of an apparent homeostatic loop. However, it is believed that there are both FNDC5-dependent and FNDC5-independent pathways by which exercise induces BDNF expression. For example, CREB and NF-kB are two other transcription factors known to induce BDNF expression in exercise (Mattson (2012) *Ageing Res. Rev.* 11, 347-352). These may act upstream or downstream of FNDC5, or in an independent pathway.

The induction of FNDC5 by exercise in the hippocampus is quantitatively comparable to the induction observed in skeletal muscle. It is also in the same quantitative range as the induction of BDNF, a neurotrophic mediator of exercise in the brain, as well as cFos, Arc, and Zif268, important indicators for the activity state of neurons (Hunt et al. (1987) *Nature* 328, 632-634; Lyford et al. (1995) *Neuron* 14, 433-445; Rusak et al. (1990) *Science* 248, 1237-1240; and Saffen et al. (1988) *Proc. Natl. Acad. Sci. U.S.A.* 85, 7795-7799). This places FNDC5 induction in a similar range to other known important regulators in the brain.

In the study analyzing 30 days of free-wheel running exercise, Fndc5 and Pgc1a was induced in the hippocampus but not in the rest of the brain (FIG. 1B) when taken as one unit. Therefore it is believed that Fndc5 and Pgc1a were induced in relatively small numbers of neurons elsewhere, but that that change was not detectable because it is occurring in the background of little or no change in larger brain structures. Indeed, using a longer and more intense exercise regimen exercise protocol and more detailed dissections, Steiner et al. reported an upregulation of Pgc1a expression in various other parts of the brain, in addition to the hippocampus (Steiner et al. (2011) *J. Appl. Physiol.* 111, 1066-1071).

In identifying how exercise is sensed by the brain (e.g., how the 1α/FNDC5/BDNF pathway gets initiated in exercise), one obvious initiator could be increased neuronal activity in areas of the brain that are involved in spatial orientation, learning and memory, since BDNF gene expression is well known to be stimulated by neural activity (West and Greenberg (2011) *Cold Spring Harb. Perspect. Biol.* 3, a005744). Increased sympathetic tone, namely higher norepinephrine levels (Garcia et al. (2003) *Neurosci.* 119, 721-732) and increased IGF-1 levels from periphery crossing the blood-brain-barrier have also been discussed as exercise-related inducers of BDNF (Ding et al. (2006) *Neurosci.* 140, 823-833). However, because exercise is known to change the metabolic state of the whole body, another important factor is believed to be changes in the energy state or ox en levels within the brain, both signals to which PGC-1α gene expression is known to respond in other tissues (Arany et al. (2008) *Nature* 451, 1008-1012 and St-Pierre et al. (2006) *Cell* 127, 397-408). The experiments described herein linked the activation of a metabolic regulator, PGC-1α, via FNDC5 to increased BDNF levels in the neurons in response to exercise (FIG. 9) although other important metabolic regulators exist, such as AMPK or PPARgamma, which have not been part of these studies.

FNDC5 in the periphery is cleaved and secreted as irisin and secreted irisin can cause the 'browning' of adipose tissues (Bostrom et al. (2012) *Nature* 481, 463-468; Shan et al. (2013) *Faseb J.* 27:1981-1989; and Wu et al. (2012) *Cell* 150, 366-376). It has been determined herein that peripheral delivery of FNDC5 with adenoviral vectors is sufficient to induce central expression of Bdnf and others genes with potential neuroprotective functions or those involved in learning and memory. This implies that a secreted, circulating form of FNDC5 has these effects on these neurons and that it crosses the blood brain barrier. The therapeutic implications of this are large since it indicates that a polypeptide can provide neuroprotection in disease states or improved cognition in aging populations.

Example 10: FNDC5 Modulates Neuroprotective Signaling Pathways in Neurons

Figure 23:
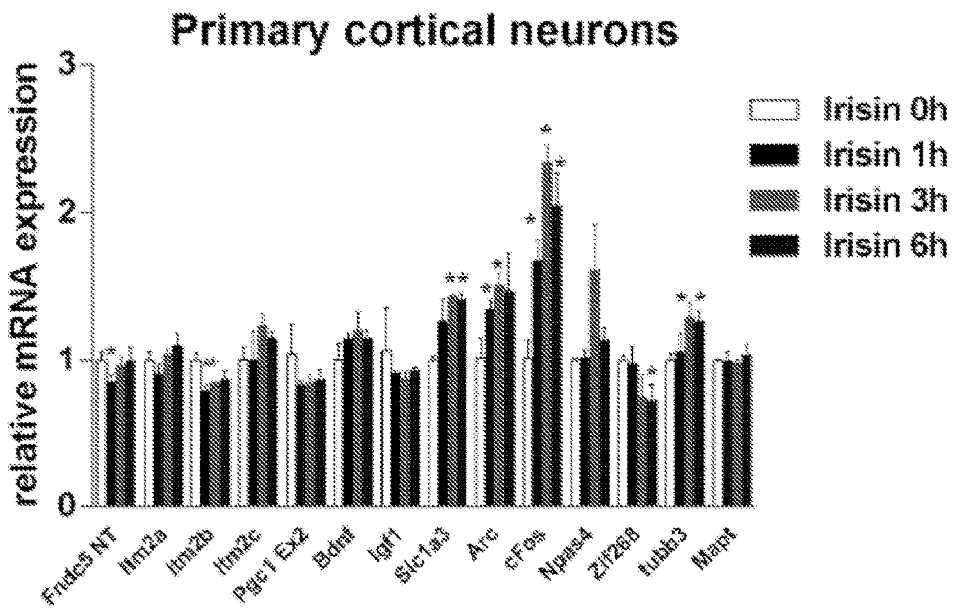
FIGS. 23-26 show that Fndc5 modulates neuronal signaling.
Figure 24:
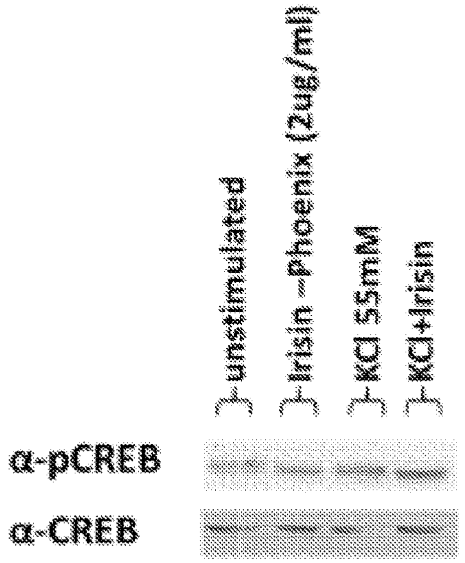
Figure 25:
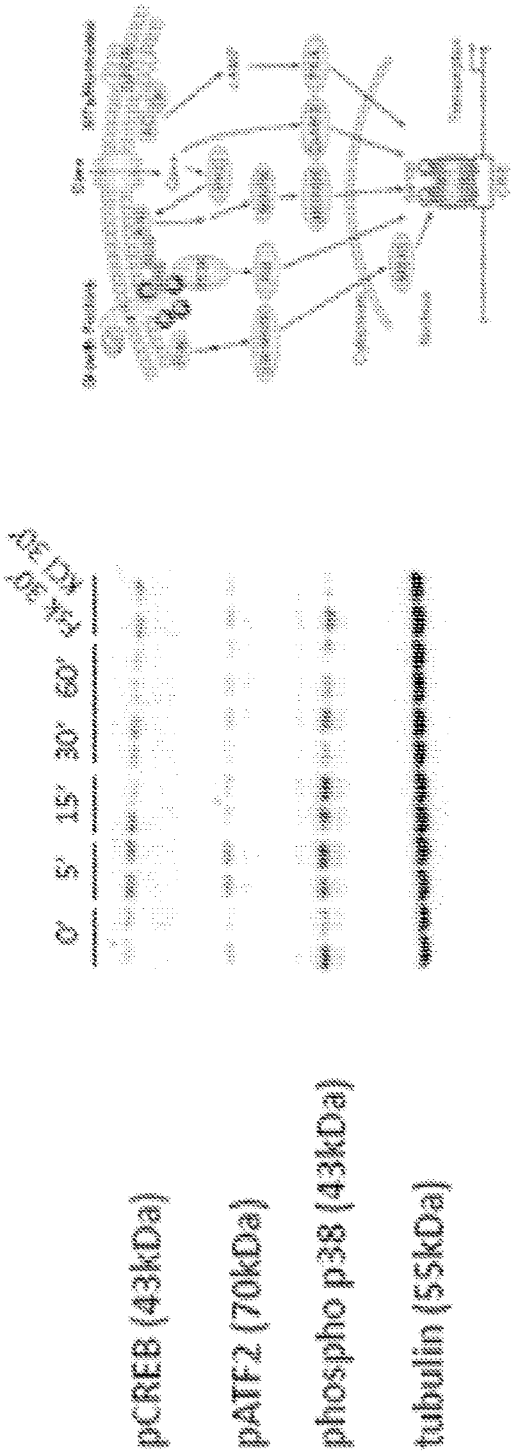
Figure 26:
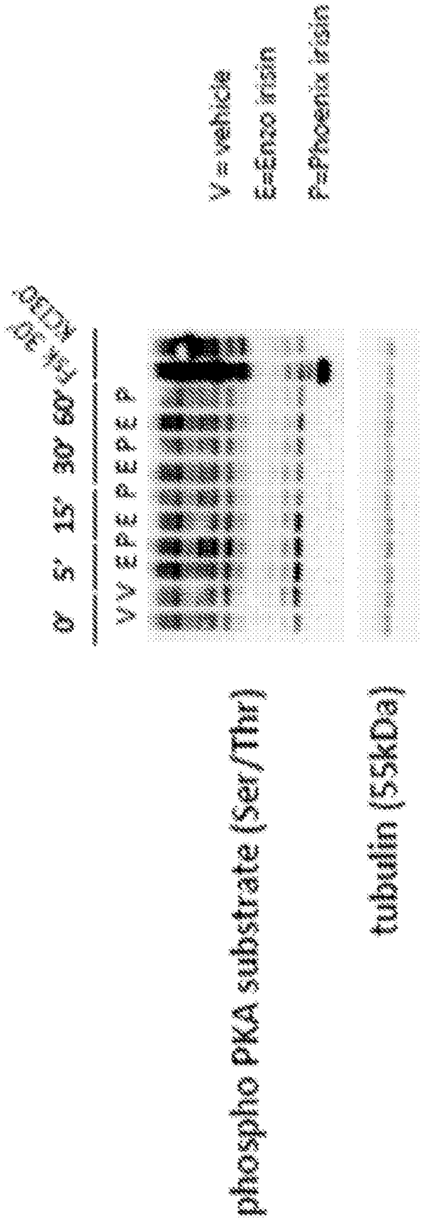

Primary cortical neurons were silenced at DIV6 with 1 uM TTX and 100 uM APV overnight. The neurons were then stimulated at DIV7 using irisin (1 ug/mL; Enzo; Product No. ADI-908-307-0010). FIG. 23 shows the results of changes in mRNA levels of genes of interest in the treated neurons according to time after irisin stimulation and identifies that many of the analyzed genes have statistically significant changes with $p<0.05$ from baseline. In a separate analysis, primary cortical neurons were silenced at DIV6 with 1 uM TTX and 10 uM MK801 overnight. The neurons were then stimulated at DIV6 using irisin (2 ug/mL; Phoenix; Product No. 067-29A) and FIG. 24 shows the results of phosphorylated CREB responses. In still a separate analysis, primary cortical neurons were silenced at DIV6 with 1 uM TTX and 100 uM AP5 overnight. The neurons were then stimulated at DIV6 using irisin (1 ug/mL; Enzo; Product No. ADI-908-307-0010). FIG. 25 shows the time course change of proteins of interest in the wild-type cells treated as described and analyses performed in duplicate. In yet another separate analysis, primary cortical neurons were silenced at DIV7 with 1 uM TTX and 100 uM AP5 overnight. The neurons were then stimulated at DIV8 using 1 ug/mL of irisin from one of two vendors (i.e., either from Enzo, Product No. ADI-908-307-0010, or from Phoenix, Product No. 067-29A). FIG. 26 shows the time course change of proteins of interest in the wild-type cells treated as described and analyses performed in duplicate. These results indicate that FNDC5 modulates neuroprotective signaling pathways in neurons that are involved in improving cell survival, synapse plasticity, and learning and memory.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled, in the art will recognize, or be able to ascertain using no more than routine experimentation, many equivalents to the specific embodiments of the invention described herein. Such equivalents are intended to be encompassed by the following claims.

What is claimed:

1. A method of increasing expression of brain-derived neurotrophic factor (BDNF) by a neuronal cell comprising, contacting the neuronal cell with an agent in vivo, ex vivo, or in vitro, wherein the agent is a nucleic acid that encodes Fndc5 or a fragment thereof, in an amount sufficient to thereby increase the expression of BDNF by the cell, wherein the Fndc5 or fragment thereof is
   a polypeptide comprising an amino acid sequence that is at least 95% identical to the amino acid sequence comprising (i) residues 73-140 of SEQ ID NO:2, (ii) residues 30-140 of SEQ ID NO:2, or (iii) residues 29-140 of SEQ ID NO:2.

2. The method of claim 1, wherein the cell is a neuron.

3. The method of claim 2, wherein the neuron is selected from the group consisting of a hippocampal neuron, a cerebellar neuron, a sciatic nerve neuron, a dopaminergic neuron, and a substantia nigra neuron.

4. The method of claim 1, wherein the Fndc5 nucleic acid or fragment thereof encodes a polypeptide that:
   a) is more than 65 amino acids in length and less than 135 amino acids in length;
   b) is between 70 and 125 amino acids in length;
   c) is less than 195 amino acids in length;
   d) is glycosylated;
   e) is pegylated;
   f) comprises an amino acid sequence that is heterologous to said FNDC5 polypeptide; and/or
   g) can cross the blood-brain barrier.

5. The method of claim 4, wherein
   i) the at least one glycosylated amino acid residue in e) corresponds to asparagine at position 36 and/or the asparagine at position 81 of SEQ ID NO:2; and/or
   ii) the said heterologous amino acid sequence in f) is an Fc domain, an IgG1 Fc domain, an IgG2 Fc domain, an IgG3 Fc domain, and IgG4 Fc domain, a dimerization domain, an oligomerization domain, an agent that promotes plasma solubility, albumin, a signal peptide, a peptide tag, a 6-His tag, a thioredoxin tag, a hemaglutinin tag, a GST tag, or an OmpA signal sequence tag.

6. A method for treating a neurological disease or disorder in a subject comprising administering to the subject a sufficient amount of an agent, wherein the agent is a nucleic acid that encodes Fndc5 or a fragment thereof, wherein the agent increases BDNF expression or activity in the central or peripheral nervous system of the subject, such that the neurological disease or disorder is treated, and wherein the Fndc5 or fragment thereof is
   a polypeptide comprising an amino acid sequence that is at least 95% identity to the amino acid sequence comprising (i) residues 73-140 of SEQ ID NO:2, (ii) residues 30-140 of SEQ ID NO:2, or (iii) residues 29-140 of SEQ ID NO:2.

7. The method of claim 6, wherein the Fndc5 nucleic acid or fragment thereof encodes a polypeptide that:
   a) is more than 65 amino acids in length and less than 135 amino acids in length;
   b) is between 70 and 125 amino acids in length;
   c) is less than 195 amino acids in length;
   d) is glycosylated;
   e) is pegylated;
   f) comprises an amino acid sequence that is heterologous to said FNDC5 polypeptide; and/or
   g) can cross the blood-brain barrier.

8. The method of claim 7, wherein
   i) the at least one glycosylated amino acid residue in e) corresponds to asparagine at position 36 and/or the asparagine at position 81 of SEQ ID NO:2; and/or
   ii) the said heterologous amino acid sequence in f) is an Fc domain, an IgG1 Fc domain, an IgG2 Fc domain, an IgG3 Fc domain, and IgG4 Fc domain, a dimerization domain, an oligomerization domain, an agent that promotes plasma solubility, albumin, a signal peptide, a peptide tag, a 6-His tag, a thioredoxin tag, a hemaglutinin tag, a GST tag, or an OmpA signal sequence tag.

9. The method of claim 6, wherein the neurological disease or disorder would benefit from decreased neuronal cell death and/or increased neuronal survival.

10. The method of claim 9, wherein the neurological disease or disorder is selected from the group consisting of Alzheimer's disease, Parkinson's disease, Huntington's disease, Pick's disease, Kuf's disease, Lewy body disease, neurofibrillary tangles, Rosenthal fibers, Mallory's hyaline, senile dementia, myasthenia gravis, Gilles de la Tourette's syndrome, multiple sclerosis (MS), amyotrophic lateral sclerosis (ALS), progressive supranuclear palsy (PSP), epilepsy, Creutzfeldt-Jakob disease, deafness-dytonia syndrome, Leigh syndrome, Leber hereditary optic neuropathy (LHON), parkinsonism, dystonia, motor neuron disease, neuropathy-ataxia and retinitis pimentosa (NARP), maternal inherited Leigh syndrome (MILS), Friedreich ataxia, hereditary spastic paraplegia, Mohr-Tranebjaerg syndrome, Wilson disease, sporatic Alzheimer's disease, sporadic amyotrophic lateral sclerosis, sporadic Parkinson's disease, autonomic function disorders, hypertension, sleep disorders, neuropsychiatric disorders, depression, schizophrenia, schizoaffective disorder, korsakoff's psychosis, mania, anxiety disorders, phobic disorder, learning or memory disorders, amnesia or age-related memory loss, attention deficit disorder, dysthymic disorder, major depressive disorder, obsessive-compulsive disorder, psychoactive substance use disorders, panic disorder, bipolar affective disorder, severe bipolar affective (mood) disorder (BP-1), migraines, hyperactivity and movement disorders.

11. The method of claim 6, wherein the agent is administered systemically.

12. The method of claim 6, wherein the subject is a human.

* * * * *

UNITED STATES PATENT AND TRADEMARK OFFICE

CERTIFICATE OF CORRECTION

PATENT NO. : 10,286,042 B2
APPLICATION NO. : 15/026381
DATED : May 14, 2019
INVENTOR(S) : Bruce M. Spiegelman et al.

It is certified that error appears in the above-identified patent and that said Letters Patent is hereby corrected as shown below:

In the Specification

At Column 1, Lines 15-18, after Statement of Rights, please replace:
"This invention was made with government support under grant numbers RO1 DK31405 and DK90861 awarded by The National Institutes of Health. The government has certain rights in the invention."

With:
-- This invention was made with government support under grant numbers DK090861, DK031405, and NS087096 awarded by The National Institutes of Health. The government has certain rights in the invention. --

Signed and Sealed this
Seventeenth Day of September, 2019

Andrei Iancu
*Director of the United States Patent and Trademark Office*